(12) United States Patent
Ben Menachem et al.

(10) Patent No.: US 11,964,120 B2
(45) Date of Patent: *Apr. 23, 2024

(54) LONG ACTING GASTRIC RESIDENCE SYSTEM

(71) Applicant: CLEXIO BIOSCIENCES LTD., Jerusalem (IL)

(72) Inventors: Avshalom Ben Menachem, Zur Izhak (IL); Ilan Zalit, Rosh Ha'ayin (IL)

(73) Assignee: Clexio Biosciences Ltd., Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 18/056,387

(22) Filed: Nov. 17, 2022

(65) Prior Publication Data

US 2023/0131186 A1    Apr. 27, 2023

Related U.S. Application Data

(63) Continuation of application No. 16/769,046, filed as application No. PCT/IB2018/059579 on Dec. 3, 2018, now Pat. No. 11,547,839.

(Continued)

(51) Int. Cl.
*A61M 31/00* (2006.01)
*A61K 9/00* (2006.01)
*A61J 3/07* (2006.01)

(52) U.S. Cl.
CPC ......... *A61M 31/002* (2013.01); *A61K 9/0065* (2013.01); *A61J 3/07* (2013.01); *A61M 2210/1053* (2013.01)

(58) Field of Classification Search
None
See application file for complete search history.

(56) References Cited

U.S. PATENT DOCUMENTS

| 1,318,259 A | 10/1919 | Bohne |
| 3,844,285 A | 10/1974 | Laby |

(Continued)

FOREIGN PATENT DOCUMENTS

| EP | 0202159 A2 | 11/1986 |
| EP | 0344939 A2 | 12/1989 |

(Continued)

OTHER PUBLICATIONS

Bardonnet et al., "Gastroretentive Dosage Forms: Overview and Special Case of Helicobacter Pylori", Journal of Controlled Release 111, 2006, 1-18.

(Continued)

*Primary Examiner* — Dominic Lazaro
(74) *Attorney, Agent, or Firm* — BakerHostetler

(57) ABSTRACT

Provided herein are gastroretentive dosage forms (GRDFs) for extended retention in a human stomach, comprising a body comprising at least two arms, the body configured to transform between a collapsed configuration for ingestion, an expanded configuration for retention within the stomach and a disassembled configuration wherein after a predetermined time period has elapsed, the GRDF disassembles into at least two parts such that each of the disassembled parts of the GRDF is sized for exiting the stomach; and, an erodible insert comprising a therapeutic agent, a diagnostic agent, an electronic device, or a combination thereof.

12 Claims, 30 Drawing Sheets

Related U.S. Application Data

(60) Provisional application No. 62/681,525, filed on Jun. 6, 2018, provisional application No. 62/594,257, filed on Dec. 4, 2017.

(56) References Cited

U.S. PATENT DOCUMENTS

| | | | |
|---|---|---|---|
| 4,220,153 | A | 9/1980 | Dresback |
| 4,735,804 | A | 4/1988 | Caldwell et al. |
| 4,767,627 | A | 8/1988 | Caldwell et al. |
| 5,002,772 | A | 3/1991 | Curatolo et al. |
| 5,443,843 | A | 8/1995 | Curatolo et al. |
| 5,780,057 | A | 7/1998 | Conte et al. |
| 6,488,962 | B1 | 12/2002 | Berner et al. |
| 6,685,962 | B2 | 2/2004 | Friedman et al. |
| 6,723,340 | B2 | 4/2004 | Gusler et al. |
| 6,753,011 | B2 | 6/2004 | Faour |
| 7,976,870 | B2 | 7/2011 | Berner et al. |
| 8,298,574 | B2 | 10/2012 | Tsabari et al. |
| 8,329,215 | B2 | 12/2012 | Berner et al. |
| 8,460,706 | B2 | 6/2013 | Vergnault et al. |
| 8,586,083 | B2 | 11/2013 | Mohammad |
| 8,609,136 | B2 | 12/2013 | Tsabari et al. |
| 8,753,678 | B2 | 6/2014 | Tsabari et al. |
| 10,182,985 | B2 | 1/2019 | Bellinger et al. |
| 10,195,143 | B2 | 2/2019 | Zalit et al. |
| 10,485,758 | B2 | 11/2019 | Menachem et al. |
| 10,737,079 | B2 | 8/2020 | Ben et al. |
| 11,547,839 | B2 * | 1/2023 | Menachem .......... A61K 9/0065 |
| 2005/0202090 | A1 | 9/2005 | Clarke |
| 2008/0241238 | A1 | 10/2008 | Dharmadhikari et al. |
| 2008/0299197 | A1 | 12/2008 | Toneguzzo et al. |
| 2009/0324694 | A1 | 12/2009 | Mohammad |
| 2010/0112053 | A1 | 5/2010 | Momose et al. |
| 2011/0066175 | A1 | 3/2011 | Gross |
| 2011/0117190 | A1 | 5/2011 | Brown et al. |
| 2011/0117192 | A1 | 5/2011 | Navon et al. |
| 2011/0268666 | A1 | 11/2011 | Friedman et al. |
| 2011/0301129 | A1 | 12/2011 | Berner et al. |
| 2012/0021009 | A1 | 1/2012 | Prinderre et al. |
| 2012/0263792 | A1 | 10/2012 | Lim et al. |
| 2012/0321706 | A1 | 12/2012 | Masri et al. |
| 2013/0072869 | A1 | 3/2013 | Cutchis et al. |
| 2013/0164377 | A1 | 6/2013 | Berner et al. |
| 2013/0197441 | A1 | 8/2013 | Tsabari et al. |
| 2014/0017303 | A1 | 1/2014 | Navon et al. |
| 2014/0148840 | A1 | 5/2014 | Mintchev et al. |
| 2015/0033850 | A1 | 2/2015 | Jeung et al. |
| 2015/0035423 | A1 | 2/2015 | Raunikar |
| 2015/0342877 | A1 | 12/2015 | Menachem et al. |
| 2016/0064439 | A1 | 3/2016 | Or-Bach et al. |
| 2017/0106099 | A1 | 4/2017 | Bellinger et al. |

FOREIGN PATENT DOCUMENTS

| | | | |
|---|---|---|---|
| EP | 0415671 | B1 | 3/1995 |
| EP | 1915990 | A1 | 4/2008 |
| EP | 2329810 | A1 | 6/2011 |
| GB | 1318259 | A | 5/1973 |
| JP | 62-026215 | A | 2/1987 |
| JP | 02-029268 | A | 1/1990 |
| JP | 03-163011 | A | 7/1991 |
| JP | 2012-500230 | A | 1/2012 |
| JP | 2017-518308 | A | 7/2017 |
| JP | 2017-519003 | A | 7/2017 |
| WO | 03/57197 | A1 | 7/2003 |
| WO | 2006/072948 | A2 | 7/2006 |
| WO | 2007/010847 | A1 | 1/2007 |
| WO | 2007/072495 | A2 | 6/2007 |
| WO | 2007/093999 | A1 | 8/2007 |
| WO | 2007/106960 | A1 | 9/2007 |
| WO | 2009/144558 | A1 | 12/2009 |
| WO | 2010/035273 | A2 | 4/2010 |
| WO | 2011/048494 | A2 | 4/2011 |
| WO | 2011/090724 | A3 | 11/2011 |
| WO | 2012/006961 | A1 | 1/2012 |
| WO | 2012/006963 | A1 | 1/2012 |
| WO | 2012/059815 | A1 | 5/2012 |
| WO | 2013/054285 | A1 | 4/2013 |
| WO | 2015/083171 | A1 | 6/2015 |
| WO | 2015/187746 | | 12/2015 |
| WO | 2015/191920 | A1 | 12/2015 |
| WO | 2015/191922 | A1 | 12/2015 |
| WO | 2015/191925 | A1 | 12/2015 |
| WO | 2018/102799 | A1 | 6/2018 |

OTHER PUBLICATIONS

Bellinger et al., "Oral, Ultra-long-lasting Drug Delivery: Application Toward Malaria Elimination Goals", Sci. Transl. Med., 8, 2016, 365ra157.
Cardinal et al., "Gastric Retentive Drug Delivery Systems", Oral Bioavailability, 2011, 329-341.
Definition of "detach". Accessed online on Nov. 16, 2020 at https://www.merriam-webster.com. (Year: 2020).
Definition of "disengage". Accessed online on Nov. 16, 2020 at https://www.merriam-webster.com. (Year: 2020).
Definition of "insert". Merriam-Webster. Accessed online on Jul. 10, 2021 at merriam-webster.com (Year: 2021).
Fix et al., "Controlled Gastric Emptying, III. Gastric Residence Time of a Nondisintegrating Geometric Shape in Human Volunteers", Pharmaceutical Research, 1993, 10, 7, 1087-1089.
Hwang et al., Gastric Retentive Drug-Delivery Systems, Critical Reviews in Therapeutic Drug Carrier Systems, vol. 15 No. 3 pp. 243-284 (1998).
International Preliminary Report on Patentability dated May 20, 2016 in Corresponding International Application No. PCT/US15/33850, 12 pages.
International Search Report dated Oct. 23. 2015 in corresponding International Application No. PCT/US15/33850.
Khosla et al., "The Effect of Tablet Size on the Gastric Emptying of Non-Disintegrating Tablets", International Journal of Pharmaceutics, 1990, 62(2-3), R9-R11.
Klausner et al., "Expandable Gastrorentative Dosage Forms", Journal of Controlled Release, 2003, 90, 143-162.
Lopes et al., "Overview on Gastroretentive Drug Delivery Systems for Improving Drug Bioavailability", International Journal of Pharmaceutics, 2016, 144-158.
McLauchlan et al. "Comparison of gastric body and antral pH: a 24 hour ambulatory study in healthy volunteers" Gut, Oct. 1989, 30, pp. 573-578. (Year: 1989).
Rowe et al., Handbook of Pharmaceutical Excipients, "Cellulose Acetate Phthalate", 6th ed., 2009, Pharmaceutical Press, pp. 191-193. (Year: 2009).
Rowe et al., Handbook of Pharmaceutical Excipients, "Hypropmellose Phthalate", 6th ed., 2009, Pharmaceutical Press, pp. 333-336. (Year: 2009).
Sakshi, "Gastroretentive Drug Delivery Systems: An Overview", IPS, 2013, 37-45.
Sharma et al., "Gastroretentive Drug Delivery System: An Approach to Enhance Gastric Retention for Prolonged Drug Release", IJPSR, 2014, vol. 5(4), pp. 1095-1106.
Shivram et al., "Gastro Rententive Drug Delivery System: A Review", IJPRAS, 2012, 1-13.
Tibbitt, "Emerging Frontiers in Drug Delivery", JACS, 2016, 138, 704-717.
Timmermans et al., "The Cutoff Size for Gastric Emptying of Dosage Forms", J. Pharm. Sci., Aug. 1993, 82(8), 854.
Wang, Xiaobo, Drug Release System, China Medical Science Press, Chapter 27, Aug. 2007, pp. 483-485.
Zema, L. et al., "Gastroresistant Capsular Device Prepared By Injection Molding," International Journal of Pharmaceuticals, Jan. 2013, pp. 264-272, vol. 440.
Zema, L. et al., "Injection Molding and its Application to Drug Delivery," Journal of Controlled Release, May 2012, pp. 324-331, vol. 159, Issue 3.

(56) References Cited

OTHER PUBLICATIONS

Zhoa et al., "Gastroretentive Drug Delivery Systems for the Treatment of Helicobacter Pylori", World J. Gastroenterology, Jul. 28, 2014, 20(28), 9321-9329.

* cited by examiner

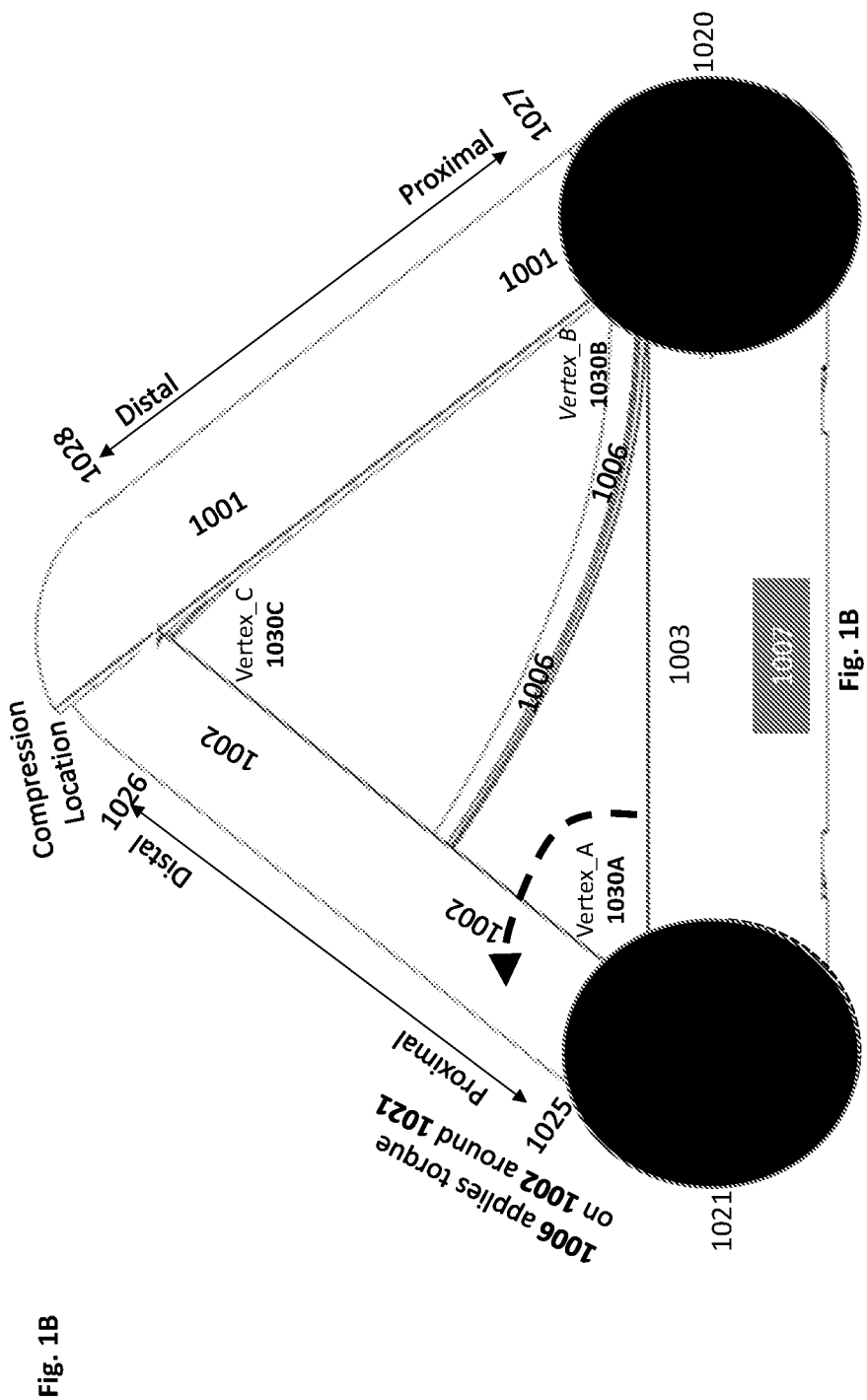

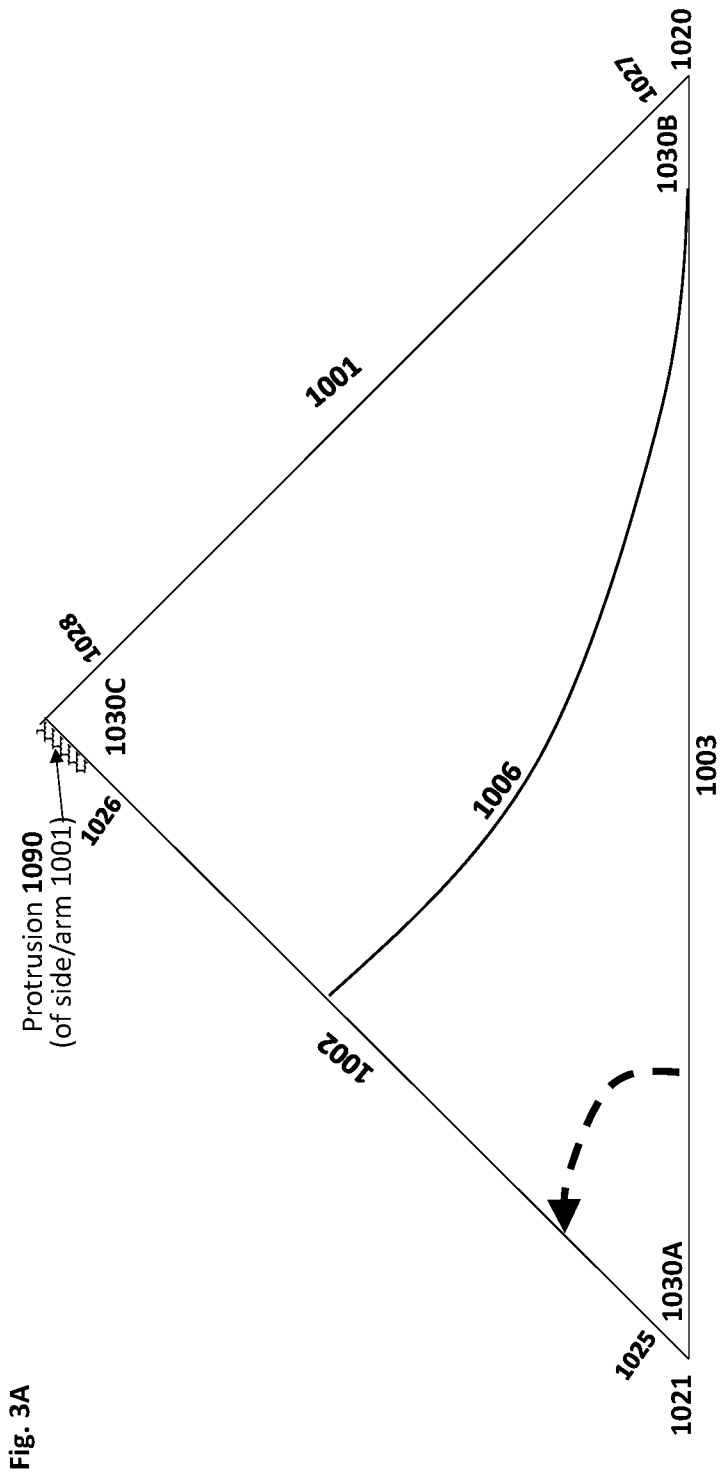

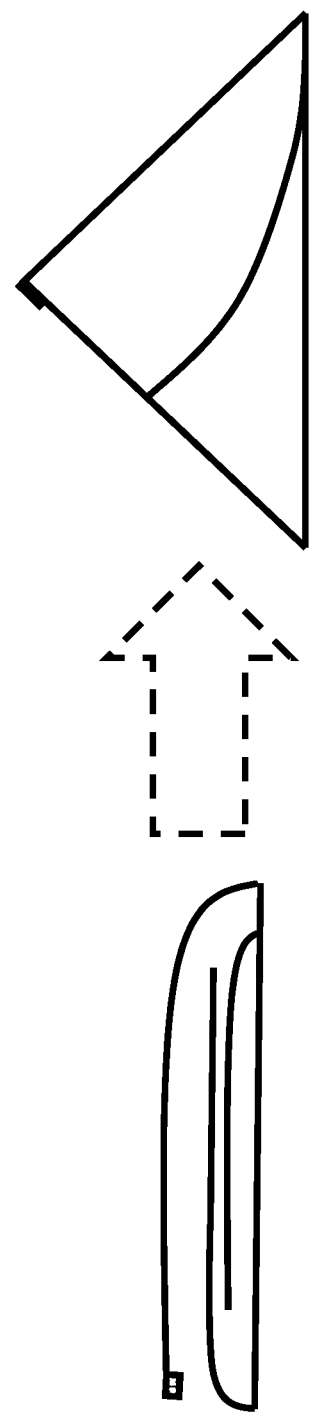

Time
T=t2

Time
T=t4

Time
T=t1

Time
T=t3

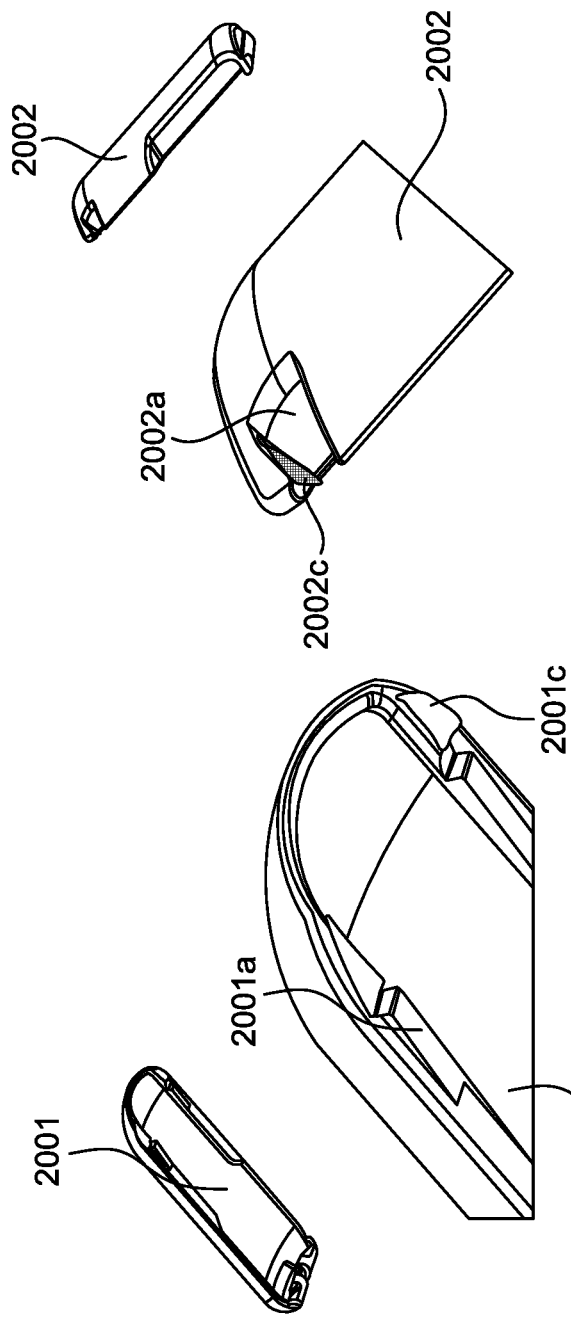
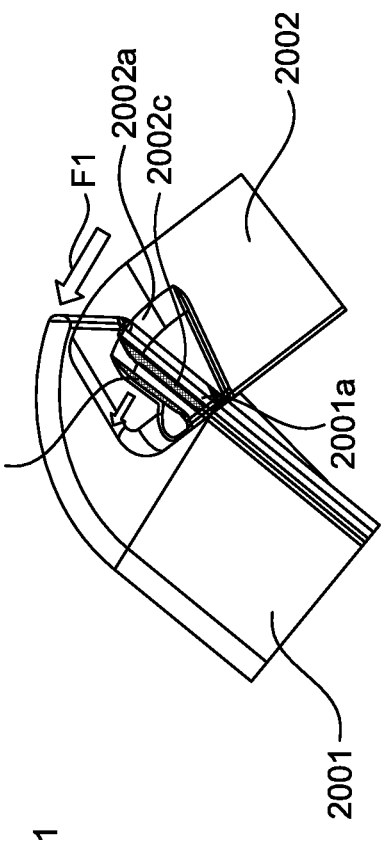
FIG. 12A
Fig. 12B
Fig. 12C

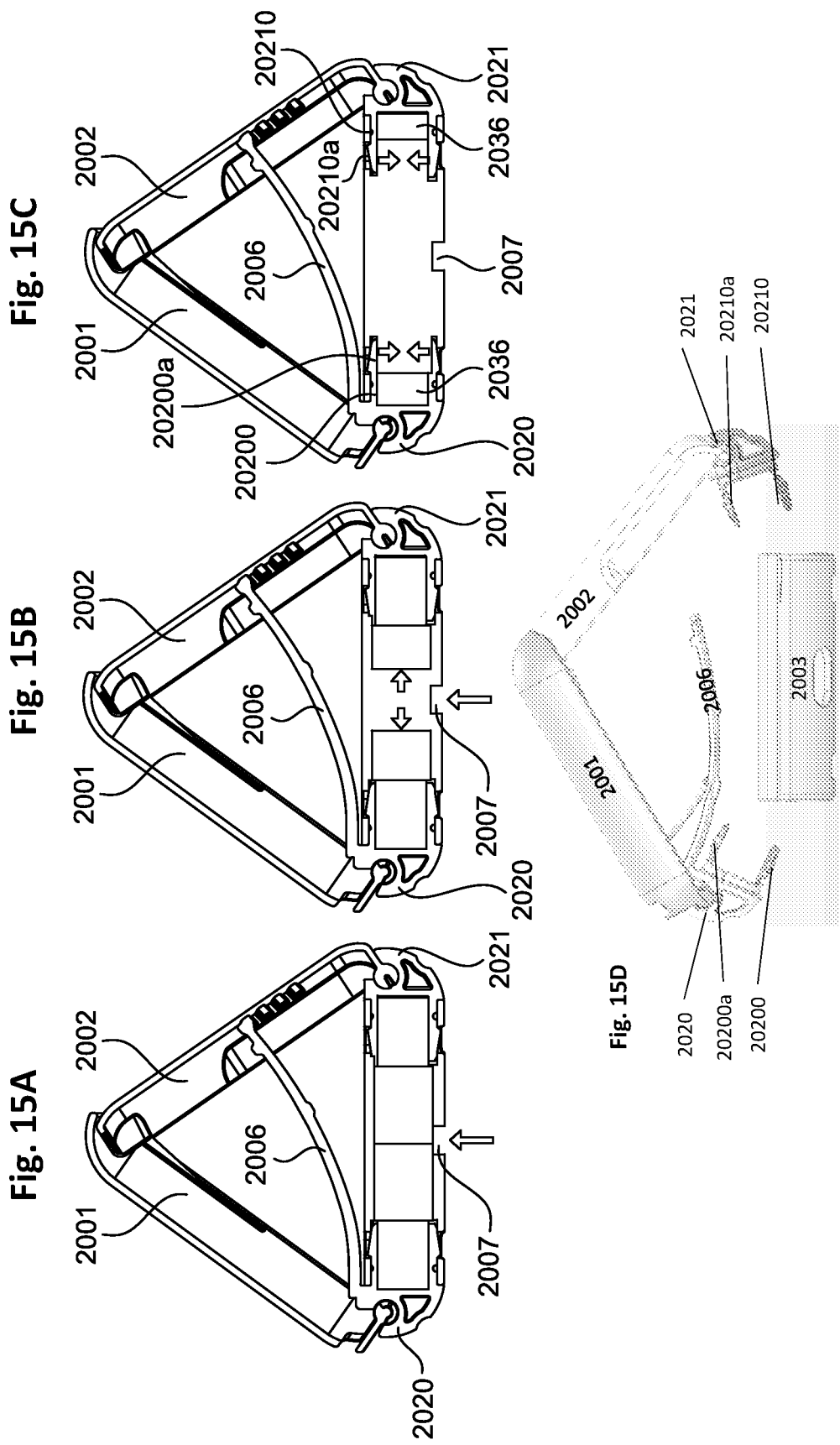

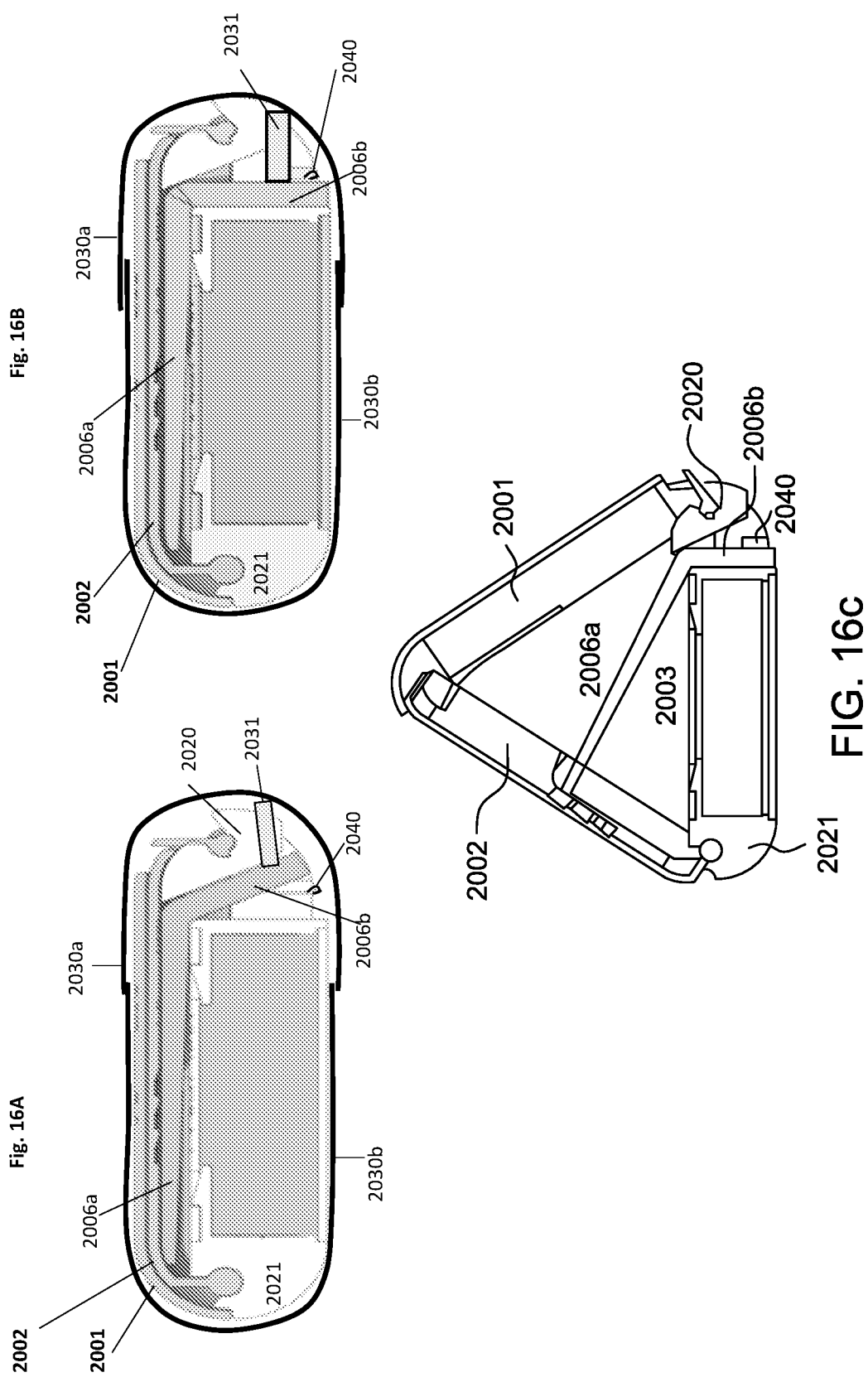

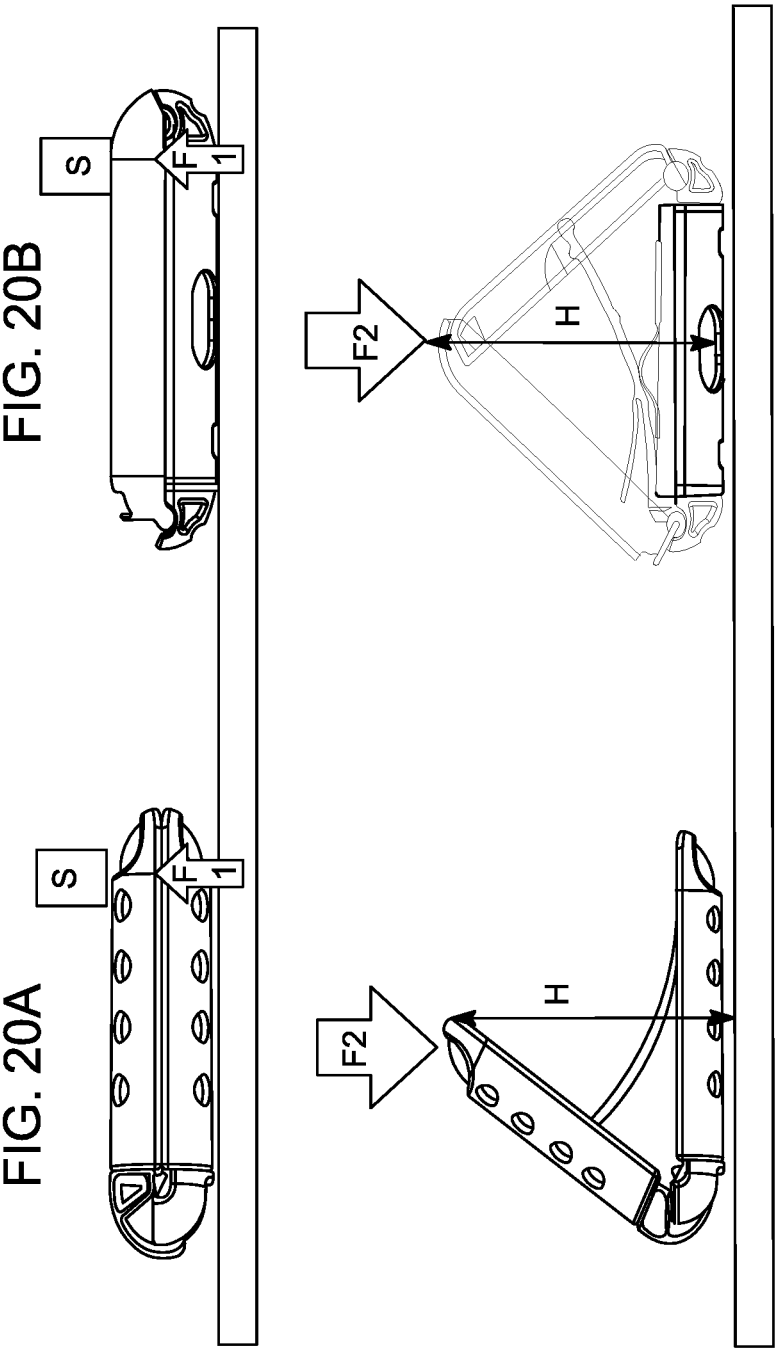

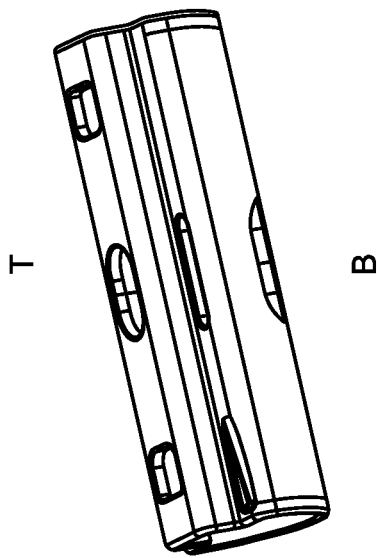
Fig. 21B
Fig. 21C
| holes surface area (mm²) | | |
|---|---|---|
| L | M | S |
| 59.8 | 40.7 | 26.2 |
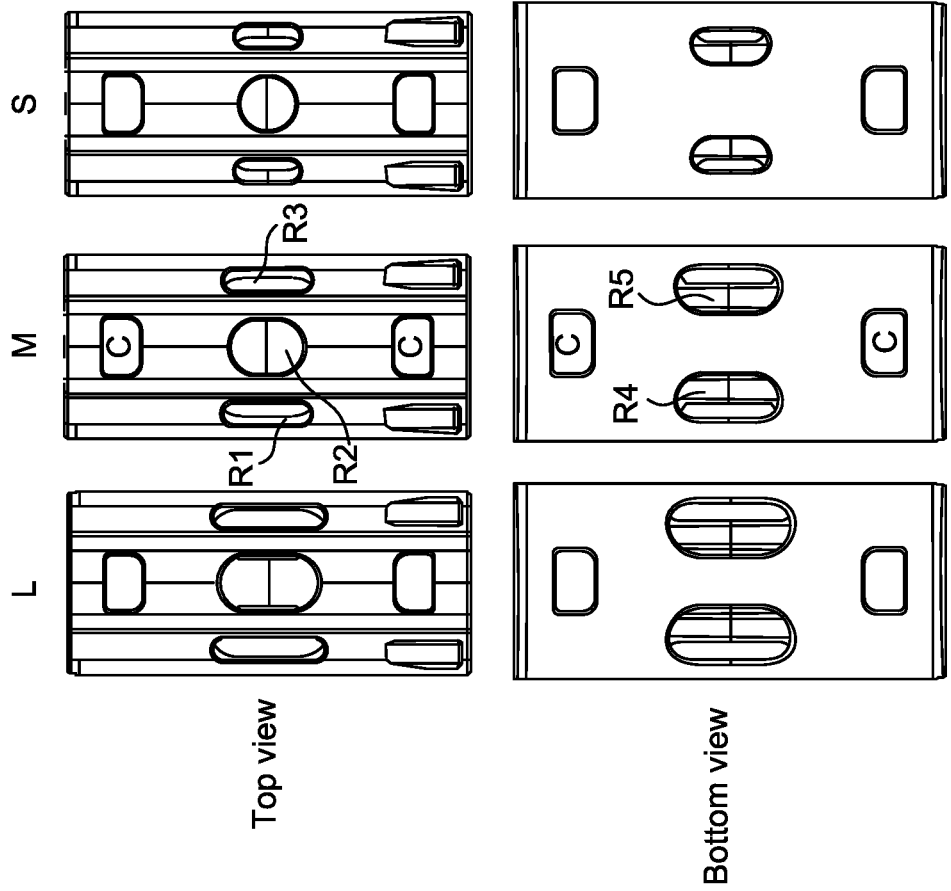
FIG. 21A

LONG ACTING GASTRIC RESIDENCE SYSTEM

CROSS-REFERENCE TO RELATED APPLICATIONS

This application is a continuation of U.S. Ser. No. 16/769,046, filed Jun. 2, 2020, which is the National Stage Application of International Patent Application No. PCT/IB2018/059579, filed Dec. 3, 2018, which claims the benefit of U.S. provisional application No. 62/594,257 filed Dec. 4, 2017, and U.S. provisional application No. 62/681,525 filed Jun. 6, 2018, the entire disclosures of each of which are incorporated herein by reference.

TECHNICAL FIELD

The present disclosure relates to a pharmaceutical product or system. More particularly, the present disclosure relates to gastric residence systems or gastroretentive dosage forms (GRDF) useful for extended retention of therapeutic agents, diagnostic agents and/or electronic devices in the stomach.

BACKGROUND

Gastric residence systems (GRS) are delivery systems which remain in the stomach for extended periods of time. They enable oral delivery of an active pharmaceutical ingredient (API), diagnostic or electronic device etc. to the gastrointestinal (GI) tract, for example for the purpose of extended GI residence, for local treatment of the upper GI, for continuous exposure of API especially those with a narrow absorption window or low solubility in the intestine. Gastric residence systems fall within three areas of technology: namely floating systems, bio-adhesives and systems with expanding geometry through swelling or unfolding.

Folding systems are conveniently administered to a patient in a folded or compacted form for example via a capsule. Once in the stomach, dissolution of the capsule in the stomach results in the system expanding or unfolding to a size which resists passage through the pyloric sphincter over the desired residence period. Examples of such systems are described in the following publications: U.S. Pat. No. 4,735,804, PCT/US2015/033850, PCT/US2015/035423 and PCT/IB2011/002888.

Requirements for folding systems include providing a safe and pharmaceutically acceptable system which is compact for swallowing, able to unfold to an effective expanded system that can endure the mechanically and chemically harsh environment of the stomach for a desired residence period and eventually exit the stomach safely and in a timely manner. The present disclosure describes advancements in the design of improved structures for extended residence in the stomach.

To date, there are no approved products for oral delivery to the human upper gastro-intestinal tract and specifically to the stomach which release active agents for more than 24 hours.

A gastric retentive product having the ability to retain therapeutic or diagnostic agents, and/or electronic devices in the stomach over at least about 48 hours, at least about 3 days, at least about 4 days, at least about 5 days, at least about 6 days, at least about 7 days or at least about 8 days is desired.

SUMMARY

Aspects of the invention are defined herein below and in the accompanying claims.

The subject invention provides a gastroretentive dosage form (GRDF) for extended retention in a human stomach, comprising:
  a body comprising at least two arms, the body configured to transform between a collapsed configuration for ingestion, an expanded configuration for retention within the stomach and a disassembled configuration wherein after a predetermined time period has elapsed, the GRDF mechanically disassembles into at least two parts such that each of the disassembled parts of the GRDF is sized for exiting the stomach; and
  an erodible insert comprising a therapeutic agent, a diagnostic agent, an electronic device, or a combination thereof;
  wherein the disassembled configuration is induced by at least partial erosion of the erodible insert, and wherein the GRDF is adapted to be retained in the stomach for at least 3 days, at least 4 days, at least 4.7 days, at least 5 days, at least 6 days, at least 6.6 days, at least 7 days, at least 8 days, or at least 8.3 days.

The subject invention also provides a mechanism for priming of a GRDF for administering to a patient, the GRDF comprising:
  a body including at least two arms, the body configured to transform between a collapsed configuration for ingestion, an expanded configuration for retention within the stomach and a disassembled configuration, wherein after a predetermined time period has elapsed, the GRDF disassembles into at least two parts such that each of the disassembled parts of the GRDF is sized for exiting the stomach,
  an erodible insert comprising a therapeutic agent, a diagnostic agent, an electronic device, or a combination thereof;
  a biasing member having a first portion and a second portion;
  a retainer configured to house the GRDF for ingestion, wherein the retainer has a main portion and a closing portion, wherein the retainer is configured to retain the GRDF in the collapsed configuration; and
  a priming member extending from an interior side of said closing portion of the retainer,
  and further comprising the steps of:
  locating said GRDF in said main portion, wherein the GRDF is in a collapsed configuration; attaching the closing portion to the main portion of the retainer;
  pressing the closing portion in the direction of the main body so that said priming member pushes said first portion of the biasing member to a position perpendicular to said second portion of the priming biasing;
  thereby priming the GRDF for administering to the patient.

The subject invention also provides a GRDF comprising a body, the body comprising at least two arms and configured to transform between a collapsed configuration for ingestion, an expanded configuration for retention within the stomach and a disassembled configuration, wherein after a predetermined time period has elapsed, the GRDF disassembles into at least two parts such that each of the disassembled parts of the GRDF is sized for exiting the stomach; an erodible insert comprising a therapeutic agent, a diagnostic agent, an electronic device, or a combination thereof; a biasing member; and at least one hinge assembly, wherein the biasing member and the at least one hinge assembly are connected by an elastic element.

The subject invention also provides a method of preparing a gastroretentive dosage form (GRDF) comprising:
  providing material for injection molding, optionally a gastric-non-erodible polymer;
  injection molding a first, a second and a third arm;
  optionally coating one or more arm(s) with a gastric-non-erodible coating;
  inserting an erodible insert comprising a therapeutic agent, a diagnostic, an electronic device, or combination thereof, into said first arm;
  connecting said first, second and third arms in the form of a triangle; and
  optionally compressing said triangular shaped system into a retainer.

The subject invention also provides a GRDF for extended retention in a human stomach, the GRDF comprising:
  a body comprising at least two arms, the body configured to transform between a collapsed configuration for ingestion, an expanded configuration for retention within the stomach and a disassembled configuration wherein after a predetermined time period has elapsed, the GRDF mechanically disassembles into at least two parts such that each of the disassembled parts of the GRDF is sized for exiting the stomach; and
  an erodible insert comprising a therapeutic agent, a diagnostic agent, an electronical device, or a combination thereof wherein the erodible insert has two opposing ends;
  wherein the GRDF further comprises a retainer surrounding the GRDF and configured to retain the GRDF in the collapsed configuration; wherein transformation of the GRDF from the collapsed configuration to the expanded configuration is induced by erosion of the retainer; wherein at least a portion of at least one arm of said at least two arms forms a sleeve, tube or shell, wherein the sleeve, tube or shell of said at least one arm comprises a cavity, the cavity housing the erodible insert; wherein said sleeve, tube or shell of said at least one arm includes at least one opening configured to allow penetration of gastric fluid into the cavity, wherein an uncoated surface area on said erodible insert overlaps with said at least one opening in said sleeve, tube or shell thereby defining at least one overlapping area which is exposed to gastric fluid; wherein erosion of the erodible insert progresses from the at least one overlapping area towards said two opposing ends of said erodible insert, and wherein the disassembled configuration of the GRDF is induced by at least 70% (w/w) erosion of said erodible insert.

The subject invention also provides an erodible insert configured to be contained in a GRDF, wherein the erodible insert comprises a therapeutic agent, a diagnostic agent, an electronical device, or a combination thereof, wherein the GRDF comprises said erodible insert and a body comprising at least two arms, the body configured to transform between a collapsed configuration for ingestion, an expanded configuration for retention within the stomach and a disassembled configuration, wherein after a predetermined time period has elapsed, the GRDF disassembles into at least two parts such that each of the disassembled parts of the GRDF is sized for exiting the stomach, wherein the disassembled configuration is induced by at least partial erosion of said erodible insert, wherein at least a portion of at least one arm of said at least two arms forms a sleeve, tube or shell, wherein said sleeve, tube or shell comprises a cavity, wherein the cavity is configured to house the erodible insert, wherein the erodible insert is contained in the cavity, wherein the erodible insert is partially coated with a gastric-non-erodible coating.

The subject invention also provides a method of delivering a therapeutic agent, a diagnostic, an electronic device, or combination thereof to the stomach of a subject for an extended period of time comprising: providing a GRDF according to the present invention, wherein at least one of the arms houses an erodible insert comprising a therapeutic agent, a diagnostic, an electronic device, or combination thereof.

The subject invention also provides a method of delivering a therapeutic agent, a diagnostic, an electronic device, or combination thereof to the stomach of a subject for an extended period of time comprising: administering a GRDF according to the present invention to a patient.

BRIEF DESCRIPTION OF THE DRAWINGS

The teachings of the present disclosure will now be described by way of example only with reference to the following drawings in which like parts are depicted by like reference numerals:

FIGS. 1A and 1B are schematic front views of a GRDF in an expanded configuration;

FIGS. 3A and 3B are simplified drawings of the GRDF of FIGS. 1A and 1B;

FIG. 5 is a simplified drawing of the transition of a GRDF from a compressed state to an expanded state;

FIGS. 12a-12c illustrate close up views of a locking mechanism of the GRDF of FIG. 10;

FIGS. 15A-15D are cross-sectional views illustrating the disassembly of the GRDF of FIG. 10;

FIGS. 16A-16C are cross-section views of alternative arrangements of a biasing element of the GRDF of FIG. 10;

FIGS. 20A-20D illustrate a method of measuring the opening force via calculation of a minimum force applied to the GRDF in the compressed state which prevents opening as well as a measure of the rigidity of structure under a compression force applied to the apex of the GRDF in the expanded state of a comparative example and the present GRDF disclosed herein;

FIG. 21A is a top (T) and bottom (B) view, FIG. 21B is a 3 dimensional side view of the sleeve with holes, and FIG. 21C presents the surface area in mm$^2$ of exposing holes R1-R5. S is small, M is medium and L is large;

Figure 1A:
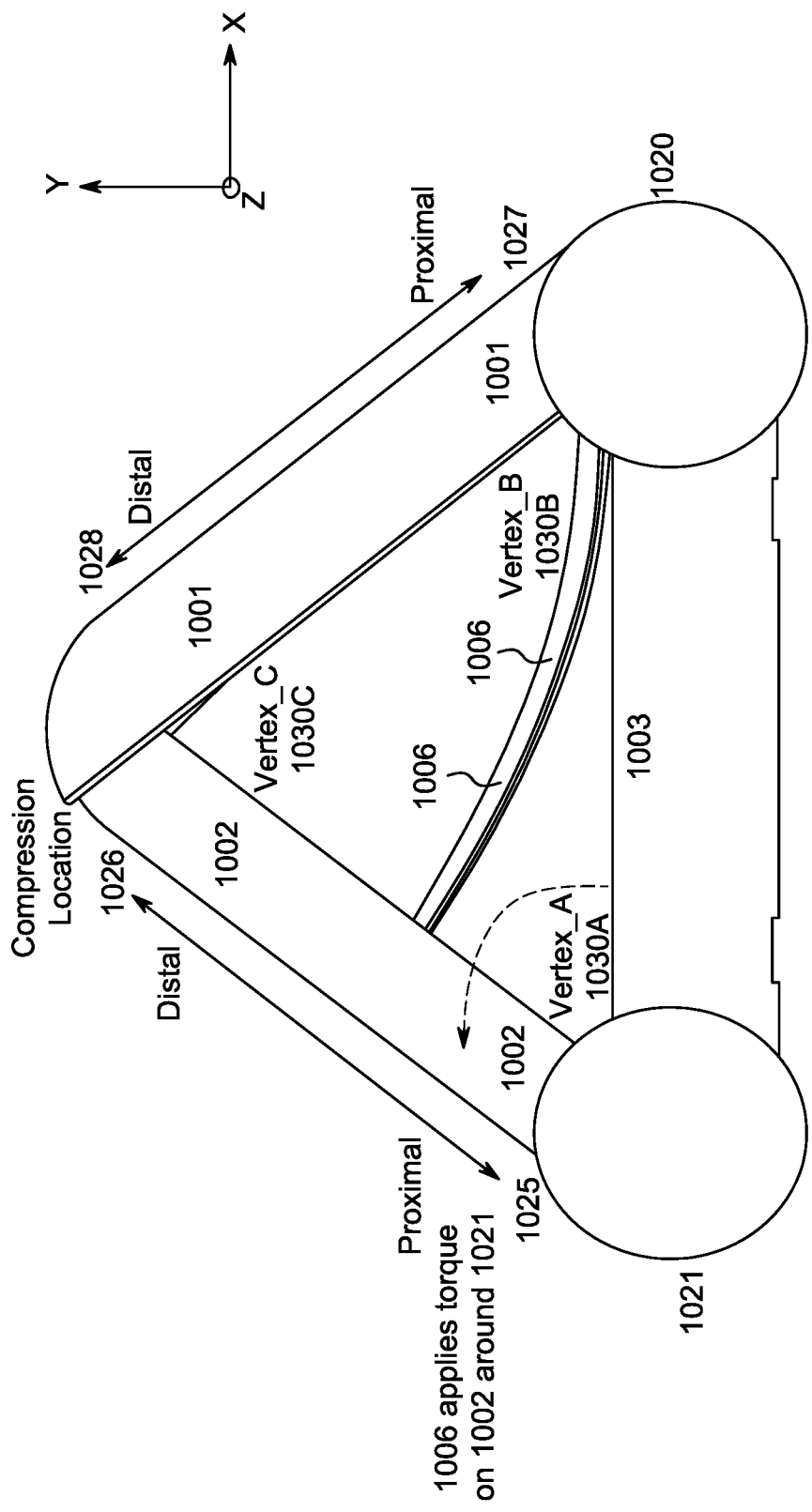

While the invention is susceptible to various modifications and alternative forms, specific embodiments are shown by way of example in the drawings and are herein described in detail. It should be understood, however, that the drawings and detailed description of the specific embodiments are not intended to limit the invention to the particular forms disclosed. On the contrary, the invention is intended to cover all modifications, equivalents and alternatives falling within the spirit and scope of the present invention as defined by the appended claims.

DETAILED DESCRIPTION

The present disclosure is in the field of gastroretentive dosage forms. A gastroretentive dosage form for extended retention in a stomach is provided.

The following numbered clauses define various aspects and features of the present invention:

1. A gastroretentive dosage form (GRDF) for extended retention in a human stomach, comprising:
   a. a body comprising at least two arms, the body configured to transform between a collapsed configuration for ingestion, an expanded configuration for retention within the stomach and a disassembled configuration wherein after a predetermined time period has elapsed, the GRDF mechanically disassembles into at least two parts such that each of the disassembled parts of the GRDF is sized for exiting the stomach; and
   b. an erodible insert comprising a therapeutic agent, a diagnostic agent, an electronical device, or a combination thereof;
   wherein the disassembled configuration is induced by at least partial erosion of the erodible insert, and wherein the GRDF is adapted to be retained in the stomach for at least 3 days, at least 4 days, at least 4.7 days, at least 5 days, at least 6 days, at least 6.6 days, at least 7 days, at least 8 days, or at least 8.3 days.
2. The GRDF according to clause 1, wherein the GRDF further comprises a retainer configured to retain the GRDF in the collapsed configuration.
3. The GRDF according to clause 2, wherein transformation of the GRDF from the collapsed configuration to the expanded configuration is induced by erosion of the retainer.
4. The GRDF according to any of clauses 2-3, wherein the retainer is selected from a capsule, a wrapper, or band surrounding the GRDF.
5. The GRDF according to any of clauses 1-4, wherein the body comprises at least three arms.
6. The GRDF according to any of clauses 1-5, wherein the body comprises three arms.
7. The GRDF according to any of clauses 1-6, wherein the body further comprises at least one hinge assembly configured to disengage from at least one arm upon at least partial erosion of the erodible insert.
8. The GRDF according to any of clauses 1-7, wherein the at least partial erosion of the erodible insert is at least 70% (w/w), at least 80% (w/w), at least 87% (w/w), at least 90% (w/w), at least 95% (w/w), at least 98% (w/w) or about 100% (w/w) erosion of the initial weight of the erodible insert.
9. The GRDF according to any of clauses 1-8, wherein at least a portion of at least one arm forms a sleeve, tube or shell.
10. The GRDF according to any of clauses 1-9, wherein at least one arm of the at least two arms forms a sleeve, tube or shell.
11. The GRDF according to any of clauses 9-10, wherein the sleeve, tube or shell comprises a cavity.
12. The GRDF according to clause 11, wherein the cavity is configured to house the erodible insert.
13. The GRDF according to clause 12, wherein the erodible insert is contained in the cavity.
14. The GRDF according to any of clauses 1-13, wherein the erodible insert is partially coated with a gastric-non-erodible coating.
15. The GRDF according to any of clauses 9-14, wherein the sleeve, tube or shell comprises at least one opening configured to allow penetration of gastric fluid into the cavity.
16. The GRDF according to any of clauses 1-15, wherein the GRDF comprises at least two arms, wherein at least a portion of at least one arm of said at least two arms forms a sleeve, tube or shell, wherein the sleeve, tube or shell of said at least one arm comprises a cavity, wherein said cavity is configured to house an erodible insert, wherein said erodible insert is housed in said cavity, wherein said sleeve, tube or shell includes at least one opening configured to allow penetration of gastric fluid into the cavity, wherein an uncoated surface area on said erodible insert overlaps with said at least one opening in said sleeve, tube or shell, thereby defining at least one overlapping area which is exposed to gastric fluid.
17. The GRDF according to clause 16, wherein a sum area of the at least one overlapping area is about 15.5 to about 59.8 mm$^2$.
18. The GRDF according to clause 16, wherein the sum area of the at least one overlapping areas is less than 59.8 mm$^2$, or less than 40.7 mm$^2$, or less than 15.5 mm$^2$.
19. The GRDF according to clause 18, wherein the sum area of the at least one overlapping area is less than 59.8 mm$^2$ and the gastric retention time is at least 4.6 days, or the sum area of the at least one overlapping area is less than 40.7 mm$^2$ and the gastric retention time is at least 6.6 days, or the sum area of the at least one overlapping area is less than 15.5 mm$^2$ and the gastric retention time is at least 8.3 days.
20. The GRDF according to any of clauses 1-19 wherein the erodible insert is an elongate erodible insert having two opposing ends.
21. The GRDF according to any of clauses 16-20, wherein the GRDF includes one overlapping area.
22. The GRDF according to clauses 16-20, wherein the GRDF includes two or more overlapping areas.
23. The GRDF according to any of clauses 16-22, wherein the at least one overlapping area is equidistant from both ends of the erodible insert or ends of the arm.
24. The GRDF according to any of clauses 16-23, wherein the at least one overlapping area is located closer to one end of the erodible insert than to the other end of the erodible insert.
25. The GRDF according to any of clauses 21-24 wherein erosion of the erodible insert progresses bidirectionally from the overlapping area to both ends of the erodible insert.
26. The GRDF according to any of clauses 1-25, wherein at least 70% (w/w), at least 80% (w/w), at least 87% (w/w), at least 90% (w/w), at least 95% (w/w), at least 98% (w/w) or about 100% (w/w) of the initial weight of the therapeutic agent is released prior to GRDF disassembly.
27. The GRDF according to any of clauses 1-26, wherein less than 20% (w/w), less than 10% (w/w), or less than 5% (w/w) of the GDRF body weight is eroded by gastric fluid or simulated gastric fluid.
28. The GRDF according to any of clauses 1-26, wherein less than 20% (w/w), less than 10% (w/w), or less than 5% (w/w) of the weight of the at least two arms and the at least one hinge assembly is eroded by gastric fluid or simulated gastric fluid.
29. The GRDF according clause 28, wherein the at least two arms and the at least one hinge assembly substantially retain their original size, shape and/or weight in the presence of gastric fluid or simulated gastric fluid.
30. The GRDF according to any of clauses 8 or 26-29, wherein % release (w/w) or % erosion (w/w) is measured using simulated gastric conditions in a rotating bottle apparatus at 37° C. at 2.5 RPM having 400 mL, pH2 and Xanthan gum 0.125 gr/L.
31. The GRDF according to any of clauses 1-30, wherein the erodible insert comprises at least 1, at least 2, at least 3, at least 4 or at least 5 tablets.
32. The GRDF according to clause 31, wherein the erodible insert consists of 1, 2, 3, 4 or 5 tablets.
33. The GRDF according to clause 32, wherein the erodible insert consists of 4 tablets or wherein the erodible insert consists of 5 tablets.
34. The GRDF according to clause 33, wherein at least one tablet comprises a therapeutic agent.
35. The GRDF according to any of clauses 31-34, wherein each tablet comprises a therapeutic agent.
36. The GRDF according to any of clauses 31-34, wherein at least one tablet comprises more than one therapeutic agent.
37. The GRDF according to any of clauses 31-36, wherein at least one tablet is at least partially coated with a gastric-non-erodible coating.
38. The GRDF according to clause 37, wherein each tablet is at least partially coated with a gastric-non-erodible coating.
39. The GRDF according to any of clauses 1-38, wherein the erodible insert comprises more than one therapeutic agent.
40. The GRDF according to any of clauses 1-39, wherein the erodible insert is not fastened to the body of the GRDF by a physical measure selected from gluing or tethering.
41. The GRDF according to any of clauses 1-40, wherein the erodible insert is not fastened to the at least two arms by a physical measure selected from gluing or tethering.
42. The GRDF according to any of clauses 1-41, wherein the at least two arms and/or the at least one hinge assembly do not comprise an elastomer.
43. The GRDF according to any of clauses 1-42, wherein the at least two arms and/or the at least one hinge assembly are coated with a gastric-non-erodible coating.
44. The GRDF according to any of clauses 1-43, wherein the body consists of gastric-non-erodible materials.
45. The GRDF according to any of clauses 1-43, wherein the at least two arms and/or the at least one hinge assembly consists of gastric-non-erodible material.
46. The GRDF according to any of clauses 44-45, wherein the gastric-non-erodible materials are at least one gastric-non-erodible polymer.
47. The GRDF according to clause 46, wherein the at least one gastric-non-erodible polymer is cellulose ester.
48. The GRDF according to clause 47, wherein the cellulose ester is selected from cellulose acetate, cellulose butyrate, or a combination thereof.
49. The GRDF according to any of clauses 1-48, wherein the body is composed of material that does not comprise a therapeutic agent.
50. The GRDF according to any of clauses 1-48, wherein the body is composed of material that is not eroded in gastric fluid or simulated gastric fluid, or at GRDF disassembly.
51. The GRDF according to any of clauses 1-48, wherein the at least two arms and the at least one hinge assembly are composed of material that does not erode in gastric fluid or simulated gastric fluid, or at GRDF disassembly.
52. The GRDF according to any of clauses 1-51, wherein the erodible insert is configured to erode upon contact with gastric fluid or simulated gastric fluid.
53. The GRDF according to clause 52, wherein erosion of the erodible insert is configured to release the therapeutic agent, diagnostic agent, electronic device or combination thereof into the gastric fluid.

54. The GRDF according to any of clauses 1-53, wherein the at least two arms comprise a first arm, a second arm and a third arm.
55. The GRDF according to clause 54, the first arm comprising a first end and a second opposing end, the second and third arms being pivotally connected to the first end and the second end of the first arm, respectively.
56. The GRDF according to any of clauses 54-55, comprising a biasing member configured to bias the GRDF into the expanded configuration, wherein in the expanded configuration, the second and third arms are configured to mechanically engage each other to retain the GRDF in the expanded configuration.
57. The GRDF according to any of clauses 54-56, wherein a portion of the second arm distal to the first arm and a portion of the third arm distal to the first arm are configured to mechanically engage each other in the expanded configuration.
58. The GRDF according to any of clauses 54-57, wherein the third arm comprises a retaining surface against which the second arm engages when the GRDF is in the expanded configuration.
59. The GRDF according to any of clauses 54-58, wherein the third arm comprises a protrusion against which the second arm engages when the GRDF is in the expanded configuration.
60. The GRDF according to clause 59, wherein the protrusion is provided at an opposite end of the third arm to the first arm and wherein in the expanded configuration, the end of the second arm distal to the first arm engages with the protrusion to form an apex.
61. The GRDF according to any of clauses 54-60, wherein during transformation from the collapsed configuration to the expanded configuration, an outer surface of the second arm is configured to slide along the third arm.
62. The GRDF according to any of clauses 54-61, wherein the third arm comprises an elongate protrusion along its length and the second arm comprises a recess configured to cooperate with the elongate protrusion during transformation from the collapsed configuration to the expanded configuration.
63. The GRDF according to any of clauses 54-62, wherein in the expanded configuration the first, second and third arms are configured to form a generally triangular shape.
64. The GRDF according to clause 63, wherein a smallest turning radius of the triangular shape is between 20 and 35 mm.
65. The GRDF according to any of clauses 54-64, wherein in the collapsed configuration, the second arm is configured to overlay the first arm and the third arm is configured to overlay the second arm.
66. The GRDF according to any of clauses 54-65, wherein the second and third arms are shaped such that an inner surface of the third arm has a corresponding shape to an outer surface of the second arm and an inner surface of the second arm has a corresponding shape to an outer surface of the first arm.
67. The GRDF according to any of clauses 56-66, wherein the biasing member comprises an elongate member configured to bias the second arm.
68. The GRDF according to any of clauses 56-67, wherein the second arm comprises a recess or protrusion configured to engage a portion of the biasing member when the GRDF is in the expanded configuration.
69. The GRDF according to any of clauses 56-68, wherein the biasing member comprises at least one of an elastic leaf spring, a helical spring attached to a rigid member and a superporous hydrogel.
70. The GRDF according to any of clauses 54-69, wherein after a predetermined time period in the expanded configuration, the GRDF is configured to mechanically disassemble.
71. The GRDF according to clause 70, wherein the mechanical disassembly of the GRDF comprises disconnection of the second and/or third arms from the first arm.
72. The GRDF according to clause 71, wherein upon disconnection of the second and/or third arms from the first arm, the second and third arms are configured to disconnect from each other.
73. A mechanism for priming of a GRDF for administering to a patient, the GRDF comprising:
    a) a body including at least two arms, the body configured to transform between a collapsed configuration for ingestion, an expanded configuration for retention within the stomach and a disassembled configuration, wherein after a predetermined time period has elapsed, the GRDF disassembles into at least two parts such that each of the disassembled parts of the GRDF is sized for exiting the stomach,
    b) an erodible insert comprising a therapeutic agent, a diagnostic agent, an electronical device, or a combination thereof
    c) a biasing member having a first portion and a second portion;
    d) a retainer configured to house the GRDF for ingestion, wherein the retainer has a main portion and a closing portion, wherein the retainer is configured to retain the GRDF in the collapsed configuration; and
    e) a priming member extending from an interior side of said closing portion of the retainer, and further comprising the steps of:
        i. locating said GRDF in said main portion, wherein the GRDF is in a collapsed configuration;
        ii. attaching the closing portion to the main portion of the retainer;
        iii. pressing the closing portion in the direction of the main body so that said priming member pushes said first portion of the biasing member to a position perpendicular to said second portion of the priming biasing;
        thereby priming the GRDF for administering to the patient.
74. The mechanism according to clause 73, wherein the GRDF further comprises a retaining element configured to retain the biasing member in a primed state until dissolution of the retainer.
75. The mechanism according to clauses 73-74, wherein the retainer is a capsule, a wrapper, or band surrounding the GRDF.
76. A GRDF comprising a body, the body comprising at least two arms and configured to transform between a collapsed configuration for ingestion, an expanded configuration for retention within the stomach and a disassembled configuration, wherein after a predetermined time period has elapsed, the GRDF disassembles into at least two parts such that each of the disassembled parts of the GRDF is sized for exiting the stomach; an erodible insert comprising a therapeutic agent, a diagnostic agent, an electronical device, or a combination thereof; a biasing member; and at least one hinge assembly, wherein the biasing member and the at least one hinge assembly are connected by an elastic element.

77. The GRDF according to clause 76, wherein the elastic element is stretched when the GRDF is maintained in a collapsed configuration.

78. The GRDF according to clause 77, wherein the elastic element maintains its elastic properties with minimal to no plastic deformation for at least 2 months, at least 4 months, at least one year or at least 2 years.

79. The GRDF according to any of clauses 76-78, wherein the elastic element comprises, or consists of, silicone rubber.

80. The GRDF according to any of clauses 76-79, wherein the elastic element has a minimal tensile strength of 8.5 GPa and minimal elongation of 500% as tested in ASTM D412.

81. The GRDF according to clause 80, wherein the elastic element further has hardness of 40-shore A as tested in a D2240 ASTM test.

82. The GRDF according to any of clauses 1-72 or 76-81, wherein % release (w/w) of API out of the total initial API (w/w) per day as measured over at least 3 days is about 10% to 25% (w/w), or about 12% to 22% (w/w), or less than about 30% (w/w), or less than about 25% (w/w), or less than about 20% (w/w), or less than about 15% (w/w), or about 12% (w/w), as measured in vitro in a rotating bottle apparatus at 37° C. at 2.5 RPM having 400 mL, pH2 and Xanthan gum 0.125 gr/L.

83. The GRDF according to any of clauses 1-72 or 76-82, wherein % RSD of the % release (w/w) of API out of the total API weight per day as measured over at least 3 days is about 76%, or about 65%, or about 31%, or less than about 80%, or less than about 70% or less than about 50% or less than about 40% or less than about 35%, as measured in vitro in a rotating bottle apparatus at 37° C. at 2.5 RPM having 400 mL, pH2 and Xanthan gum 84. The GRDF according to any of clauses 1-72 or 76-83 wherein the erodible insert comprises an extended-release excipient.

85. GRDF according to clause 84, wherein the extended-release excipient is methylcellulose, methocel or a combination thereof.

86. A method of preparing a gastroretentive dosage form (GRDF) comprising:
   a. providing material for injection molding, optionally a gastric-non-erodible polymer;
   b. injection molding a first, a second and a third arm;
   c. optionally coating one or more arm(s) with a gastric-non-erodible coating;
   d. inserting an erodible insert comprising a therapeutic agent, a diagnostic, an electronic device, or combination thereof, into said first arm;
   e. connecting said first, second and third arms in the form of a triangle; and
   f. optionally compressing said triangular shaped system into a retainer.

87. The method according to clause 86, further comprising:
   a. injection molding a first and a second hinge assembly;
   b. connecting the first arm to the second arm by said first hinge assembly, and connecting the first arm to the third arm by said second hinge assembly;
   c. injection molding a biasing member;
   d. connecting one of said first hinge assembly and said second hinge assembly to said biasing member by an elastic element.

88. The method according to clause 87, wherein the elastic element is stretched when the GRDF is maintained in the compressed configuration.

89. The method according to clause 88, wherein the elastic element maintains its elastic properties with minimal to no plastic deformation for at least 2 months, at least 4 months, at least one year or at least 2 years.

90. The method according to any of clauses 87-89, wherein the elastic element comprises, or is made of, silicone rubber.

91. The method according to any of clauses 87-90, wherein the elastic element has a minimal tensile strength of 8.5 GPa and minimal elongation of 500% as tested in ASTM D412.

92. The method according to clause 91, wherein the elastic element further has hardness of 40-shore A as tested in a D2240 ASTM test.

93. The method according to any one of clauses 86-92, wherein all the materials are pharmaceutically acceptable.

94. A GRDF for extended retention in a human stomach, the GRDF comprising:
   a. a body comprising at least two arms, the body configured to transform between a collapsed configuration for ingestion, an expanded configuration for retention within the stomach and a disassembled configuration wherein after a predetermined time period has elapsed, the GRDF mechanically disassembles into at least two parts such that each of the disassembled parts of the GRDF is sized for exiting the stomach; and
   b. an erodible insert comprising a therapeutic agent, a diagnostic agent, an electronical device, or a combination thereof wherein the erodible insert has two opposing ends;
   wherein the GRDF further comprises a retainer surrounding the GRDF and configured to retain the GRDF in the collapsed configuration; wherein transformation of the GRDF from the collapsed configuration to the expanded configuration is induced by erosion of the retainer; wherein at least a portion of at least one arm of said at least two arms forms a sleeve, tube or shell, wherein the sleeve, tube or shell of said at least one arm comprises a cavity, the cavity housing the erodible insert; wherein said sleeve, tube or shell of said at least one arm includes at least one opening configured to allow penetration of gastric fluid into the cavity, wherein an uncoated surface area on said erodible insert overlaps with said at least one opening in said sleeve, tube or shell thereby defining at least one overlapping area which is exposed to gastric fluid; wherein erosion of the erodible insert progresses from the at least one overlapping area towards said two opposing ends of said erodible insert, and wherein the disassembled configuration of the GRDF is induced by at least 70% (w/w) erosion of said erodible insert.

95. The GRDF according to clause 94, wherein the disassembled configuration of the GRDF is induced by at least 80% (w/w) erosion of the erodible insert, by at least 87% (w/w) erosion of the erodible insert, by at least 95% (w/w) erosion of the erodible insert, by at least 98% erosion of the erodible insert or by about 100% (w/w) erosion of the erodible insert.

96. The GRDF according to any of clauses 94-95, wherein the GRDF further comprises a biasing member and at least one hinge assembly, wherein the biasing member and the at least one hinge assembly are connected by an elastic element.
97. The GRDF according to clause 96, wherein the elastic element is stretched when the GRDF is maintained in the compressed configuration.
98. The GRDF according to clause 97, wherein the elastic element maintains its elastic properties with minimal to no plastic deformation for at least 2 months, at least 4 months, at least one year or at least 2 years.
99. The GRDF according to any of clauses 96-98, wherein the elastic element comprises, or is made of, silicone rubber.
100. The GRDF according to any of clauses 96-99, wherein the elastic element has a minimal tensile strength of 8.5 GPa and minimal elongation of 500% as tested in ASTM D412.
101. The GRDF according to clause 100, wherein the elastic element further has hardness of shore A as tested in a D2240 ASTM test.
102. The GRDF according to any of clauses 96-101, wherein all the materials are pharmaceutically acceptable.
103. The GRDF according to any of clauses 94-95, wherein the GRDF is primed for administering to a patient using a mechanism comprising:
    a. a body including at least two arms, the body configured to transform between a collapsed configuration for ingestion, an expanded configuration for retention within the stomach and a disassembled configuration, wherein after a predetermined time period has elapsed, the GRDF mechanically disassembles into at least two parts such that each of the disassembled parts of the GRDF is sized for exiting the stomach,
    b. an erodible insert comprising a therapeutic agent, a diagnostic agent, an electronical device, or a combination thereof;
    c. a biasing member having a first portion and a second portion;
    d. a retainer configured to house the GRDF for ingestion, wherein the retainer has a main portion and a closing portion, wherein the retainer is configured to retain the GRDF in the collapsed configuration; and
    e. a priming member extending from an interior side of said closing portion of the retainer,
    and further comprising the steps of:
      i. locating said GRDF in said main portion, wherein the GRDF is in a collapsed configuration;
      ii. attaching the closing portion to the main portion of the retainer;
      iii. pressing the closing portion in the direction of the main body so that said priming member pushes said first portion of the biasing member to a position perpendicular to said second portion of the priming biasing;
      thereby priming the GRDF for administering to the patient.
104. The GRDF according to clause 103, wherein the GRDF further comprises a retaining element configured to retain the biasing member in a primed state until dissolution of the retainer.
105. The GRDF according to any of clauses 103-104, wherein the retainer is a capsule, a wrapper, or band surrounding the GRDF.
106. An erodible insert configured to be contained in a GRDF, wherein the erodible insert comprises a therapeutic agent, a diagnostic agent, an electronical device, or a combination thereof, wherein the GRDF comprises said erodible insert and a body comprising at least two arms, the body configured to transform between a collapsed configuration for ingestion, an expanded configuration for retention within the stomach and a disassembled configuration, wherein after a predetermined time period has elapsed, the GRDF disassembles into at least two parts such that each of the disassembled parts of the GRDF is sized for exiting the stomach, wherein the disassembled configuration is induced by at least partial erosion of said erodible insert, wherein at least a portion of at least one arm of said at least two arms forms a sleeve, tube or shell, wherein said sleeve, tube or shell comprises a cavity, wherein the cavity is configured to house the erodible insert, wherein the erodible insert is contained in the cavity, wherein the erodible insert is partially coated with a gastric-non-erodible coating.
107. The GRDF according to any of clauses 82-83 and 94-95 wherein % release (w/w) or erosion (w/w) is measured using simulated gastric conditions in a rotating bottle apparatus at 37° C. at 2.5 RPM having 400 mL, pH2 and Xanthan gum 0.125 gr/L.
108. A method of delivering a therapeutic agent, a diagnostic, an electronic device, or combination thereof to the stomach of a subject for an extended period of time comprising: providing a GRDF according to any of clauses 1-72, 83-85 or 94-105, wherein at least one of the arms houses an erodible insert comprising a therapeutic agent, a diagnostic, an electronic device, or combination thereof.
109. A method of delivering a therapeutic agent, a diagnostic, an electronic device, or combination thereof to the stomach of a subject for an extended period of time comprising: administering a GRDF according to any of clauses 1-72, 83-85 or 94-105, to a patient.
110. The GRDF according to any of clauses 7-72 or 83-85 wherein each of the at least two parts comprises at least one arm and/or at least one hinge assembly.
111. The GRDF according to any of clauses 94-105 wherein the body further comprise at least one hinge assembly and wherein each of the at least two parts comprises at least one arm and/or at least one hinge assembly.
112. A gastroretentive dosage form (GRDF) for extended retention in a human stomach, comprising:
    c. a body comprising at least two arms, the body configured to transform between a collapsed configuration for ingestion, an expanded configuration for retention within the stomach and a disassembled configuration wherein after a predetermined time period has elapsed, the GRDF mechanically disassembles into at least two parts such that each of the disassembled parts of the GRDF is sized for exiting the stomach, wherein the body further comprises at least one hinge assembly and wherein each of said at least two parts comprises at least one arm and/or at least one hinge assembly; and
    d. an erodible insert comprising a therapeutic agent, a diagnostic agent, an electronical device, or a combination thereof;
    wherein the disassembled configuration is induced by at least partial erosion of the erodible insert, and wherein the GRDF is adapted to be retained in the stomach for at least 3 days, at least 4 days, at least 4.7 days, at least 5 days, at least 6 days, at least 6.6 days, at least 7 days, at least 8 days, or at least 8.3 days.

113. A GRDF for extended retention in a human stomach, the GRDF comprising:
   a. a body comprising at least two arms, the body configured to transform between a collapsed configuration for ingestion, an expanded configuration for retention within the stomach and a disassembled configuration wherein after a predetermined time period has elapsed, the GRDF mechanically disassembles into at least two parts such that each of the disassembled parts of the GRDF is sized for exiting the stomach, wherein the body further comprises at least one hinge assembly and wherein each of said at least two parts comprises at least one arm and/or at least one hinge assembly; and
   b. an erodible insert comprising a therapeutic agent, a diagnostic agent, an electronical device, or a combination thereof wherein the erodible insert has two opposing ends;
   wherein the GRDF further comprises a retainer surrounding the GRDF and configured to retain the GRDF in the collapsed configuration; wherein transformation of the GRDF from the collapsed configuration to the expanded configuration is induced by erosion of the retainer; wherein at least a portion of at least one arm of said at least two arms forms a sleeve, tube or shell, wherein the sleeve, tube or shell of said at least one arm comprises a cavity, the cavity housing the erodible insert; wherein said sleeve, tube or shell of said at least one arm includes at least one opening configured to allow penetration of gastric fluid into the cavity, wherein an uncoated surface area on said erodible insert overlaps with said at least one opening in said sleeve, tube or shell thereby defining at least one overlapping area which is exposed to gastric fluid; wherein erosion of the erodible insert progresses from the at least one overlapping area towards said two opposing ends of said erodible insert, and wherein the disassembled configuration of the GRDF is induced by at least 70% (w/w) erosion of said erodible insert.

114. The GRDF according to clause 113, wherein the disassembled configuration of the GRDF is induced by at least 80% (w/w) erosion of the erodible insert, by at least 87% (w/w) erosion of the erodible insert, by at least 95% (w/w) erosion of the erodible insert, by at least 98% (w/w) erosion of the erodible insert or by about 100% (w/w) erosion of the erodible insert.

115. The mechanism for priming or the GRDF according to any of the previous clauses, wherein the GRDF disassembly into the at least two parts is a mechanical disassembly.

Definitions

The wording herein below is implied in the common meaning of the definitions and statements as known to those skilled in the art. However, there are several terms that should be understood in the concept of the present disclosure as follows:

As use herein, "gastric-non-erodible" or "gastric non-degradable" or "gastric-fluid-insoluble" coating means a coating which does not degrade, dissolve or disintegrate in the gastric environment. Such coating, when applied onto e.g. parts of a GRDF, obviates or reduces their dissolution or disintegration in the gastric environment. In an embodiment, the gastric-non-erodible coating is an enteric coating. In an embodiment, the body of the GRDF of the present invention is at least partially coated by a gastric-non-erodible coating. In an embodiment, at least two arms of the GRDF of the present invention are at least partially coated by a gastric-non-erodible coating. In a further embodiment, three arms of the GRDF of the present invention and the hinge assemblies are at least partially coated by a gastric-non-erodible coating. In a further embodiment, the erodible insert of the present invention is at least partially coated by a gastric-non-erodible coating. In a further embodiment, at least one tablet out of the tablets forming the erodible insert of the present invention is at least partially coated by a gastric-non-erodible coating. In a further embodiment, all the tablets forming the erodible insert of the present invention are at least partially coated by a gastric-non-erodible coating. The erodible insert may comprise one or more tablets; for example, 2, 3, 4, 5, 6, 7, 8 or more tablets. The tablets may be arranged side-by-side inside the shell, tube or sleeve in at least one arm of the GRDF. For example there may be two side tablets, each one positioned at a distal end of the shell, tube or sleeve, and one or more central tablets. In an embodiment, only side tablets (e.g. tablets which are positioned at a distal end of the shell, tube or sleeve, e.g. adjacent to the hinge assembly) are at least partially coated by a gastric-non-erodible coating. As used herein, "an uncoated area" of the erodible insert or "an uncoated surface" on the erodible insert or "an uncoated area on the surface of the erodible insert" means an area on the surface of the erodible insert which is not covered by a gastric-non-erodible coating. In an embodiment, at least one uncoated area of the erodible insert overlaps, or faces, at least one opening in the sleeve of an arm housing the erodible insert, thus creating "an overlapping area/s" which is/are exposed to gastric fluid. In an embodiment, the erodible insert is exclusively exposed to gastric fluid at the overlapping area/s. In an embodiment, the gastric-non-erodible coating comprises at least one gastric-non-erodible polymer.

As used herein, "percent release" (% release) of the API or diagnostic agent is the percent amount of the API or diagnostic agent that is released into the gastric fluid in the stomach or in simulated gastric conditions (e.g. a rotating bottle apparatus at 37° C. at 2.5 RPM having 400 mL, pH2 and Xanthan gum 0.125 gr/L) out of the initial amount of the API or diagnostic agent in the composition. The percent release at the time point of measurement (e.g. at GRDF disassembly) may be calculated as "% release of the API (weight/w weight=w/w)" which is the percent weight of the API or diagnostic agent that has been released into the fluid, out of the initial weight of the API or diagnostic agent in the composition. This may be calculated as follows:
   Calculating the weight of the API or diagnostic agent that has been released to the fluid, e.g. in a rotating bottle apparatus at 37° C. at 2.5 RPM having 400 mL, pH2 and Xanthan gum 0.125 gr/L (for example by measuring the concentration of the API or the diagnostic agent in the fluid, measured e.g. using HPLC, and multiplying by the fluid volume);
   dividing the calculated released weight by the initial weight of the API or diagnostic agent in the erodible insert composition; and
   further multiplying the quotient by 100.

As used herein, "percent erosion" (% erosion) of the erodible insert is the percent amount of the erodible insert composition that is released into the gastric fluid in the stomach or in simulated gastric conditions (e.g. a rotating bottle apparatus at 37° C. at 2.5 RPM having 400 mL, pH2 and Xanthan gum 0.125 gr/L). The percent erosion at the time point of measurement (e.g. at GRDF disassembly) may be calculated as "% erosion (weight/w weight=w/w)" of the erodible insert, which is the percent weight of the erodible insert composition that is dissolved into the gastric fluid in the stomach or in simulated gastric conditions (e.g. a rotating bottle apparatus at 37° C. at 2.5 RPM having 400 mL, pH2 and Xanthan gum 0.125 gr/L) out of the initial weight of the erodible insert composition. This may be calculated as follows:

Subtracting from the initial weight of the erodible insert (including excipients and API, diagnostic agent or combination thereof, and excluding coating if present) the weight of the erodible insert at the time point of measurement (including excipients and API, diagnostic agent or combination thereof, and excluding coating if present), measured e.g. in a rotating bottle apparatus at 37° C. at 2.5 RPM having 400 mL, pH2 and Xanthan gum 0.125 gr/L;

dividing the difference by the initial weight of the erodible insert (including excipients and API, diagnostic agent or combination thereof, and excluding coating if present); and further multiplying the quotient by 100.

In an embodiment, erosion of the erodible insert is synchronized with the % release of the API or diagnostic agent (e.g. if the dispersion of API or diagnostic agent in the erodible is generally homogenous). According to this embodiment, % erosion of the erodible insert is correlated, similar or preferably very similar to the calculated % release of the API or diagnostic agent.

To note, other ways to evaluate or quantify the size, shape and/or weight of the erodible insert at the time of measurement include but are not limited to: barium labelling identified using X-ray, scintigraphy, weight loss after drying, and visual observation.

As used herein, an "erodible insert" is any formulation, composition, e.g. in the form of a tablet, tablets or extrudate, which is contained in the body of the GRDF, and which is capable of degradation, dissolution, and/or disintegration based on exposure to gastric environment or simulated methods thereof. In an embodiment, an "erodible insert" is located inside the sleeve, tube or shell of an arm of the GRDF, e.g. in a cavity inside the sleeve, tube or shell of an arm of the GRDF. In an embodiment, the erodible insert comprises a therapeutic agent, a diagnostic agent, an electronical device, or a combination thereof. In an embodiment, API dispersion in the erodible insert is not homogenous. In a preferred embodiment, the API is homogenously dispersed in the formulation forming the erodible insert. Preferably, only a portion of the erodible insert is exposed to the gastric environment. In an embodiment, the erodible insert is partially coated by a gastric-non-erodible coating. To clarify, the dissolution profile of the "erodible insert", e.g. in the form of a tablet, tablets or extrudate, may be evaluated outside of the human or animal body, e.g. by simulated methods (e.g. simulated gastric conditions, e.g. a rotating bottle apparatus at 37° C. at 2.5 RPM having 400 mL, pH2 and Xanthan gum 0.125 gr/L). In an embodiment, the erodible insert comprises at least 1, at least 2, at least 3, at least 4 or at least 5 tablets. In an embodiment, the erodible insert consists of 1, 2, 3, 4 or 5 tablets. In an embodiment, the erodible insert consists of 4 tablets. In an embodiment, the erodible insert consists of 5 tablets. In an embodiment, at least one tablet comprises a therapeutic agent. In an embodiment, each tablet comprises a therapeutic agent. In an embodiment, at least one tablet comprises more than one therapeutic agent. In an embodiment, at least one tablet is at least partially coated with a gastric-non-erodible coating. In an embodiment, each tablet is at least partially coated with a gastric-non-erodible coating. In an embodiment, the erodible insert comprises more than one therapeutic agent. In an embodiment, the erodible insert is not fastened to the body of the GRDF by a physical measure selected from gluing or tethering. In an embodiment, the erodible insert is not fastened to the at least two arms by a physical measure selected from gluing or tethering.

As used herein, a "gastric-erodible", "gastric-degradable" or "gastric-fluid-soluble" material, e.g. polymer includes any material e.g. polymer that degrades, dissolves or disintegrates in the gastric environment. As used herein, a "gastric-non-erodible", "gastric-non-degradable" or "gastric-fluid-insoluble" material, e.g. polymer, includes any material, e.g. polymer that does not degrade, dissolve or disintegrate in the gastric environment.

"Gastric retention", extended gastric retention", or "extended retention in the stomach" (e.g. in the human stomach), as used herein is the maintenance or holding of an agent, for example at least one therapeutic agent, diagnostic agent, electronic device or combination thereof in the stomach for a time period longer than the time it would have been retained in the stomach when delivered in a free form or within a delivery vehicle which is not considered gastroretentive. Gastric retentivity may be characterized by retention in the stomach for a period that is longer than the normal emptying time from the stomach, such as longer than about 24 hours, 48, 72, 96, 120, 144, 168 hr or longer. In an embodiment, "gastric retention" or "extended retention" in the stomach refers to retention in the stomach of a subject for a period that is at least 3 days, at least 4 days, at least 4.7 days, at least 5 days, at least 6 days, at least 6.6 days, at least 7 days, at least 8 days, or at least 8.3 days or longer.

"Gastroretentive dosage form(s)" (GRDF or GRDFs in the plural) refers to dosage forms which reside in the confines of a stomach of a subject for the purpose of providing a platform for the gastric retention of therapeutic agents, diagnostic agents and/or electronic devices in the stomach. In an embodiment, the GRDF of the present invention is capable of gastric retention. In an embodiment, the GRDF of the present invention includes at least a body and an erodible insert comprising at least one therapeutic agent, diagnostic agent, electronic device or combination thereof. In an embodiment, the GRDF of the present invention consists of a body and an erodible insert comprising at least one therapeutic agent, diagnostic agent, electronic device or combination thereof. In a preferred embodiment, at least one therapeutic agent, diagnostic agent, electronic device or combination thereof are contained in an erodible insert present in at least one arm of the GRDF. In an embodiment, the GRDF of the present invention provides gastric retention of the at least one therapeutic agent, diagnostic agent, electronic device or combination thereof which are comprised in the erodible insert.

"Gastric residence system", "gastroretentive delivery system" or "GRS" as used herein refer to a GRDF.

As used herein, a size "suitable for swallowing" is any size and/or shape that are capable of being safely swallowed by a human. Unless specified otherwise, size for retention or reference to anatomy such as stomach or pyloric valve are in reference a human.

As used herein, a "body" is meant to include any collection of parts or materials that are more or less constrained or otherwise connected to move together by translation or rotation. The "body" of the GRDF of the present invention includes all parts of the GRDF excluding the erodible insert. At the very least, the body of the GRDF disclosed herein comprises two arms. In an embodiment, the body of the GRDF of the present invention comprises at least two arms and at least on hinge assembly. In a preferred embodiment, the body of the GRDF of the present invention comprises at least three arms, two hinge assemblies and a biasing member. In a preferred embodiment, the body of the GRDF of the present invention comprises materials, e.g. polymers, which are non-erodible under gastric conditions, including but not limited to cellulose esters such as cellulose acetate and cellulose butyrate. In a preferred embodiment, the body of the GRDF of the present invention consists of materials, e.g. polymers, which are non-erodible under gastric conditions, including but not limited to cellulose esters such as cellulose acetate and cellulose butyrate. In an embodiment, the body of the GRDF of the present invention is at least partially covered by a gastric-non-erodible coating, e.g. enteric coating, protecting it from erosion under gastric conditions.

As used herein, "excipient" refers to an ingredient, or mixture of ingredients, that is used in the formulation of the compositions (including but not limited to the insert, the body parts—arm, etc.) of the present disclosure to give desirable characteristics to the composition or erodible insert. As used herein, the term "pharmaceutically acceptable" refers to those compounds, materials, compositions, compacts, salts, and/or dosage forms which are, within the scope of sound medical judgment, suitable for contact with the tissues of human beings and animals without excessive toxicity, irritation, allergic response, or other problematic complications over the desired duration of treatment commensurate with a reasonable benefit/risk ratio. In some embodiments, the term "pharmaceutically acceptable" means approved by a regulatory agency of the Federal or a state government, such as the Inactive Ingredient Database of the FDA or listed in the U.S. Pharmacopeia or other generally recognized international pharmacopeia for use in animals, and more particularly in humans. Various pharmaceutically acceptable excipients can be used. In some embodiments, the pharmaceutically acceptable excipient can be, but is not limited to, an alkaline agent, a stabilizer, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, Remington: The Science and Practice of Pharmacy, 21st ed. (2005). Inclusion of an excipient in a particular classification herein (e.g., "solvent") is intended to illustrate rather than limit the role of the excipient. A particular excipient can fall within multiple classifications.

As used herein, "pharmaceutical", "active", "an active pharmaceutical ingredient (API)", "therapeutic agent" or "active agent" is meant to include any agent that is administered to a subject to treat a disease, disorder, or other clinically recognized condition, or for prophylactic purposes, and has a clinically significant effect on the body of the subject to treat and/or prevent the disease, disorder, or condition. Active pharmaceutical ingredients (APIs) may include but are not limited to the following: prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, bismuth salts, colchicine, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, metformin, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, 4-aminopyridine tobutamide, chlorproamide, tolazamide, acetohexamide, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-norprogesterone, norgestrel, norethindrone, norethisterone, norethiederone, progesterone, norgesterone, norethynodrel, terfenadine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, carbidopa, selegiline, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents. Further examples are proteins and peptides which include, but are not limited to, cyclosporine such as cyclosporine A, insulin, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor. Listings of additional examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. In certain embodiments, the therapeutic agent may include one or more therapeutic agents. The erodible insert may hold two or more therapeutic agents which may be presented as separate components or may be admixed and presented together in a single form, for example, tablet.

A wide variety of APIs may be employed in accordance with the aspects of the present disclosure. Relevant APIs are not limited to, but may include the following: APIs acting locally in the stomach; APIs primarily absorbed in the stomach; APIs poorly soluble in alkaline pH; APIs with narrow windows of absorption; APIs with poor patient adherence; APIs absorbed rapidly from the GI tract; APIs that degrade in the colon; and APIs that disturb colonic microbes. In addition, "diagnostics" or "a diagnostic agent" which may be employed in accordance with the aspects of the present disclosure include but are not limited to medical imaging systems (e.g. scanner, MRI, camera, gastric stimulator, radiolabeled agents and the like. Electronic devices which may be employed in accordance with the aspects of the present disclosure include but are not limited to microchips, imaging systems, transmitters and the like.

As used herein, "gastric retentive endpoint" may be dependent on a "time dependent disassembly mechanism" or "timed disassembly" or "timed downsizing" wherein the GRDF loses its mechanical integrity by "mechanical disassembly", through a mechanical event exemplified by: cleaving a connection between a first arm and another arm or pivotal connection thereof for example a hinge assembly.

As used herein, "mechanical disassembly" or "GRDF disassembly" or "disassembly of the GRDF" refers to the disengagement of the GRDF into at least two parts, wherein the parts of the body of the GRDF comprised in each part of the at least two parts substantially retain their original size, shape and/or weight. Mechanical disassembly may result e.g. from the erosion of the erodible insert, leading to disengagement of least one hinge assembly hinge assembly from at least one arm. To clarify, the mechanical disassembly, or GRDF disassembly excludes disassembly into at least two parts wherein at least one part consists of the erodible insert. Rather, each of the at least two parts resulting from mechanical disassembly includes at least one arm and/or at least one hinge assembly.

As used herein, "pharmaceutical-releasing" is meant to include any formulation which is designed to undergo degradation, dissolution, disintegration etc. when exposed to the gastric environment, resulting in release of API. Pharmaceutical formulations can include one or more therapeutic agents or active pharmaceutical ingredients.

As used herein, the "retainer", "erodible wrapper" or "gastric-fluid-erodible wrapper" refers to any standard means for packaging pharmaceuticals for delivery into the stomach, such as capsules. The means may erode, dissolve and/or disintegrate within minutes of reaching the gastric environment.

As used herein, the term "arm" or "arms" includes any structure that includes a length, width and thickness and aids in achieving a device of a size suitable for gastric retention. In some embodiments, the length of each arm may be about at least 1.5 or at least 2.0 or at least 2.5 or about 2.5 to about 3.0 or at most 3.0 or at most 2.8 or at most 2.7 or at most 2.6. At least one arm of the GRDF as described herein retains an active pharmaceutical, diagnostic, electronic device etc. For example, the at least one arm may define a cavity therein configured to retain an erodible insert.

As used herein, the term "hinge assembly" includes any mechanism adapted to permit relative pivotal movement between two or more structures, e.g., arms. The hinge assembly may be consist of one integral part (e.g., a living hinge) or one or more parts that are assembled in the conventional sense. The hinge assembly may attach to one or more arms in both the collapsed and expanded configurations. The hinge assembly may be capable of, at a predetermined time or upon occurrence of a mechanical event, disengaging from the one or more arms. In an embodiment of the present disclosure, the hinge assembly disengages from at least one arm as a result of the erosion of the erodible insert. In a preferred embodiment, the hinge assembly disengages from the at least one arm as a result of the erosion of the erodible insert, wherein the hinge assembly substantially retains its original size, shape or weight.

As used herein "sealing element" includes any structure which is designed to prevent leakage from the gastric environment or simulated methods thereof, into the cavity in the arm of the gastric retentive system.

As used herein, "sum exposure area" or "sum area of the overlapping areas" or "sum area of the overlapping surfaces" or "or "sum area of the exposed surfaces" means the sum area of the surface/s of the erodible insert that is/are exposed to gastric fluid in the stomach or under simulated gastric conditions. In an embodiment, an exposed surface of the erodible insert is the overlapping surface between the opening/s in the sleeve or tube housing the erodible insert, (illustrated by openings R1, R2, R3, R4 and R5 in FIGS. 21A and 21B), and the uncoated area of the erodible insert. In some embodiments, there is one overlapping surface. In some embodiments, there are more than one overlapping surfaces. The sum exposure area may be adjusted by the person skilled in the art in order to control the retention time in the stomach. In an embodiment, the "sum exposure area" is about 15.5 to about 59.8 mm$^2$. In an embodiment, the "sum exposure area" is less than 59.8 mm$^2$, or the sum exposure area is less than 40.7 mm$^2$, or the sum exposure area is less than 15.5 mm$^2$. In an embodiment, the sum exposure area is less than 59.8 mm$^2$ and the gastric retention time is at least 4.6 days, or the sum exposure area is less than 40.7 mm$^2$ and the gastric retention time is at least 6.6 days, or the sum exposure area is less than 15.5 mm$^2$ and the gastric retention time is at least 8.3 days.

As used herein, the terms "compressed configuration" and "collapsed configuration" are used interchangeably and refer to a state prior to ingestion where the GRDF has a size suitable for swallowing.

As used herein, the term "expanded configuration" is a state after ingestion where the GRDF is in a state that permits retention in the stomach (gastric retention) and prevention of passage through the pyloric valve.

As used herein, the term "upon exposure to gastric fluid" or "under simulated gastric conditions" or "upon exposure to gastric juice", unless expressed otherwise is meant to be taken literally or when needed, based on a suitable model. One example of such a suitable model includes a rotating bottle apparatus at 37° C. at 2-5 RPM having 400 mL 0.01N HCl, pH2 and optionally Xanthan gum 0.125 gr/L.

As used herein, the term "pharmaceutically acceptable" refers to a material that is not physically or otherwise unacceptable when used in accordance with the disclosure. For example, the term "pharmaceutically acceptable carrier" refers to a material that can be incorporated into a composition and administered to a patient without causing unacceptable physiological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

As used herein, any term relating to geometric terms, shape and/or orientation shall, unless otherwise defined or indicated, be understood to indicate conformance to the mathematical definition of such term to the extent possible for the subject matter so characterized as would be understood by one skilled in the art and would not to require absolute conformance to a mathematical definition of such term. Examples of such terms relating to geometric terms, shape and/or orientation include, but are not limited to terms descriptive of: shape (such as, round, square, circular/circle, rectangular/rectangle, triangular/triangle, cylindrical/cylinder, elliptical/ellipse, (n)polygonal/(n)polygon, vertex etc.); angular orientation (such as perpendicular, orthogonal, parallel, vertical, horizontal, collinear, etc.); contour and/or trajectory (such as, plane/planar, coplanar, hemispherical, semi-hemispherical, line/linear, hyperbolic, parabolic, flat, curved, straight, arcuate, sinusoidal, tangent/tangential, etc.); surface and/or bulk material properties, spatial/temporal resolution, distribution (such as, smooth, reflective, transparent, clear, opaque, rigid, impermeable, uniform(ly), inert, non-wettable, insoluble, steady, invariant, constant, homogeneous, etc.); as well as many others that would be apparent to those skilled in the relevant art. As one example, a system that would be described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described.

In the following description the terms "house", "contain", "received" (for example where the erodible insert is described as being received in the cavity) are all used synonymously and are used to mean "held within". The skilled person will appreciate that these terms are used interchangeably without any change in scope.

As used herein, the terms "constructed from" "consists of" and "formed of" may be used interchangeably and are intended to mean that a component is made from or otherwise comprises a specified material. The term "substantially" is intended to mean considerable in extent or largely but not necessarily wholly that which is specified. For example, substantially comprising a particular material may refer to comprising at least 60%, 70%, 80%, 90%, 95% or more of that material. As use herein, substantially maintaining weight, means maintaining of at least 80%, at least 90% or at least 95% of its original weight, measured e.g. in simulated gastric conditions, e.g. as measured in rotating bottle apparatus at 37° C. at 2.5 RPM having 400 mL, pH2 and Xanthan gum 0.125 gr/L.

As used herein, the term "opening force" is intended to describe the force of bias by the compressed state GRDF to open into the expanded configuration as illustrated, for example in F1 of FIGS. 20A and 20B or at least progress by 10% towards the expanded state configuration. The opening force may be calculated by deriving the minimum force required to maintain the gastric retentive device in compressed state as measured on a rigid surface.

As used herein, the term "rigidity" is the property of a GRDF which expresses the ability to resist change in size despite application of a force. In this case, it is the extent to which the GRDF is capable of resistance to a 10% decrease in any dimension of the expanded state upon application of a minimum force, as illustrated for example in F2 in FIG. 20.

As used herein, "retaining elements" are parts of the GRDF which fasten at least two parts of the GRDF one to each other. In an embodiment, the retaining elements are an integral part of the hinge assembly. In an embodiment, the retaining elements include protrusions extending from top and or bottom of the hinge assemblies, fitting into niches within the arm housing the erodible insert (the "mediating arm"). In an embodiment, the presence of the erodible insert tablets in the cavity maintains the protrusions within the niches until a certain extent of erosion and disassembly. In an embodiment, when the erodible insert is eroded to a certain extent, the protrusions are released from the niches so that the hinge assembly disengages form the mediating arm.

Description of GRDF

The present disclosure provides a GRDF and a method of use thereof. The GRDF is swallowed in a compressed configuration, expands in the stomach, performs its intended function for an extended time period, and at the end of the time period or upon occurrence of a mechanical event, mechanically disassembles into its separate parts for eventual passage through the pyloric valve of the stomach.

After exiting the stomach, the disassembled parts of the GRDF safely pass through the rest of the gastrointestinal system and are expelled from the body and/or are gradually eroded by pH conditions of the intestine. In some examples, disassembled parts are configured to partially or completely disintegrate after exiting the stomach. In other examples, the disassembled parts are configured to disintegrate to an extent necessary for evacuation from the body. In yet other examples, parts of the GRDF do not disintegrate and are evacuated intact.

According to the example, the GRDF described in detail below has a size, strength and shape that facilitates gastric residence as will be discussed in further detail below, and is configured to resist degradation, dissolution, erosion in the stomach until the required time at which point it is configured to disassemble for safe passage out of the stomach into the intestinal environment. The erodible insert located in the GRDF is configured to degrade, dissolve, erode or downsize in the stomach thereby controlling the time at which the size and strength of the GRDF is lost resulting in disassembly such that passage of the parts of the GRDF from the gastric environment is possible. It will be appreciated that because the erodible insert is for the most part located internal to the GRDF (except for a limited surface of erosion), the characteristics of the GRDF are maintained until a period of time close to the GRDF disassembly event.

The GRDF has collapsed or compressed, expanded and disassembled configurations. FIGS. 1A and 1B show an example of a GRDF in the expanded configuration. The GRDF of FIG. 1A comprises an articulated body that includes three arms 1001, 1002 and 1003. Arms 1001 and 1002 are pivotally connected to the ends of arm 1003. In the illustrated example, arms 1001 and 1002 are pivotally connected to arm 1003 by means of two hinge assemblies 1021, 1020. Arms 1001 and 1003 extend from, and may pivot around hinge assembly 1020; arms 1002 and 1003 extend from, and may pivot around hinge assembly 1021. In a preferred example, arm 1003 is not pivoted around hinge assemblies 1020 and 1021. Instead, arm 1001 is pivoted around hinge assembly 1020 and arm 1002 is pivoted around hinge assembly 1021.

In the expanded configuration of the GRDF, the arms 1001, 1002, 1003 form a closed circuit—e.g. a polygon or circle. It will be appreciated that although the term polygon is used throughout, in a case that the sides or arms have a curved shape in expanded state, the final shape may resemble a circle. In the non-limiting example of FIGS. 1A-1B and 2B the polygon is a triangle such that the three arms form a generally triangular shape. It will be appreciated however that polygons comprising more than three sides are also contemplated. The triangle may be any form of triangle, for example an isosceles triangle or an equilateral triangle. The triangle has three vertices—1030A-1030C (the term vertex, which may also be referred to as apex, is a mathematical term for each angular point or corner of a polygon). As discussed below, in the example of FIGS. 1-2, vertices 1030A-1030B are 'hinged' while vertex 1030C is 'hinge less' in that arms 1002 and 1001 are not pivotally connected to one another. In the illustrated example vertex 1030C is formed in situ as the GRDF transitions from a collapsed to an expanded state.

Also illustrated in the drawings is elastic leaf spring 1006 which mechanically biases the GRDF from a collapsed state to an expanded state. 1006 applies a torque on 1002 around 1021.

In the exemplary GRDFs of FIGS. 1A-1B, arms 1001-1003 thereof form a closed circuit (e.g. polygon). In the GRDF of FIGS. 1A-1B, arms 1001-1003 are effectively sides (e.g. elongated sides) of a closed polygon when the GRDF is in the expanded configuration. Although arms 1001-1003 are straight in their elongate direction in the example of FIGS. 1-2, this is not a requirement and one or more of the arms may alternatively be curved.

Arms 1001, 1002 and 1003 are all formed of a relatively rigid material such that they maintain their shape in both the expanded and compressed configurations. Thus the body is provided with sufficient strength to withstand the forces acting on it in both fasted and fed conditions of the stomach. In the illustrated example, the length of arms 1001, 1002 and 1003 are each individually comparable to the length of the respective arms in the compressed form and the width of each arm is comparable to the width of the compressed form. The depth of the arms when arranged in the compressed configuration is comparable to the depth of the respective arms in the compressed form. In the present disclosure, length is considered to correspond to the x-axis illustrated in FIG. 1A, width is considered to correspond to the z axis illustrated in FIG. 1A and depth is considered to correspond to the y axis illustrated in FIG. 1A.

In the example of FIGS. 1A-1B, hinge assemblies 1020, 1021 are attached to each end of arm 1003, thus, arm 1003 may be referred to as a 'mediating' arm. The mediating arm can be configured to provide a timed disassembly or alternatively can be configured to contain an active, diagnostic and/or electronic. In some examples where the mediating arm provides a timed disassembly, an active, diagnostic and/or electronic may form another part of the GRDF. In some examples, the mediating arm can be configured to provide a timed disassembly and to contain an active, diagnostic and/or electronic.

As will be discussed below, arm 1003 has a cavity in which an insert can be located.

As shown in FIG. 1B, an opening, 1007, is provided in arm 1003 to permit gastric fluid to enter the cavity when the system is in the stomach. Opening 1007 is illustrative of one or more openings in arm 1003 which can be localized at the external as well as the internal face of arm 1003.

Figure 2A:
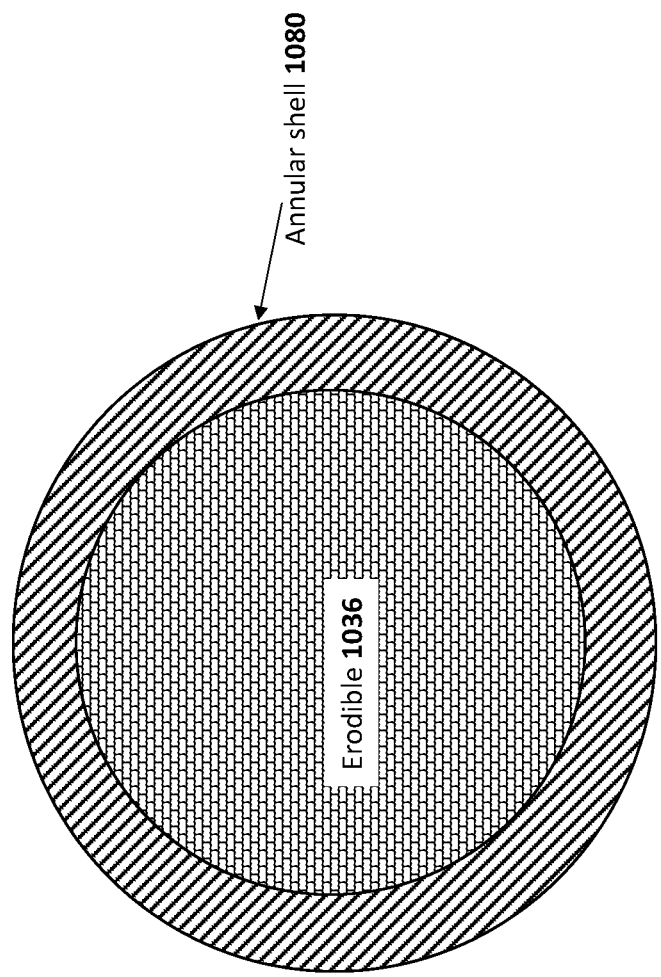
FIG. 2A is a cross sectional view of an erodible insert contained within an arm of the GRDF of FIGS. 1A and 1B.
Figure 2B:
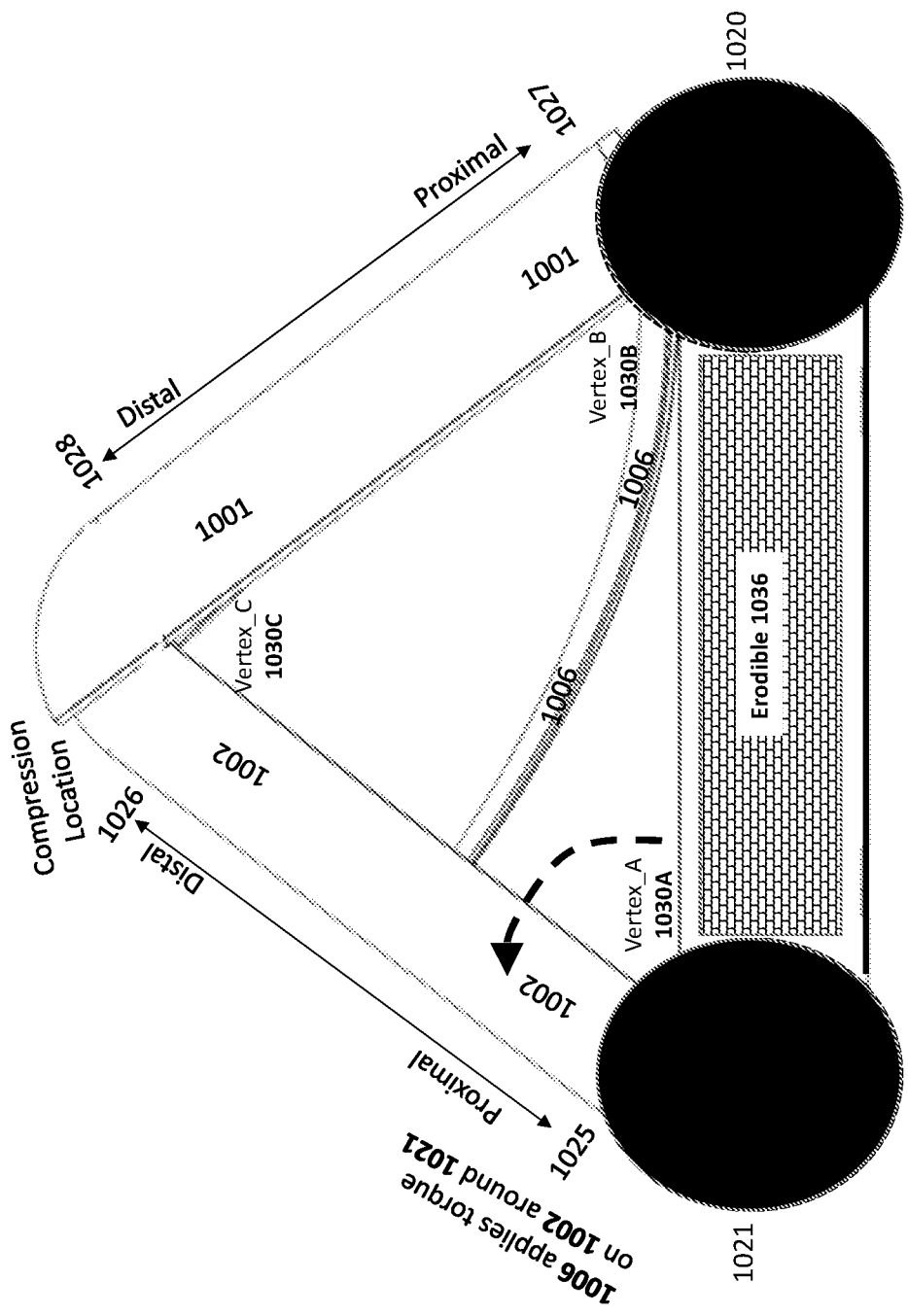
FIG. 2B is a schematic front view of the GRDF of FIGS. 1A and 1B illustrating the erodible insert located within the system.

In the illustrated example, arm 1003 is in the form of a tube or sleeve. In the illustrated example the tube or sleeve has a circular cross section and is thus in the form of a hollow cylinder having a cavity. However the tube may have alternative cross-sectional shapes such as square or rectangular. In some examples the cross section of the tube is an irregular polygonal shape. As discussed above, the tube is arranged to house an erodible insert, 1036, as shown in FIGS. 2A and 2B. In some examples the erodible insert has a complementing contour to the interior of the tube. In other examples the erodible insert fills only a portion of the interior of the tube. The tube may in any case be considered to form a shell or sleeve that surrounds an erodible insert, diagnostic or electronic device or combinations thereof. The tube, shell or sleeve has mechanical durability independent of its contents throughout its duration in the stomach.

The tube or sleeve may be constructed from material that is insoluble in gastric fluid. Alternatively the outer surface of the tube or sleeve comprises a pharmaceutically acceptable material which is insoluble in gastric fluid, for example at about 37 degrees C. As will be discussed below, in some embodiments, an erodible insert which may be in the form of one or more tablets (e.g. pharmaceutical-containing) may be disposed within arm 1003.

Arms 1001 and 1002 have a different construction than arm 1003 to allow the GRDF to be compressed to a compressed or collapsed configuration. Specifically, in the illustrated example, arms 1001 and 1002 have a generally hollow semi-cylindrical shape. Put another way, arms 1001 and 1002 are hollow and have a generally semi-circular cross section. The ends of arms 1001 and 1002 distal to arm 1003 are in the shape of a quarter hemispheres that closes what would otherwise be an open end of arms 1001 and 1002. Since arm 1003 has a substantially cylindrical shape and arms 1001 and 1002 have a generally hollow semi-cylindrical shape, the arms are able to overlay one another for example to form a nested arrangement in the compressed configuration as illustrated in FIG. 4C.

As discussed above, the shell or sleeve of arm 1003 may define at least one opening, void or window 1007 therein via which gastric fluid can penetrate the system so as to erode (e.g. pharmaceutical-containing erodible) the erodible insert disposed within the shell or sleeve. In some embodiments, this opening or window 1007 is relatively small—as will be discussed below, allowing for a controlled and/or directional erosion of the erodible insert. In the non-limiting illustrated example, a single opening or window is shown—it is appreciated that in other embodiments, a plurality of openings or windows may be provided.

The erodible insert may comprise a therapeutic agent, a diagnostic agent, an electronic device or combination thereof. For example, where the erodible insert is a therapeutic-agent-containing erodible insert, erosion thereof releases the therapeutic-agent into the gastric fluid. Thus, in this case erosion of the erodible insert is pharmaceutical-releasing erosion. FIG. 2A-2B illustrate the erodible insert 1036 (e.g. a tablet) within arm 1003. FIG. 2A is a cross section of arm 1003 and shows an annular shell 1080 or sleeve that is constructed of gastric-fluid-insoluble, pharmaceutically acceptable material and/or has an outer surface that is gastric-fluid-insoluble. Put another way, annular shell 1080 or sleeve is a protective shell or sleeve so that gastric fluid can preferably enter the cavity only via opening(s) 1007 (see FIG. 1B), allowing control of the erosion process such that for example the erosion is directional for example eroding from the centre outwards. In some examples, it may also be appreciated that the surface area and rate of erosion remains substantially consistent throughout the erosion process.

In the example of FIGS. 1A-1B, a proximal end of arm 1002 is labelled as 1025; a distal end hereof is labelled as 1026; a proximal end of arm 1001 is labelled as 1027; a distal end hereof is labelled as 1028.

In the example of FIGS. 1A-1B, pressure applied by leaf spring 1006 applied upon arm 1002 provides a torque around hinge assembly 1021. The leaf spring 1006 is an elastic leaf spring and biases the GRDF into the expanded configuration, thus the leaf spring 1006 acts as a biasing member and may be referred to herein as such. In the illustrated example, the leaf spring 1006 extends between hinge assembly 1020 and arm 1002 in the expanded configuration. However the leaf spring may extend between arm 1003 and arm 1002 in the expanded configuration. The biasing member may extend from or attach to another part of the GRDF. For example, the biasing member may be a portion of the hinge assembly mediating arm. In another example, the biasing member is a separate component.

In order to bias both arms 1001 and 1002 into the expanded configuration, the leaf spring is arranged between arm 1003 and arm 1002 when the arms overlay one another in the compressed configuration. In this manner the leaf spring acts on the arm 1002 which itself acts on the uppermost arm 1001 thereby biasing both arms into the expanded configuration.

As will be discussed below, in some embodiments at least one vertex 1030C may be hinge less. In the example of FIGS. 1A-1B (schematically illustrated in FIGS. 3A-3B), pressure applied by leaf spring 1006 upon arm 1002 (which provides a torque around hinge assembly 1021) urges a surface of arm 1002 at distal end 1026 thereof against a portion of side 1001 at distal end 1028 thereof to provide compression or a compressive force there between (see FIG. 3C). This compressive force causes the arms 1001 and 1002 to mechanically engage, thereby locking arms 1001 and 1002 together. As illustrated in examples, sustaining of this compressive force is required to maintain (e.g. stably sustain) vertex 1030C. As will be discussed below (e.g. in the context of disassembly—see FIG. 7), in some embodiments, ceasing of this compressive force (e.g. due to the ceasing of the torque around hinge 1021) dismantles vertex 1030C. Thus, the dismantling of the first vertex triggers a dismantling of a second of the vertices, thereby disassembling the closed polygon into a plurality of parts/units, each unit being sized for exit from the stomach via the pyloric valve.

FIG. 3A corresponds to FIG. 1B and is a schematic drawing of the triangle. In FIG. 3A, a protrusion 1090 of arm 1001 is additionally illustrated. Arm 1002 acts against the protrusion 1090 when the GRDF is biased into the expanded configuration. This facilitates retention of the GRDF in the expanded configuration. This will be discussed in further detail below.

Transition of the GRDF of FIGS. 1-3 from the compressed to the expanded state is now discussed with reference to FIGS. 4-5. FIG. 4A schematically illustrates the GRDF of FIG. 1-3 in a compressed state.

Figure 3B:
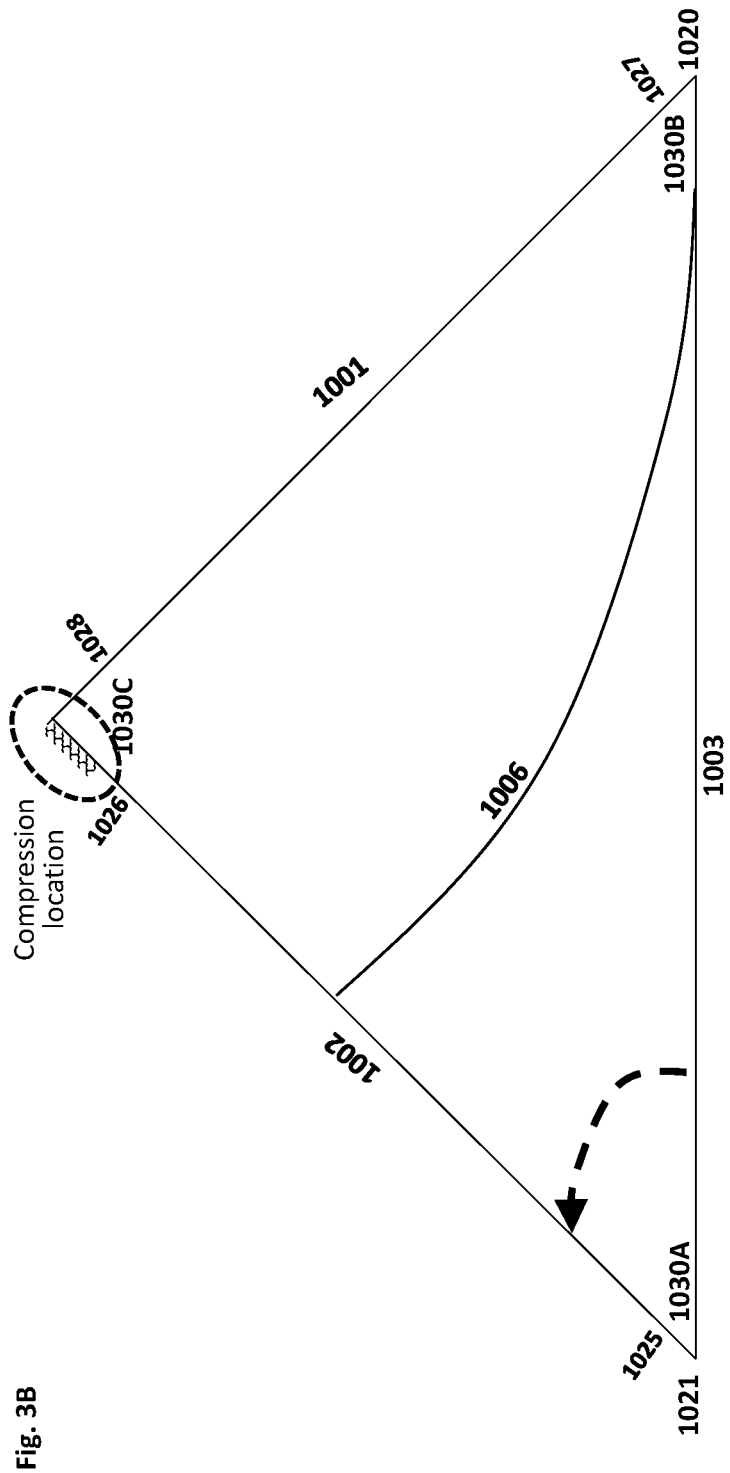
Figure 3C:
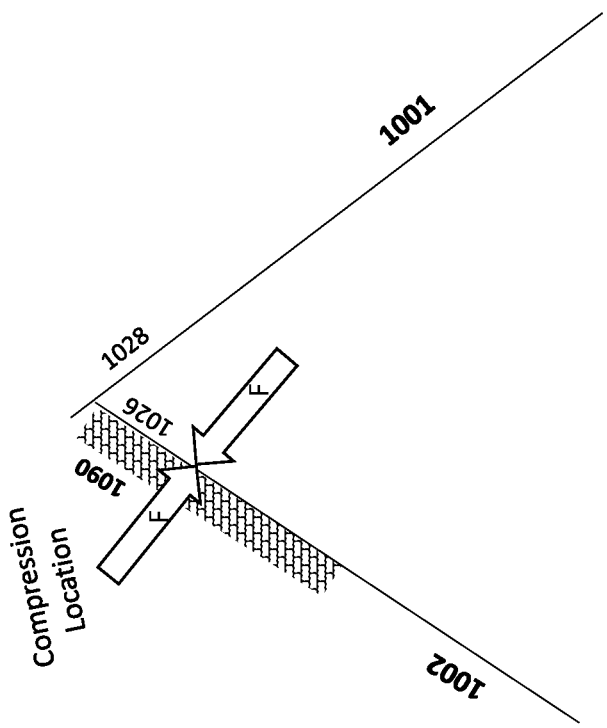
FIG. 3C is a simplified drawing of the hyphenated area in FIG. 3B.
Figure 4B:
FIG. 4B is a simplified drawing of FIG. 4A.
Figure 4A:
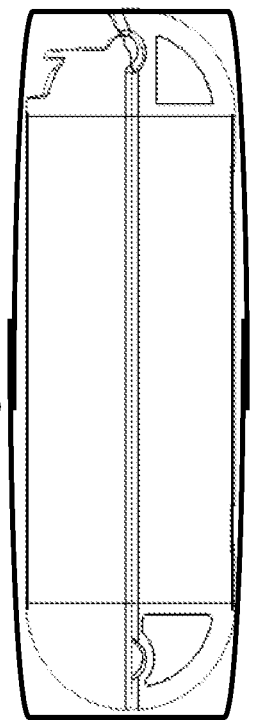
FIG. 4A is a front view of the GRDF of FIGS. 1A and 1B in a compressed configuration.
Figure 4C:
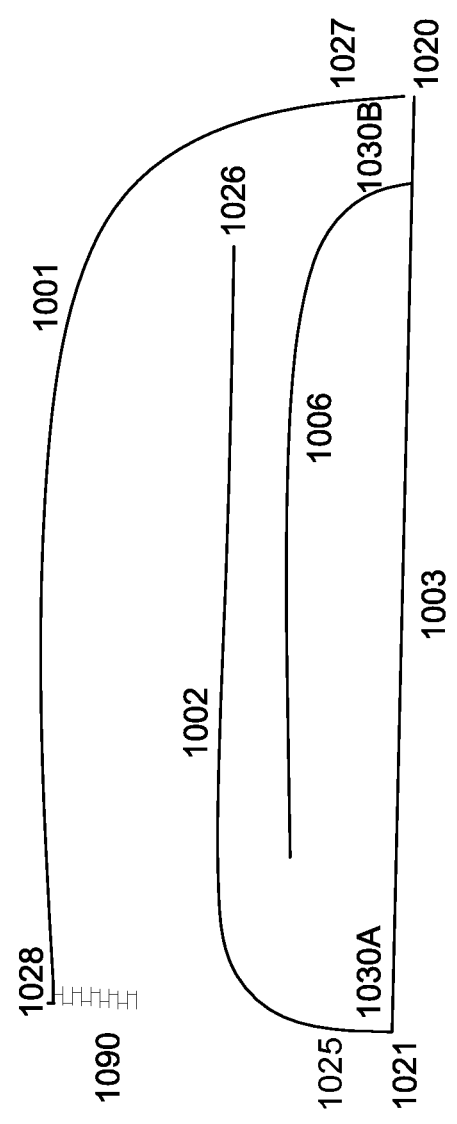
FIG. 4C is a vertically distorted version of FIG. 4B.

FIG. 4B illustrates the collapsed or compressed-state schematically, in a manner similar to that of FIGS. 3A-3B which illustrates the expanded state schematically.

To better illustrate the various elements of FIG. 4B, FIG. 4C illustrates the same compressed state of FIGS. 4A-4B in a vertically distorted view where vertical space is 'stretched.'

Thus, as shown in FIG. 4B, when in the compressed state, vertex 1030C does not exist. As will be discussed below, vertex 1030C may be formed in situ (e.g. within the stomach) by pressure applied by leaf spring 1006 upon side 1002 (i.e. this pressure provides the torque around hinge assembly 1021).

For example, due to the presence of leaf spring 1006, the GRDF is mechanically biased towards an expanded state. Before ingestion, this pressure may be counteracted by an erodible wrapper around the GRDF (e.g. of FIG. 4A). This wrapper or retainer can sustain the GRDF in the compressed configuration of FIG. 4A-4C. However, when in the stomach, erosion of this wrapper or retainer reduces or eliminates this counteracting force, causing the GRDF to transition from the compressed configuration to the expanded configuration as shown in FIG. 5.

The transition from the compressed configuration to the expanded configuration may be driven by elastic restoring forces—in the example of FIGS. 1-5 the restoring forces of leaf spring 1006. The transition may close a circuit (e.g. a polygon) and/or form a vertex (e.g. hinge less vertex) 1030C.

FIGS. 1-5 illustrate various elements of the system that may, in different embodiments, be useful for forming and/or sustaining vertex 1030C.

Figure 6:
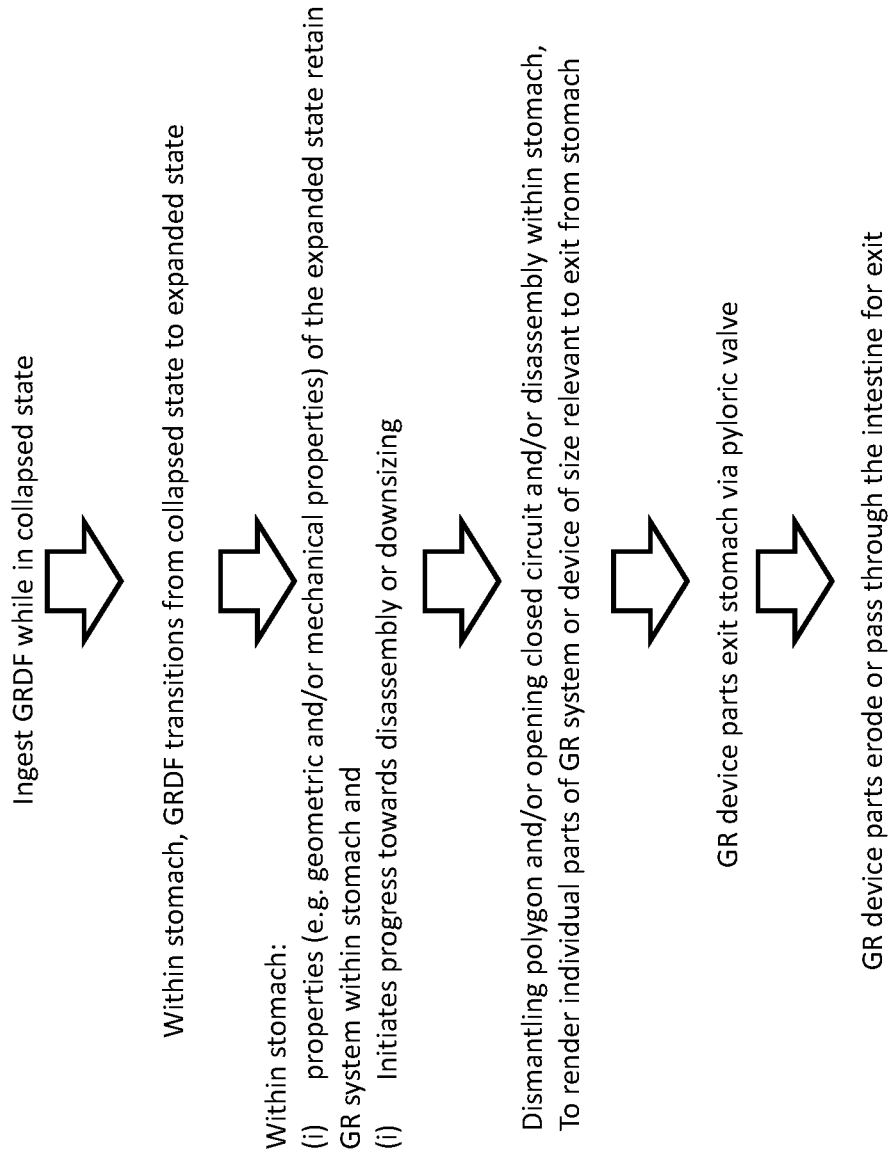
FIG. 6 is a flow chart of the process which a GRDF undergoes in use.
Figure 7B:
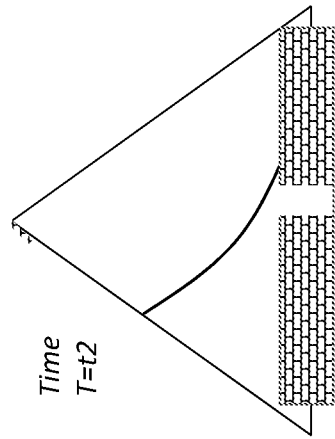
FIGS. 7A-7D illustrate a sequence of simplified drawings showing the change in an erodible insert within the GRDF of FIGS. 1A-1B over time.
Figure 7D:
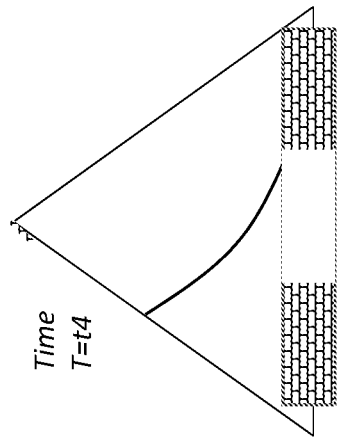
Figure 7A:
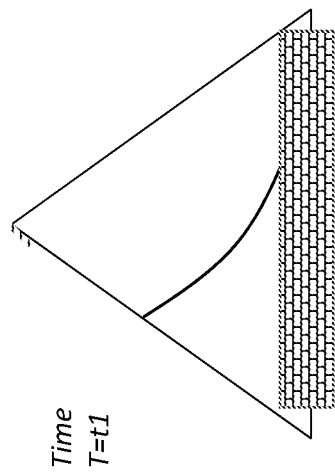
Figure 7C:
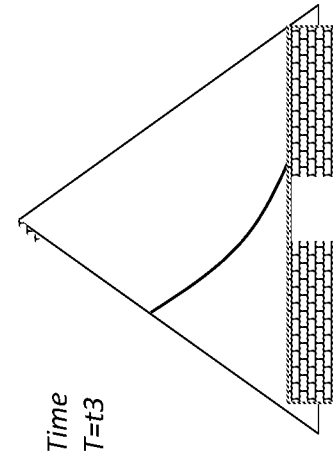

FIG. 6 is a flowchart of an extended-release method using any presently-described gastric retention system.

FIG. 7 illustrates the expanded state of the GRDF and progressive erosion of the erodible insert in accordance with some embodiments. In particular, in some embodiments an erodible insert (e.g. tablet 1036) is present in mediating arm 1003—e.g. within a shell or sleeve having at least one window or opening 1007 via which gastric fluid may penetrate. In accordance with some embodiments, the erodible insert is in direct contact with an inner surface of mediating arm 1003. When an erodible insert is present in mediating arm 1003 the combination of the GRDF body and erodible insert is referred to as a GRDF.

Figure 8:
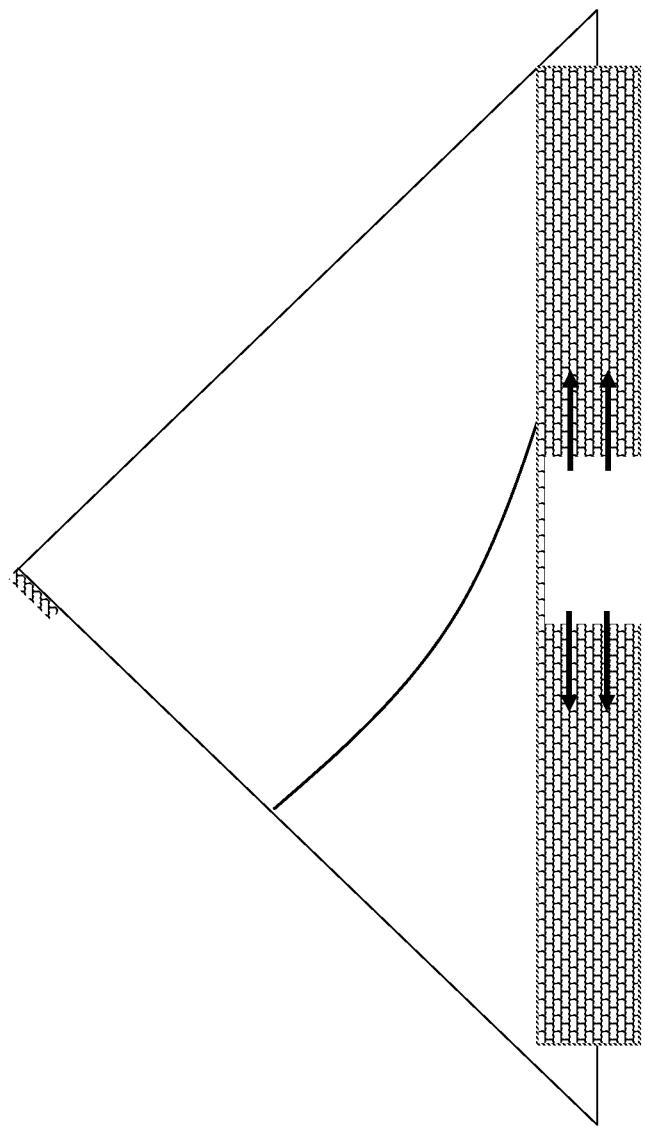
FIG. 8 is a simplified drawing of the GRDF of FIGS. 1A-1B in use.

At time t1 gastric fluid has yet to penetrate into an interior of arm 1003 where erodible insert 1036 is disposed. As noted above, in the example of FIGS. 1-5, an interior of arm 1003 is mostly sealed from the external environment (e.g. gastric fluid). In some examples, the window or opening 1007 is in a central portion of side/arm 1003. As such, and as illustrated in FIGS. 7 and 8, over time (e.g. at times t2, t3, t4) erosion of the erodible insert 1036 within arm 1003 is 'outward' erosion, e.g. from a central point in the arm in both directions towards arms 1002 and 1001 and hinge assemblies.

In some embodiments, erodible insert 1036 comprises a pharmaceutical—thus, the erosion illustrated in FIG. 7 is pharmaceutical-releasing erosion. Although erodible insert 1036 may comprise a pharmaceutical, any constitution may be envisioned whether uniform or in layers.

Figure 11:
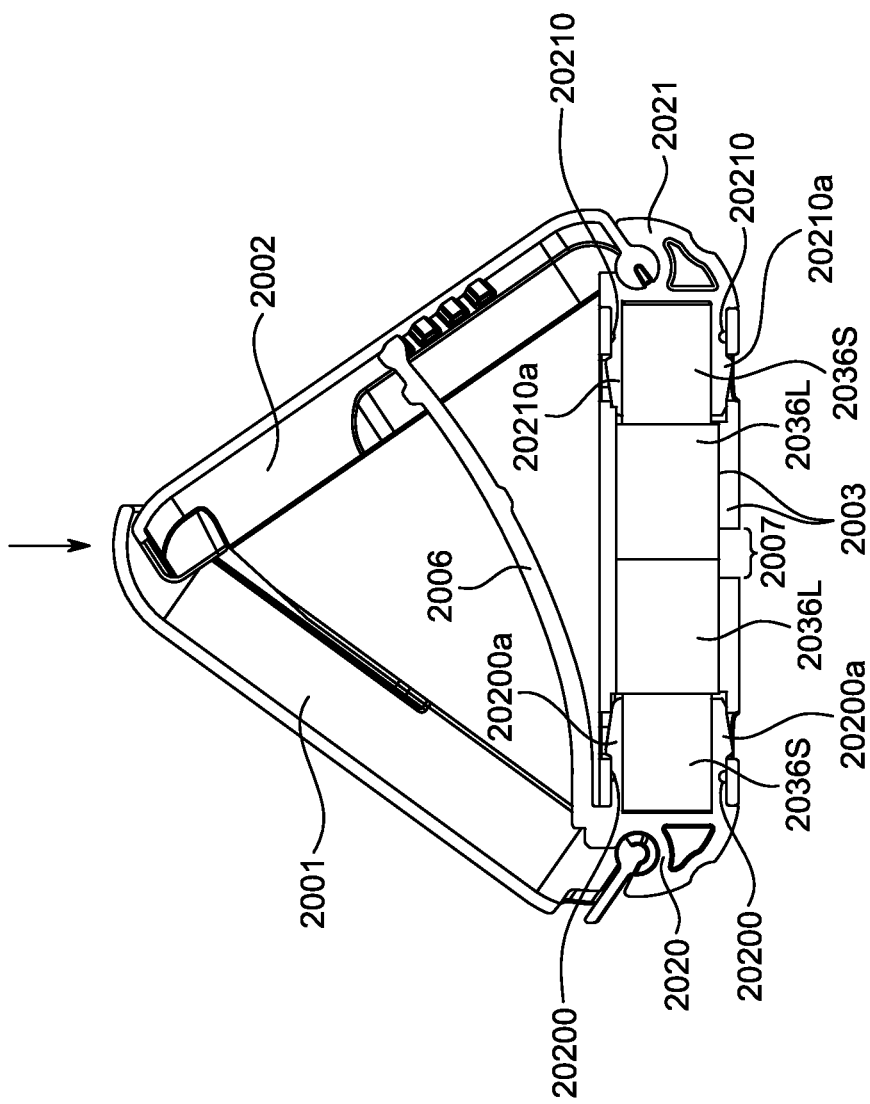
FIG. 11 is a cross-sectional view of the GRDF of FIG. 10.
Figure 19B:
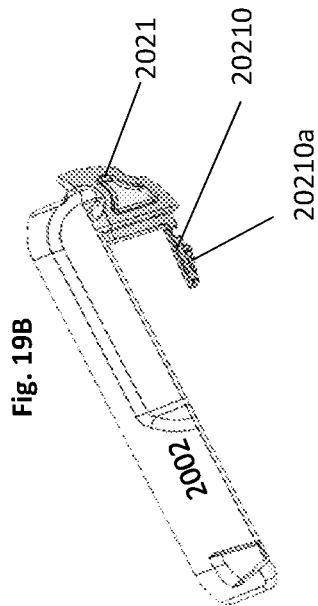
FIGS. 19A and 19B illustrate arms and hinge assemblies of the GRDF shown in FIG. 10.
Figure 19D:
FIGS. 19C and 19D illustrate views of a sleeve of the GRDF shown in FIG. 10.

In the illustrated example, the presence of an erodible insert 1036 whether a unit (e.g. tablet) or series of inter-fitting units as illustrated in FIG. 11 and FIG. 19D as 2036S and 2036L may maintain an attachment between hinge assembly 1020 or portion thereof and/or hinge assembly 1021 or portion thereof and arm 1003. In this example, erosion of the erodible insert sufficiently modifies geometric and/or mechanical properties of insert 1036 (e.g. which is erodible) to detach a hinge assembly 1020 and/or hinge assembly 1021 from arm 1003. The modified geometric and/or mechanical properties of the erodible insert which result in detachment of a hinge assembly occur within an inner cavity of arm 1003. In this manner, the properties of the GRDF remain substantially unaltered until mechanical disassembly.

Figure 9:
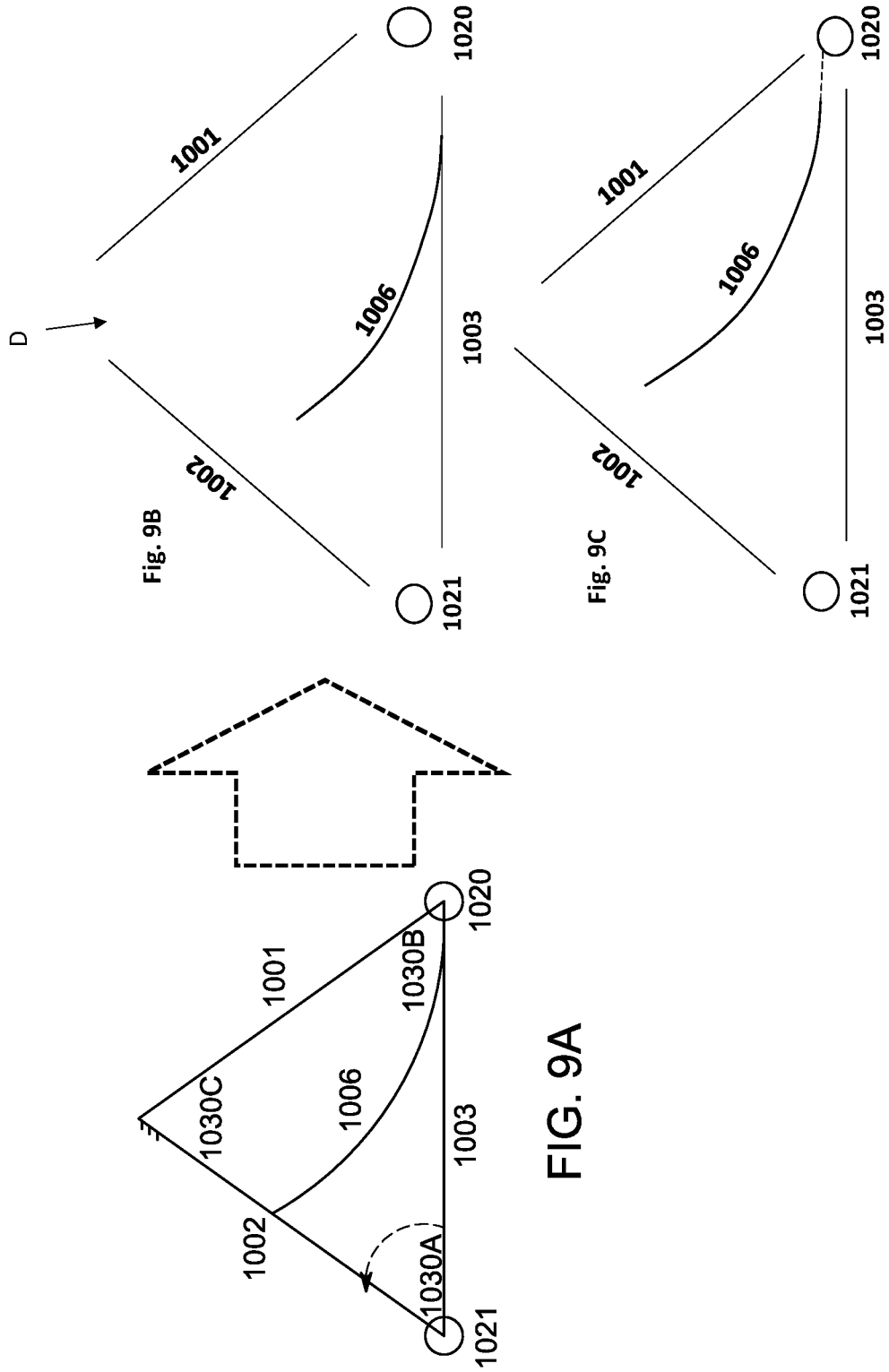
FIGS. 9A-9C illustrate simplified drawings of the expanded state and two alternative disassembled states of the GRDF of FIGS. 1A-1B.

As illustrated in FIG. 9, this detaching drives opening of the closed circuit or closed polygon and/or disassembly of the GRDF into units that are sized for exiting the stomach via the pyloric valve. FIGS. 9B and 9C illustrate two alternatives for disassembly, wherein 1006 is integrally connected to arm 1003 (FIG. 9B) or to hinge assembly 1020 (FIG. 9C).

Further details of a specific example of a GRDF of the present disclosure are described in detail below with respect to FIGS. 10-21.

Figure 10:
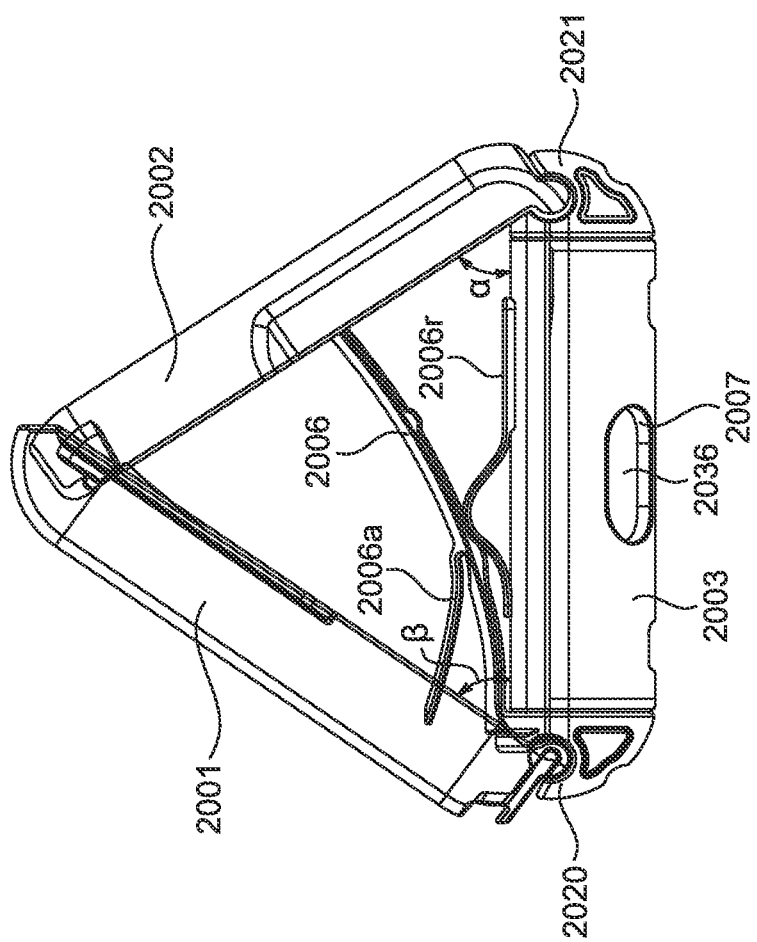
FIG. 10 is a front view of a GRDF in an expanded configuration.
Figure 19A:
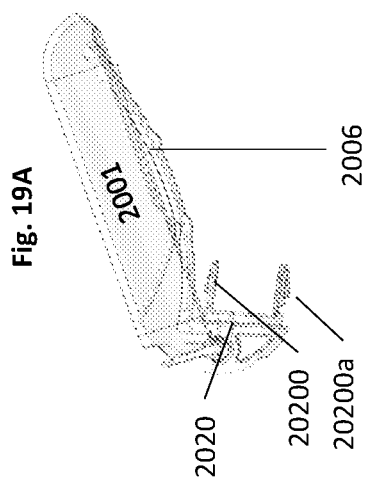
Figure 19C:
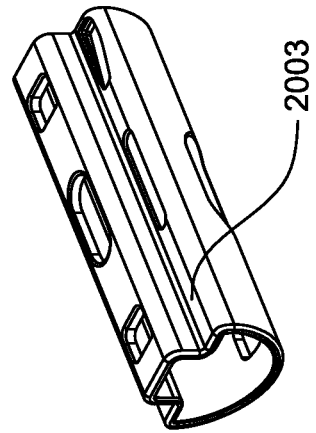

FIG. 10 illustrates a front view of a GRDF in an expanded configuration while FIGS. 19C and 19D illustrate a side view of a sleeve of the GRDF shown in FIG. 10. The arrangement of this GRDF is similar to that illustrated in FIG. 1.

The GRDF illustrated in FIG. 10 includes three arms 2001, 2002 and 2003 in a similar manner to that illustrated in FIG. 1. The three arms 2001, 2002 and 2003 together form a body. The body is in the form of a generally triangular shape with arm 2003 as the base of the triangular shape and arms 2001 and 2002 as the sides of the triangular shape. Arms 2001 and 2002 are pivotally connected to the ends of arm 2003 thereby forming two apexes or vertices of the triangular shape. Arms 2001 and 2002 are mechanically engaged with one another to form the third apex or vertex of the triangular shape. The triangular shape may be any form of triangle, for example an isosceles triangle or an equilateral triangle. Due to the triangular arrangement of arms 2001, 2002 and 2003, the angle α or angle β between arms 2001 and 2003, and 2002 and 2003 can each be between about 30 degrees and 90 degrees and in some examples is around 60 degrees. For example, angle α and angle β may be about 60 degrees.

Although in the illustrated example a triangular shaped expanded configuration is illustrated, other shaped expanded configurations are also envisaged for example, circular (i.e. where arms have curvature), rectangular, rhombus or other quadrilateral shape, hexagonal, octagonal etc. Any suitable polygonal or circular shape may be used.

A biasing member in the form of a leaf spring mechanically biases arm 2002 thereby biasing the three arms 2001, 2002 and 2003 into the expanded configuration. This will be discussed in further detail below. Although in the illustrated example an elongate leaf spring 2006 is used as a biasing member, other suitable biasing arrangements may also be used. For example, a biasing member in the form of a helical spring and an elongate member may be used. Additional support for the biasing member may also be included such as an additional biasing member in the form of an elongate leaf spring 2006a to bias the elongate leaf spring 2006 and the 2001 arm. Alternatively the 2006r ramp which is configured to bias the elongate leaf spring 2006 from the first arm 2003 may provide additional support in transition.

In the illustrated example, arm 2003 is in the form of a tube (See FIG. 19C). In this manner the interior of arm 2003 forms a cavity in which an erodible insert (See FIG. 19D) may be located. As can be viewed in FIGS. 10, 11, 14B, 15, 16 and 19, hinge assemblies or sealing elements 2020 and 2021 are provided at the open ends of arm, sleeve or tube 2003. In the illustrated example, hinge assemblies 2020 and 2021 include hinge assemblies by which arm 2003 is pivotally connected to arms 2001 and 2002 respectively. One end of biasing member 2006 is attached to hinge assembly 2020. In the illustrated example the biasing member 2006 is integrally formed with hinge assembly 2020. In other examples, the biasing member 2006 may be separately formed and connected to hinge assembly 2020. In yet further examples, the biasing member 2006 may be attached to arm 2003 instead of hinge assembly 2020.

Since arm 2003 contains an erodible insert it may be considered a "mediating arm", "containing arm" or "loaded arm". In the illustrated example only one arm of the GRDF is loaded with an erodible insert.

In the illustrated example, arms 2001 and 2002 are in the form of hollow half cylinders (See FIGS. 19A and 19B). Put another way, arms 2001 and 2002 are in the form of cylinders that have been cut in half along their length. Arms 2001 and 2002 have a similar cross section to arm 2003 so as to correspond to arm 2003. In this manner, the three arms 2001, 2002 and 2003 can overlay one another when the system is compressed as will be discussed in further detail below. Arms 2001 and 2002 are hollow and therefore do not contain any erodible insert. The arms 2001 and 2002 provide structural support in order to provide the body with the required shape and structure in the expanded configuration. They may therefore be considered to be structural arms.

FIG. 11 is a cross-sectional view of the GRDF of FIG. 10 and illustrates further details of the system. In the cross sectional view of FIG. 11 a cavity formed within arm 2003 can be seen more clearly. Opening 2007 is provided centrally at the base of arm 2003 in the illustrated example to provide access to the cavity from the exterior of arm 2003. The opening 2007 is representative of one or more openings and those may be provided at any suitable location, can be provided on an upper or side surface of arm 2003 and may be arranged at any point along the length or arm 2003. In the illustrated example only one opening is provided. However in other examples such as presented in FIG. 21A, FIG. 1B and FIG. 22 a plurality of openings may be provided to facilitate ingress of gastric fluid to the GRDF.

Hinge assemblies 2020 and 2021 include retaining elements 20200 and 20210, respectively that extend into the interior or cavity of arm 2003. In the illustrated example each hinge assembly 2020 and 2021 includes two retaining elements 20200 and 20210, respectively. One retaining element extends from the top of each hinge assembly 2020 and 2021 and one retaining element extends from the bottom of each hinge assembly 2020 and 2021 such that when the hinge assemblies 2020 and 2021 are located in arm 2003, the retaining elements 20200 and 20210 act on upper and lower surfaces of the interior of arm 2003. However the present disclosure is not limited to this arrangement and the retaining elements can be arranged to extend into arm 2003 at the sides or at any suitable location around the interior of arm 2003. Additionally in the illustrated example, two retaining elements are shown, however in other examples only one or alternatively more than two retaining elements can be provided. Any suitable number of retaining elements can be provided. The greater the number of retaining elements the more securely hinge assemblies 2020 and 2021 are held inside arm 2003 for extended periods of time under gastric conditions.

Retaining elements 20210 and 20200 include protrusions 20210a and 20200a, respectively, extending radially outward therefrom. The protrusions 20210a and 20200a are arranged to cooperate with corresponding recesses in the inner surface of arm 2003. Protrusions 20210a and 20200a include a shoulder against which an inner surface of the arm 2003 abuts. In this manner the retaining elements 20210 and 20200 prevent the hinge assemblies from falling out or being easily removed from arm 2003 and assist in retaining the hinge assemblies 2020 and 2021 in arm 2003. It can be appreciated that the contour of the protrusions 20210a and 20200a, shoulder and arm 2003 may be adjusted to increase the cooperation with the corresponding recesses protrusions as well as the sensitivity to the presence of the insert tablet such that once the insert erodes to a specific degree, the protrusions 20210a and 20200a no longer cooperate with the corresponding recesses in the inner surface of the arm 2003.

With reference to FIG. 11, biasing member 2006 extends from a first end at, or proximal to, hinge assembly 2020, to a distal end at arm 2002. The distal end of biasing member 2006 engages with a protrusion on an inner surface of arm 2002. In the illustrated example three protrusions are provided adjacent to each other to provide three different locations for the biasing member to engage. In alternative examples arm 2002 is provided with only a single protrusion. In other alternative examples one or more recesses may be provided in which the biasing member can be located. By providing either a protrusion or recess against which the biasing member can locate, the biasing member 2006 can assist in retaining the GRDF in the expanded configuration. However this may not provide the only means by which the GRDF is retained in the expanded state. As such, in some examples, the biasing member 2006 does not engage with arm 2002 but simply abuts against it.

FIG. 11 further illustrates the engagement of arms 2001 and 2002 to form the third apex or vertex of the triangular shape of the system. As can be seen, an outer surface of arm 2002 engages with an inner or retaining surface of arm 2001. The force of the biasing member outwards, causes arm 2002 to be pushed against the interior of arm 2001. The outer end of arm 2001 encloses the outer end of arm 2002 thereby forming an apex or vertex. In this manner arms 2001 and 2002 are locked together thereby retaining the GRDF in the expanded state. The mechanical engagement of the ends of arms 2001 and 2002 provides the main force for retaining the GRDF in the expanded state and can therefore be seen as a locking or retention mechanism. Put another way, the free ends of arms 2001 and 2003 in the compressed configuration come into contact to provide a closed circuit in the expanded-state articulated body via a locking mechanism.

Further details of the locking or retention mechanism are illustrated in FIG. 12. FIG. 12 illustrates the engagement of arms 2001 and 2002 when locked together. As illustrated, arm 2001 includes a tooth 2001a that protrudes therefrom. The tooth 2001a is tapered or in the form of a ramp although other shapes and configurations are also contemplated. Arm 2002 has a cut away portion or indentation 2002a formed on an outer surface thereof at the end of arm 2002 distal to arm 2003. The cut away portion 2002a and tooth 2001a cooperate with one another and provide a further means of mechanical engagement of arms 2001 and 2002 in addition to the mechanical engagement of the outer surface of arm 2002 with the inner surface of arm 2001 thereby providing additional retaining means, for example against a tangential force that may otherwise result in detachment. In some examples the tooth 2001a is not present and an edge or outer surface of arm 2001 cooperates with indentation 2002a. In other examples neither the indentation 2002a nor tooth 2001a are provided and the mechanical engagement of the ends of arms 2001 and 2002 provides sufficient force to retain the arms in the expanded state triangular shape.

A plane 2001c contacts plane 2002c when a radial force F1 is applied externally. Both planes 2001c and 2002c are angled such that the contact between the plane 2001c and the plane 2002c keeps arm 2001 locked with arm 2002.

In providing a means by which arms 2001 and 2002 are locked together in the expanded state, the GRDF is provided with sufficient strength to enable it to be retained in the stomach and resist the forces applied by the stomach under both fed and fasted conditions. The mechanical strength afforded by the shape, interaction and engagement of arms 2001, 2002 and 2003 in the expanded configuration is sufficient to enable the preservation of the expanded configuration under gastric conditions. This assists in the provision of gastric retention since the expanded state of the GRDF is sized so as to be too large to pass through the pyloric valve as will be discussed in further detail below.

Figure 13:
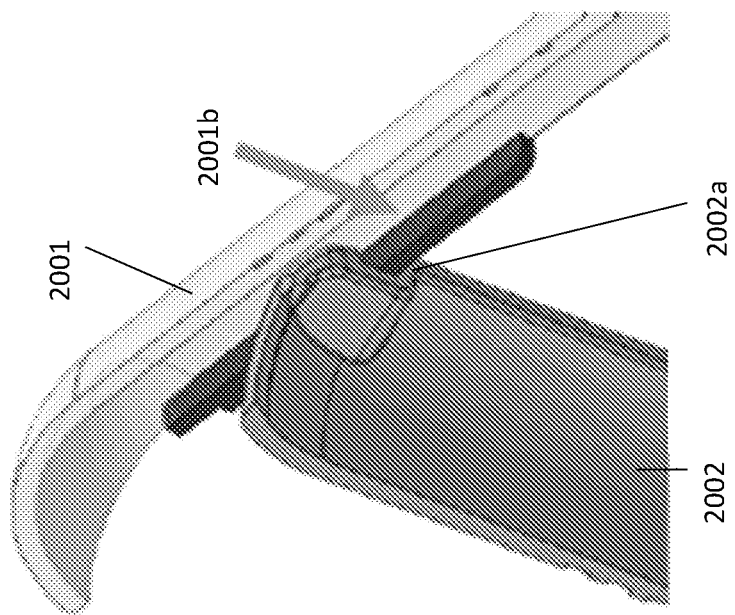
FIG. 13 illustrates a close up view of a guiding or sliding mechanism of the GRDF of FIG. 10.

FIG. 13 illustrates further features of arms 2001 and 2002. In the illustrated example, an indentation 2002a in arm 2002 engages with a rail or slider 2001b provided on arm 2001 as the GRDF transitions into the expanded configuration. Rail 2001b is in the form of an elongate protrusion extending from arm 2001. Rail 2001b extends along the length of arm 2001 and is arranged to guide arm 2002 along arm 2001 into the locked configuration. This rail 2001b can be considered a guiding member. The provision of a guiding member keeps arm 2002 in the same plane as arm 2001 thereby facilitating the compression of the GRDF into a compressed configuration or the expansion of the GRDF into the expanded configuration.

Figure 14A:
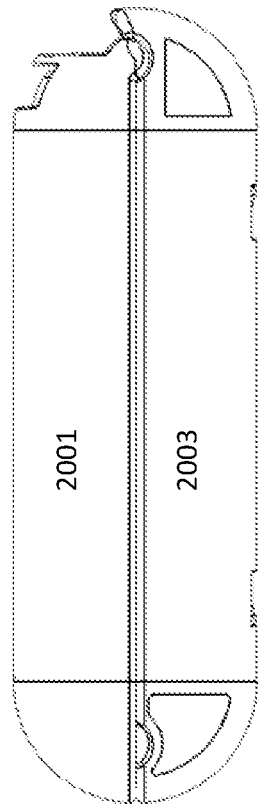
FIG. 14A is a front view of the GRDF of FIG. 10 in a compressed configuration.
Figure 14B:
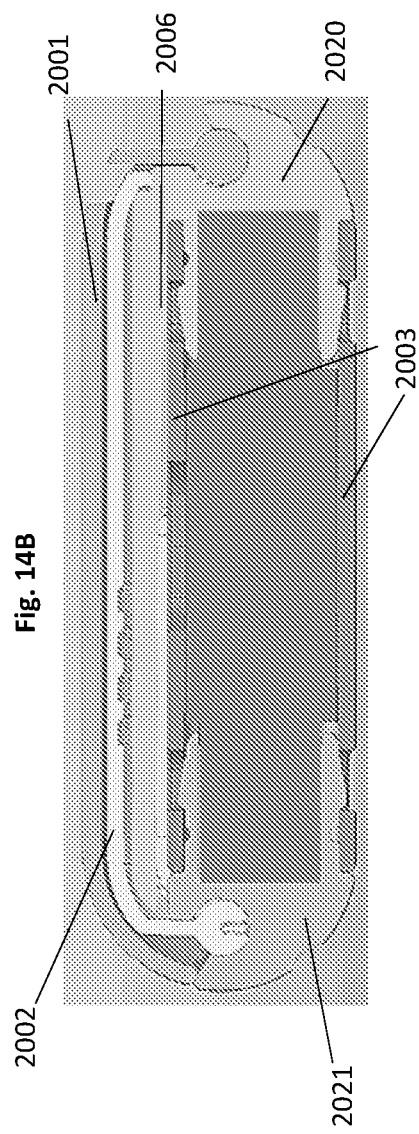
FIG. 14B is a cross-sectional view of the GRDF of FIG. 10 in a compressed configuration.

FIGS. 14A and 14B illustrate the GRDF in the compressed configuration. FIG. 14A is a front view of the GRDF in the compressed configuration and FIG. 14B is a cross-sectional view of the GRDF in the compressed configuration. As illustrated, arms 2001 and 2002 have been pivoted around to overlay arm 2003. The interior of arm 2002 has a corresponding shape to the exterior of arm 2003 and the interior of arm 2001 has a corresponding shape to the exterior of arm 2002. In the compressed position, arm 2002 overlays arm 2003 and arm 2001 overlays arm 2002. In this manner in the compressed state the arms 2001, 2002 and 2003 are provided one inside the other or nested together. This provides a compact arrangement that is easy for a patient to ingest for example when contained in a capsule or container.

As discussed above the GRDF of the present disclosure is designed to be swallowed in a compressed configuration, expanded in the stomach, perform its intended function for an extended and predetermined time period, and at the end of the time period or upon occurrence of a mechanical event, disassemble and/or disintegrate or preferably disassemble for eventual passage through the pyloric valve of the stomach. Thus, it is important that the GRDF can withstand the forces applied by the stomach and retain its shape and configuration in the expanded configuration so as to prevent unintentional disassembly into smaller parts that would fit through the pyloric valve before expiry of the predetermined time period and/or before the GRDF has finished performing its intended function. The GRDF of the present disclosure is advantageously able to endure the significant forces applied to it under gastric conditions due to the particular size, shape and strength of the expanded state thereby enabling the GRDF to perform its intended function for the required period of time. The GRDF is further designed to disassemble into components or parts small enough to pass through the pyloric valve once it has performed its function as will be discussed in further detail below.

The erodible insert is designed to degrade, erode or change its physical characteristics in the physiological conditions of the gastric environment. In an aspect, the erodible insert is the only component that degrades, erodes or changes its physical characteristics the physiological conditions of the gastric environment. Thus erosion of the erodible insert does not cause degradation or erosion of arm 2003, and the mechanical strength of arm 2003 is maintained throughout erosion of the erodible insert. In some examples, the erodible insert can be configured to provide directional erosion for example from the center of the first arm towards the ends/hinge assemblies. Thus, the erodible insert can provide a timed disconnection of the second and/or third arm which commences at greater than 60% erosion, at greater than 70% erosion, at greater than 80% erosion, at greater than 90% erosion or at greater than 95% erosion of the erodible insert.

In the example illustrated in FIG. 15A the erodible insert fills the entirety of the cavity in arm 2003. In particular the erodible insert is sized such that hinge assemblies 2021 and 2020 have an interference fit between the erodible insert and the interior surface of arm 2003. The close fit of these components is such that the erodible insert provides an outward or compressive force which pushes resilient protrusions 20210*a* and 20200*a* into the recesses on the interior surface of arm 2003. This ensures that the hinge assemblies 2020 and 2021 remain located in the ends of arm 2003. In the illustrated example the erodible insert is in the form of one or more tablets.

Once the erodible insert has been inserted into the body thereby forming a GRDF, the system is compressed into the compressed state before ingestion. The system may be compressed by hand or using a machine or device similar to that described in WO2017/093976. After compression the system is retained in the compressed state by locating the system inside a capsule or container. The capsule has the additional function of preventing gastric fluid from entering opening or openings 2007. The capsule is formed of material that is strong enough to withstand the inherent biasing force of the biasing member and thus retains the system in the compressed state. The capsule material also erodes or dissolves upon exposure to gastric fluid. Thus once the capsule is ingested by a patient, the capsule erodes in the presence of gastric fluid in the stomach. This removes the force retaining the system i.e. the GRDF containing the erodible insert in the compressed configuration. The inherent bias of the biasing member then biases the GRDF, and thus the overall system, into the expanded state where it is retained by means of the mechanical engagement of arms 2001 and 2002. Thus automatic transformation into the expanded configuration is achieved. The transformation of the system into the expanded configuration is independent of the erodible insert and therefore is solely dependent on the mechanical arrangement of the GRDF. The GRDF is designed such that the transformation from the compressed configuration to the expanded configuration occurs rapidly. In some examples the GRDF is configured to transform between the compressed configuration for ingestion and the expanded configuration for gastric retention within less than 10 minutes, less than 5 minutes, less than 4 minutes, less than 3 minutes or preferably less than 2 minutes.

Once the GRDF has been ingested and travels to the stomach, the capsule has eroded and the GRDF has transformed into the expanded state, the GRDF remains in the stomach for a predetermined period of time. The GRDF is thus sized so that in the expanded state, it cannot exit the stomach through the pyloric valve. In order to prevent passage through the pyloric valve, the GRDF in the expanded state must have a minimum turning radius capable of resisting passage through the pyloric valve. "Turning radius" is understood to mean a critical dimension via which the system could be rotated and/or turned to fit through an opening, for example the pyloric valve, ring or a tube having a defined diameter and height. This is not necessarily the smallest dimension or diameter of the GRDF but rather is a function of the 3D geometry of the GRDF (depth, width, length of the GRDF), the dimensions (for example radius r and height 30 mm) of the valve or simulated model thereof, and amount of space on either size of the valve. By providing a GRDF of appropriate geometry, a GRDF that can remain in the stomach for a desired period of time is provided. For example, the minimum turning radius may be measured through rotation in any orientation in attempt to fit through a simulated model of pyloric valve (for e.g. a ring having a defined diameter).

In one example of the gastric retentive systems disclosed, there is provided an expanded state device having a smallest turning radius greater than about 20 mm or greater than about 22 mm or greater than about 24 mm or greater than about 25 mm or greater than about 26 mm. In another embodiment, gastric retention may be achieved with a device having smallest turning radius less than 35 mm or less than 32 mm or less than 30 mm or less than 28 mm. In other embodiments, gastric retention may be achieved with a device in expanded state, having smallest turning radius between 20 and 35 mm or about 20 mm to about 32 mm or between 20 and 30 mm or about 20 to about 28 mm or about 22 and 35 mm or about 22 mm to about 32 mm or between 22 and or about 22 to about 28 mm or about 24 and 35 mm or about 24 mm to about 32 mm or between 24 and 30 mm or about 24 to about 28 mm or about 24 and 35 mm or about 24 mm to about 32 mm or between 24 and 30 mm or about 24 to about 28 mm or about 26 and 35 mm or about 26 mm to about 32 mm or between 26 and 30 mm or about 26 to about 28 mm or about 28 and 35 mm or about 28 mm to about 32 mm or between 28 and 30 mm. Combinations of the above-referenced ranges are also possible. The turning radius may be measured prior to exposure to gastric environment.

Another way of considering an appropriate size of the GRDF is to consider the ratio between: (i) a minimum enclosing ring of the GRDF in the expanded state and (ii) a minimum enclosing ring of the GRDF in the compressed state. In examples of the GRDF disclosed, the ratio is at least 1.5 or at least 2 or at least 2.5 and/or at most 10 or at most 7.5 or at most 5 or at most 4 or at most 3.5 or at most 3.0. Combinations of the above-referenced ranges are also possible. Another way of considering an appropriate size of the GRDF disclosed herein is to consider a ratio between (i) the post-cleavage length of the mediating sleeve or tube and a (ii) a pre-cleavage and expanded-state diameter of a minimum-enclosing sphere of the GRDF, is at least 0.05 or at least or at least 0.2 or at least 0.3 or at least 0.5. Combinations of the above-referenced ranges are also possible.

Another way of considering an appropriate size of the GRDF is to consider the convex hull volume. This term is known to those skilled in the art to refer to a set of surfaces defined by the periphery of a three-dimensional object such that the surfaces define a volume. In the present disclosure, appropriate size refers to a GRDF large enough in the expanded configuration to prevent passage through the pyloric valve yet small enough in the compressed configuration to enable it to be swallowed. In order to meet these requirements it has been established that a convex hull volume of the compressed configuration is about 20 to about 40% or about 25 to about 35% or about 30% to about 40% of the convex hull volume of the expanded configuration. In order to meet these requirements it has been established that a convex hull volume of the expanded configuration is about 200 to about 400% or about 250 to about 350% or about 300% to about 400% of the convex hull volume of the compressed configuration. By providing a device with a smallest turning radius of about 20 to about 35 mm or about 22 mm to about 28 in an expanded configuration and/or a convex hull volume in a compressed configuration of about 30% of the expanded configuration convex hull volume, it is ensured that the GRDF can be safely swallowed in its compressed configuration yet resistant to passage through the pyloric valve in the expanded configuration.

After a predetermined time in the stomach during which the pharmaceutical or diagnostic is released, the system disassembles into a number of smaller parts which are small enough to fit through the pyloric valve and pass out into the intestine and thence out of the body. The mechanism by which the GRDF disassembles will now be discussed with reference to FIGS. 15A-15D.

FIG. 15A illustrates the system (i.e. the GRDF containing the erodible insert) in the expanded state once the capsule retaining it in the compressed state has been eroded or dissolved. The dissolution of the capsule removes a cover over opening 2007 and thus allows gastric fluid to enter arm 2003 via opening 2007. The gastric fluid gradually dissolves or erodes the erodible insert 2036 thereby releasing the pharmaceutical or diagnostic. Once the erodible insert has eroded, the components of the GRDF are each individually sized to exit the stomach.

FIG. 15B illustrates the system when the erodible insert 2036 is partially eroded. As can be seen in FIG. 15B since opening 2007 is centrally located in arm 2003, the erosion of the erodible insert 2036 is directional erosion from the center of the erodible insert 2036 outwards to the ends of the erodible insert 2036.

Referring to FIG. 15C, once the erodible insert 2036 has eroded or dissolved substantially, the outward force on the retaining elements 20210 and 20200 decreases. After a certain amount of erosion of the erodible insert 2036, the resilience of the retaining elements 20210 and 20200 which are biased inwards overcomes the compressive force of the erodible insert 2036 such that the resilient retaining elements 20200 and 20210 may retract out of the recesses in the arm 2003 by application of an external force. The protrusions 20210a and 20200a are dimensioned such that once they are removed from the recesses in the arm 2003; the hinge assemblies 2020, 2021 are no longer retained in the arm 2003. Hinge assemblies 2020 and 2021 thereby disassemble from arm 2003.

Typically, the erodible insert is substantially eroded when at least about 60% of the erodible insert is eroded, or about at least about 70%, or about at least about 80% or about at least about 90% eroded before the compressive force of the erodible insert is reduced sufficiently to enable the retaining elements to retract out of the recesses in arm 2003. In other examples at least about 70%, at least about 80% or at least about 90% of the erodible insert must be eroded to enable disassembly of the system. The degree of erosion may correspond to the amount of pharmaceutical or diagnostic released.

Upon disassembly of hinge assemblies 2020 and 2021 from arm 2003, arms 2001 and 2002 also disassemble from another. FIG. 15D illustrates the components of the GRDF after disassembly of the GRDF. Each of the individual disassembled components may be small enough to pass through the pyloric valve into the intestines and thence out of the body. In alternative examples, the components may be further downsized for example by further disassembly or erosion so as to provide individual components small enough to pass through the pyloric valve.

FIGS. 16A-16C illustrates an alternative configuration of the GRDF illustrated in FIGS. 10 and 14 in which the biasing member is an angled elongate member. This configuration is similar to the configuration illustrated in FIGS. 10-14 and therefore only the points of difference will be described.

In the compressed configuration a first portion 2006a of the biasing member extends over arm 2003 in a similar manner to the embodiment described with respect to FIGS. 1-15 above. A second portion 2006b of the biasing member is angled with respect to the first portion 2006a of the biasing member and extends into hinge assembly 2020. When the GRDF is compressed into the compressed state, the majority of the GRDF is located in a main body 2030b of a capsule thereby retaining the GRDF in the compressed configuration. As a closing portion 2030a of the capsule is inserted over the hinge assembly 2020 into which the second portion 2006b of the biasing member extends, a priming/cocking member 2031 extending from an interior of the closing portion 2030 pushes the second portion 2006b of the biasing member to a position perpendicular to the first portion 2006a of the biasing member as shown in FIG. 16B, thereby priming/cocking the biasing member. The second portion 2006b of the biasing member is retained in position by a tooth 2040. This way of priming/cocking of the biasing member is herein called "horizontal priming". Such a mechanism, for example, obviates the need of an external cocking device.

Upon erosion of the capsule in gastric conditions, the first portion of the biasing member 2006a acts on arm 2002 in a similar manner to the example described with respect to FIGS. 10 and 11 to force the system into the expanded configuration. FIG. 16C illustrates this alternative arrangement in the expanded configuration. Thus an alternative arrangement of the biasing member has been described which facilitates compression of the GRDF and insertion into a capsule for ingestion.

Figure 17:
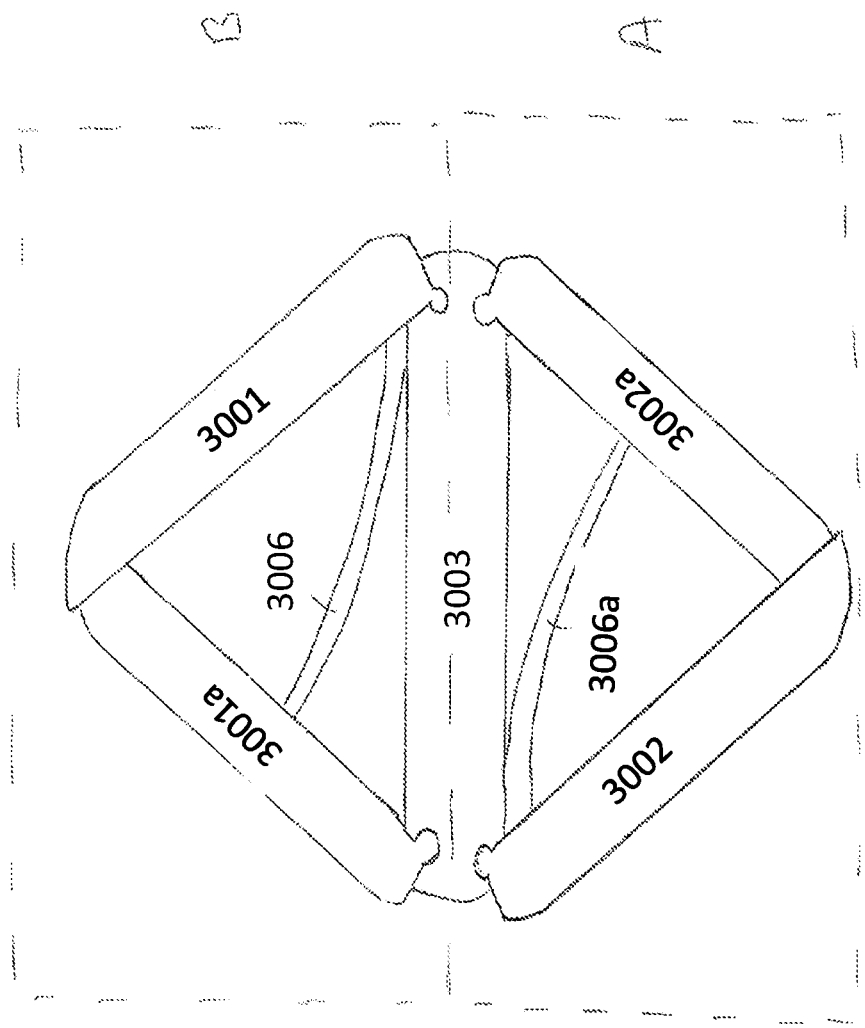
FIG. 17 is a front view of an alternative GRDF in an expanded configuration.

FIG. 17 illustrates a front view of alternative example of a GRDF according to the present disclosure in an expanded configuration. This example is substantially similar to the examples described with respect to FIGS. 1-16 above and therefore only the points of difference will be described. In this example instead of two structural arms, four structural arms are provided. Arms 3001 and 3002 are provided on one side of containing arm 3003 and arms 3001a and 3002a are provided on the other side of containing arm 3003. A second biasing member 3006a is provided to bias arms 3001a and 3002a into an expanded configuration. Arms 3001 and 3001a operate in the same manner and have the same features as arm 2001 in the example described with reference to FIGS. 10-16 above. Arms 3002 and 3002a operate in the same manner and have the same features as arm 2002 in the example described with reference to FIGS. 10-16 above. Thus arms 3001 and 3002 mechanically engage thereby locking arms 3001, 3002 and 3003 into a first triangular configuration. Similarly arms 3001a and 3002a mechanically engage thereby locking arms 3001a, 3002a and 3003 into a second triangular configuration. Thus the expanded configuration of this example includes two substantially triangular configurations, one either side of arm 3003.

Biasing members 3006 and 3006a operate in the same manner and have the same features as biasing member 2006 in the example described with reference to FIGS. 10-16 above. Biasing member 3006 biases arms 3001 and 3002 into the expanded configuration, while biasing member 3006a biases arms 3001a and 3002a into the expanded configuration. Thus, in the expanded configuration the body has an overall quadrilateral shape that includes two generally triangular shaped sections A and B (FIG. 17).

When the GRDF is compressed to a compressed configuration, arm 3001 overlays arm 3002 which itself overlays arm 3003 in a similar manner to arms 2001, 2002 and 2003 of the example described with respect to FIGS. 10-16 above. Similarly arm 3002a overlays arm 3001a which itself overlays arm 3003. Thus, a compact compressed arrangement may be provided which facilitates oral administration.

This example thus provides an alternative arrangement of a GRDF having the ability to transform between a compact compressed configuration and a strong expanded configuration that has the ability to withstand the harsh environment and gastric forces of the stomach.

In the example illustrated with respect to FIG. 17, each of arms 3001, 3002, 3001a and 3002a is straight. However, arms 3001, 3002, 3001a and 3002a could alternatively be of another shape, e.g. curved. In another alternative example, arms 3001, 3002, 3001a and 3002a may be less rigid than those illustrated such that arms 3001, 3002, 3001a and 3002a may straight in the compressed configuration but slightly curved in the expanded configuration. In such an example the overall shape in the expanded configuration may be elliptical or substantially circular. It will be appreciated that a certain amount of rigidity must be maintained in order to provide a device of sufficient strength to be maintained in gastric conditions. However a GRDF in which the mechanical engagement of arms 3001 and 3002; and 3001a and 3002a applies sufficient force to the arms to result in curvature of the arms is envisaged. Thus in the expanded configuration the GRDF may have any overall shape provided it has the size and strength to withstand gastric conditions for a required period of time.

Thus examples of a GRDF that can be retained in the stomach and disassemble after a predetermined time have been described with respect to FIGS. 1-17. In the above described examples, the length of time taken for the erodible insert to erode or dissolve acts as a timer for the disassembly of the system. In this manner the length of time the system can be retained in the stomach can be controlled by control of the erodible insert. For example, the erodible insert may be extremely resistant to erosion or dissolution so as to allow the system to be retained in the stomach for a long period of time. Alternatively the erodible insert may be less resistant to erosion or dissolution and thus the system may only be retained in the stomach for a short period of time. In some examples the erodible insert is a solid tablet. In some examples the erodible insert may be in the form of a plurality of tablets. In some examples each tablet may have the same rate of erosion/dissolution. In other examples the tablets nearest the opening may have a lower rate of erosion/dissolution and the tablets adjacent the retaining elements may have a higher rate of erosion/dissolution. In some examples, such as illustrated by tablets 2036S and 2036L in FIG. 22, the tablets may be coated by a "gastric-non-erodible" coating, allowing liquid to penetrate only through predetermined openings in the coating and/or openings in the shell such as illustrated in FIG. 21A and FIG. 21C.

In some examples, the erodible insert is configured to load relatively high levels of the active substances. For example, the therapeutic agent-containing erodible insert may comprise at least about 15%, at least about 20%, at least 30%, at least 40%, at least 50%, at least 60 wt %, at least about 70 wt % at least about 80 wt %, at least about 90 wt %, or at least about 95 wt % of active of the total weight of the erodible insert. In some examples, the erodible insert composition comprises excipients in an amount of up to and including about 90 wt %, up to and including about 80 wt %, up to and including about 70 wt %, up to and including about 60 wt %, or up to and including about 50 wt %, up to and including about 40 wt %, up to and including about wt %, up to and including about 20 wt %, up to and including about 10 wt % of the total weight of the erodible insert. Any and all closed ranges that have endpoints within any of the above-referenced ranges are also possible (e.g., between about 20 wt % and about 30 wt %).

In some examples, the erodible insert comprises about 85 wt % of active pharmaceutical ingredient and about 15 wt % of excipient, about 75 wt % of active pharmaceutical ingredient and about 25 wt % of excipient, about 65 wt % of active pharmaceutical ingredient and about 35 wt % of excipient, about 55 wt % of active pharmaceutical ingredient and about 45 wt % of excipient, about 45 wt % of active pharmaceutical ingredient and about 55 wt % of excipient, about 35 wt % of active pharmaceutical ingredient and about 65 wt % of excipient, about 25 wt % of active pharmaceutical ingredient and about 75 wt % of excipient or about 15 wt % of active pharmaceutical ingredient and about 85 wt % of excipient.

Referring to FIGS. 10, 11, 15 the location of opening 2007 is a factor in determining the rate of erosion. For example, positioning of opening 2007 in the center of arm 2003 provides a state where the distance between the opening and each end of the erodible insert 2036 is not less then half the length of the erodible insert. Thus maximum erosion must be carried out before the retaining elements retract enabling disassembly of the GRDF, thereby providing a maximum time delay before disassembly. Alternatively a plurality of openings may be provided at various locations on arm 2003, such as illustrated in FIGS. 21A and B, to increase the amount of gastric fluid entering the GRDF and thereby increase the rate of erosion. Thus the length of time which the system is retained in the stomach may be partly controlled by the arrangements and size of openings in arm 2003 as well as the shape and rate of erosion under gastric conditions of the erodible insert 2036. For example, as illustrated in FIGS. 21A and B, R1, R2, R3 R4, and R5 holes partly control extent of fluid entering the cavity. The C holes are the location for the protrusion of 20200 and 20210 to lock into the arm and should not provide any significant exposure to gastric fluid or simulated gastric fluid. In addition, the erodible insert tablets may be partially coated by a "gastric-non-erodible" coating, allowing liquid to penetrate only through predetermined openings in the coating. Coating of the erodible insert tablets and particularly the side tablets, prevents the premature exposure of the side tablets to the gastric fluid. Thus, an overlap between the opening/s in the shell such as illustrated in FIG. 21A and FIG. 21B and surface area/s on the erodible insert which lack coating ("uncoated areas" of the erodible insert), define surface areas of the erodible insert which are exposed to gastric fluid. The sum area of the surface areas of the erodible insert which are exposed to gastric fluid is herein referred to as "sum exposure area" or "sum area of the overlapping areas" or "sum area of the overlapping surfaces" or "or "sum area of the exposed surfaces".

Referring generally to FIGS. 1-22, it should be understood that any method or mechanism that is configured to maintain the collapsed configuration of the GRDF prior to swallowing is envisioned. The examples described above include a capsule that erodes or dissolves upon contact with gastric fluid. In another envisioned example, in a case where the natural state of the GRDF is the expanded state, there may be a material holding the GRDF closed which dissolves or erodes in the presence of gastric fluid thereby releasing the GRDF to an expanded configuration. In another example, the material may be in the shape of an erodible band which encompasses the arms to maintain the GRDF in a collapsed configuration until the band erodes allowing expansion of the GRDF. Still another envisioned example includes a glue-like material that keeps the two arms together until the glue-like material erodes allowing expansion of the GRDF.

In the illustrated examples above, and without wishing to be bound to theory, the capsule provides both a retention function for retaining the GRDF in a compressed configuration and a barrier function by providing a cover over the opening to the cavity thereby preventing gastric fluid entering the cavity. In alternative examples however the barrier function and retention functions may be provided by separate components. For example the opening to the cavity could be sealed by a cover and the compressed configuration could be maintained by an erodible band. Alternatively an erodible cover could be provided over the opening to the cavity and a capsule provided to retain the system in the compressed configuration. In these examples the erosion rate of the cover may be different to the erosion rate of the capsule or band. In such examples the GRDF may transform into the expanded configuration and gastric fluid would enter the cavity after a further time delay. In an alternative example, a further delay may be provided by a portion of the erodible insert or, where the erodible insert is formed from a number of erodible units, some of the erodible units may be positioned to erode first such that there is a delay in delivery of the API or diagnostic. Thus the provision of an additional cover for preventing gastric fluid entering the cavity can provide an additional delay in the delivery of the API or diagnostic and the disassembly of the system.

It should be understood that other methods or mechanisms configured to transition or open the GRDF to the expanded configuration are encompassed by the present disclosure. In the examples described herein a leaf spring springs outwards and extends from the inner area of one or both of the arms once the expanding configuration is initiated or once the mechanical integrity of the collapsed condition has been compromised, e.g., capsule is dissolved. Alternatively a rigid member in combination with a helical spring could be used instead of the leaf spring. In an alternative envisioned example, a superporous hydrogel system may be incorporated into the inner part of the arm 2002 which expands upon exposure to the gastric environment thereby forcing arm 2002 upward against arm 2001 into the expanded configuration. In a further alternative example, the pivotal connection between arms 2003 and 2002 may be formed of an elastic material such that the pivotal connection itself biases the GRDF into the expanded configuration.

As described in the examples, the mechanical engagement of arms 2001 and 2002 (or equally 1001 and 1002 or 3001 and 3002) by arm 2003 (or similarly 1003, 3003) locks the arms together into a triangular-shaped structure with the strength to withstand the forces that will act on it in the stomach and a size to prevent it passing through the pyloric valve and out of the stomach. In alternative embodiments, additional locking means may be employed to assist in locking the arms in an expanded configuration. For example, as described above, an inner facing surface of arm 2002 may include a locking mechanism to lock the leaf spring in place in the expanded configuration. Alternatively the hinge assemblies of the sealing elements or hinge assemblies may include one or more mechanical interfaces or mechanisms, gear, spring, cam, etc. that are configured to maintain or lock the GRDF in the expanded configuration until disassembly. In some examples the leaf spring may simply be configured to bias the GRDF from the collapsed configuration and not necessarily to maintain the GRDF in the expanded configuration but may be configured to simply prevent the GRDF from transitioning back to the collapsed configuration.

In the general area of unfolding gastric retentive systems, the force of opening or measure of mechanical bias towards an expanded state can be associated with a degree of safety risk in cases where unfolding or expansion occurs in an undesired location. Undesired locations include for example, the esophagus midway to stomach; in a crevice in the stomach wall or gastric rugae; or in intestine in cases where the capsule passes the pyloric valve prior to dissolving. Thus, it is of particular interest that in relation to the GRDFs disclosed herein, in one embodiment, the force of opening from the compressed configuration is significantly less than the force to compressing the GRDF from the expanded configuration. Put another way, the force of the biasing member acting to transition the GRDF from the compressed configuration into the expanded configuration is significantly less than the force required to compress the GRDF by about 10% in any dimension from the expanded configuration towards the compressed configuration. For example, the ratio of the opening force, applied by the biasing member, to the compression force, required to compress the GRDF by about 10%, is less than about 0.2 or less than about 0.1 or less than about 0.05 or less than about 0.03 or less than about 0.02. In examples, the ratio is about 0.005 to about 0.2 or 0.005 to about 0.1 or about 0.005 to about 0.05 or about 0.005 to about 0.03 or about 0.005 to about 0.02. Combinations of the above-referenced ranges are also possible. In relation to the GRDFs disclosed herein, the force to open from the compressed configuration towards the expanded configuration may be less than about 100 gF, or less than about 50 gF or between about 20 to about 300.

In the examples discussed herein, a cylindrically shaped containing or mediating arm 1003, 2003 or 3003 is described however the containing arm may have any suitable shape that includes a cavity in which an erodible insert can be located. In a similar manner, whilst particular shapes of structural arms 1001, 2001, 1002 and 2002 have been described, any suitable shape may be used provided the three arms can form a compressed configuration which is small enough to be swallowed. For example the structural arms may have a solid shape provided the depth of the arms is small enough to enable the GRDF to compress to a suitable size and shape for swallowing. In alternative examples, the structural arms may have a hollow shape in the form of an open (i.e. not enclosed) shell in a similar manner to the specific examples described above. The structural and containment arms are not limited to any particular cross sectional shape however in examples where the structural arms are in the form of a shell, the arms are shaped so that an inner surface of structural arms 1001/2001 has a corresponding shape to an outer surface of structural arm 1002/2002; and an inner surface of structural arm 1002/2002 has a corresponding shape to an outer surface of containment arm 1003/2003. By forming structural arms 1001/2001 and 1002/2002 to have internal surfaces with corresponding shapes to structural arm 1002/2002 and containment arm 1003/2003 respectively, a compact device is provided that facilitates oral administration of the GRDF.

As noted above, after a pre-determined period of time, the GRDFs described herein will eventually lose their mechanical integrity as a single unit, disassemble and pass from the stomach for subsequent evacuation. There are many possible mechanisms to achieve this result, all of which are encompassed by the present disclosure. In the illustrated examples above an erodible insert is located in arm 2003, which erodible insert disintegrates or erodes once exposed to gastric fluid thereby causing mechanical disengagement of the hinge assemblies 2020 and 2021 from arm 2003 and resulting in a dismantling of at least a first vertex.

In some embodiments, the GRDFs described herein include an arm having a cavity defined therein. The volume of the cavity may range from about 100 mm$^3$ to about 800 mm$^3$, about 300 mm$^3$ to about 600 mm$^3$ or about 350 mm$^3$ to about 550 mm$^3$. In embodiments, the volume of the cavity is about 0.8 ml to about 0.1 ml, or about 0.6 to about 0.3 ml. Depending on the compressibility of the insert tablet and the cavity design, the volume of the cavity may provide for an insert tablet comprising a dose of API in an amount of 700 mg or less, about 250 mg to about 700 mg, or about 300 mg to about 600 mg.

Figure 22:
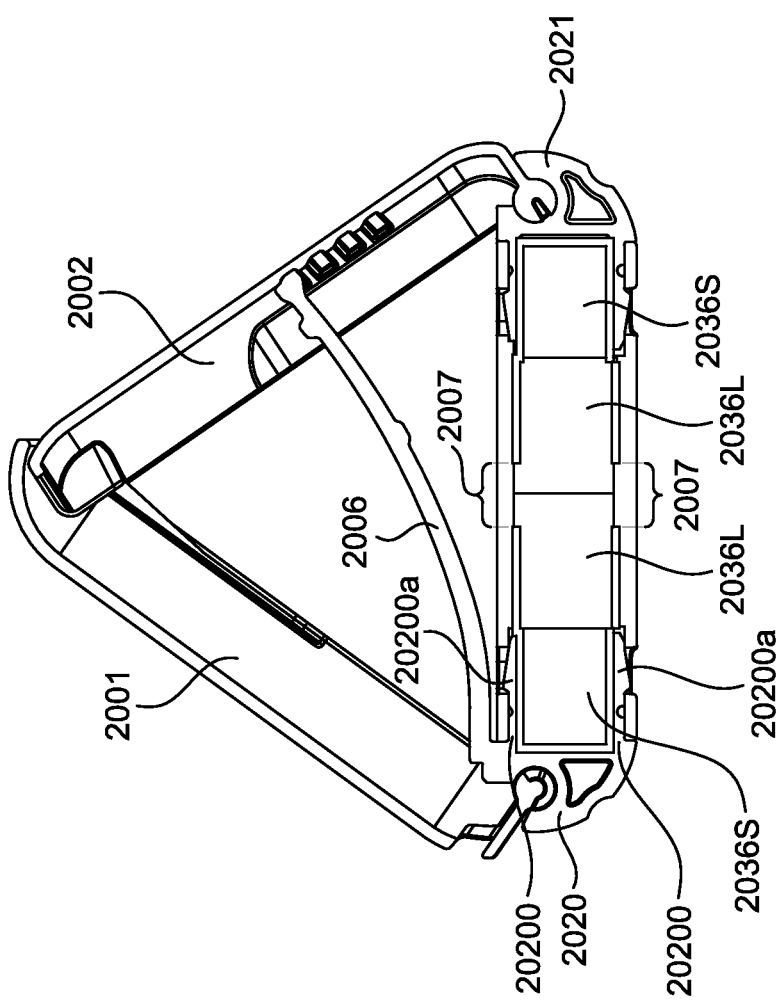
FIG. 22 is a cross-sectional view of the GRDF with the additional display of the coated erodible and openings 2007 at the top and bottom of the tube, the tablets are coated with a gastric-non-erodible coating on the surfaces that are not in contact with another tablet or with a 2007 opening.

In any of the GRDFs described herein, the erodible insert includes excipients typically used for immediate release or controlled release. However, in a preferred embodiment, controlled release excipients are included. The location and amount of exposure of the erodible insert to gastric fluid may be controlled through control of the area of the openings in the arm containing the erodible insert, such as the holes presented in FIG. 21A and FIG. 21B, as well as the location of openings in the gastric-non-erodible coating of the erodible insert tablets as shown in FIG. 22, also affecting erosion rate and/or duration.

The materials are selected and processed in a way that will enable each of the components of the GRDF to operate according to its defined functionality (e.g., rigidity for the arms and hinge, elasticity of spring, and stability in dissolution, as defined above) or desired manufacturing method (e.g. hot melt extrusion, injection molding). Different materials may be used in order to better balance between durability and safety or eventual disintegration; pH independence and dependence, etc. For example, the ratio of cellulose acetate (CA) to triacetin may contribute to the durability, elasticity, reduced brittleness, independence from pH changes and decreased erodibility. In another example, injection molded pH dependent polymer such as HPMC acetate succinate is at least partially coated with a pH dependent polymer (e.g., polymethacrylates such as HPMC acetate succinate, Eudragit S®). In another example, molded parts are a combination of pH independent and pH dependent polymer. Other materials may be selected from PCT/US2015/033850 or PCT/US2016/064439.

In some embodiments, the individual body components such as the arms, hinge, tube or sleeve do not undergo any significant swelling in the presence of biological fluids such as blood, water, bile, gastric fluids, combinations of these, or the like. For example, in certain embodiments, the individual components swells by less than about 10 vol %, less than about 5 vol %, less than about 2 vol %, or less than about 1 vol % in a non-stirred, gastric fluid or simulated gastric fluid at physiological temperature as compared to the volume of the component in the dry state (e.g., RT). For example, the molded hinge assembly or arm component may comprise enteric polymers (i.e. for example included during injection molding) and/or a coat of enteric polymers (i.e. added post molding). In another embodiment, digestive track insoluble materials, for example cellulose acetate may be used.

The GRDF of the present disclosure may be manufactured by a number of processes including injection molding, 3D printing and the like, as will be clear to one skilled in the art, and including the manufacturing techniques described in WO 2003057197 or in Zema et. al., Journal of Controlled Release, Volume 159 (2012) 324-331. For example, a mold can be constructed in the desired shape of the components of the GRDF and filled with appropriate material(s) in liquid state and then allowed to cure by chemical processes or cooled if thermosetting material(s) are used.

The ability to be minimally affected by a repetitive force contributes to the ability of a GR system to maintain a size relevant for gastric retention. In examples of the present disclosure, the GRDFs described in detail above, may include a mechanical durability to remain intact, i.e., assembled with minimum deformation/downsizing when exposed to gastric conditions or when a repetitive compressive force is applied, over a period of time of at least about 2 hours, or about 3 hours, or about 6 hours, or about 9 hours, or about 12 hours or about 24 hours, or about 168 hours, or about one month, and under gastric conditions or when a repetitive force of at least 500 grF or at least 800 gF or at least 1000 gF or at least 2000 gF is applied. In the examples described herein, the gastric retentive system is capable of substantially maintaining its size under application of at least about 500 gF, or at least about 600 gF, or at least about 700 gF or at least about 800 gF or at least about 1000 gF or about 2000 gF applied every two hours. In the examples disclosed herein, the GRDF may include a mechanical durability to maintain a size relevant for gastric retention over a period of time of at least about 2, or at least about 3, or at least about 6, or at least about 9, or at least about 12 or about 24 hours and under the application of a repetitive force ranging from about 400 gF to about 3000 grF, in embodiments from about 400 gF to about 1000 gF. In the examples described herein, the expanded state GRDF is capable of resisting about 200 to about 600 gF over the full gastric retentive period. In another example, the gastric retentive devices or systems described in detail provide a mechanical durability to maintain a size relevant for gastric retention, i.e., assembled with minimal deformation/downsizing under the application of a repetitive force in any direction or position of at least about 500 gF or at least about 800 gF or at least about 1000 gF or at least about 2000 gF over a period of time of at least 2, 3, 6, 9, 12, 24, 48, 72 hours or up to a week, a month or up to a couple of months. In this context, minimal deformation/downsizing is considered about 20% or preferably about 10% change in largest dimension.

In the illustrated examples, the GRDF provides a gastric retentive endpoint and/or opening of the closed circuit and/or disassembly of the GRDF and/or cleaving the connection between the erodible-insert containing arm and at least one of other arms. Changes in geometric and/or mechanical properties of the erodible insert compromises the closed circuit and/or disassembles the body into its parts/units, the parts/units suitable for exiting the stomach via the gastric valve thereof.

In the examples described herein, the expanded state GRDF is capable of maintaining dimensional strength and strength under repeated forces over a period of time in the gastric environment and/or until about more than 50%, 60%, 70%, 80% or 90% erosion of the erodible insert and/or until about 10%, 20%, 30%, 40%, 50%, 60%, 70%, 80%, 90% release of active ingredient. In some embodiments, the erosion of the erodible insert is at a rate similar to zero order preferably over 12 hours. Put another way the rate of erosion of the erodible insert is substantially constant.

In an embodiment, % release of API (weight/weight=w/w) of the total initial API weight per day is about 12% to 22% as measured in rotating bottle apparatus at 37° C. at 2.5 RPM having 400 mL, pH2 and Xanthan gum 0.125 gr/L. In an embodiment, % RSD is less than about 80%, or less than about 60% or less than about 40% as measured in rotating bottle apparatus at 37° C. at 2.5 RPM having 400 mL, pH2 and Xanthan gum 0.125 gr/L. In a preferred embodiment, disassembly/disengagement of the GRDF occurs at a time point equivalent to more than 80%, more than 87%, more than 90%, more than 95% or about 100% release of API.

In an embodiment, % release of API (w/w) of the total initial API weight per day is less than about 30%. In another embodiment, % release per day is less than about 25%. In another embodiment, % release per day is less than about 23%. In another embodiment, % release per day is less than about 20%. In another embodiment, % release per day is less than about 15%. In another embodiment, % release per day is about 12%. In other examples, % release per day is about from about 5% to about 30%. In another embodiment, % release per day is from about 10% to about 25%.

In another embodiment, % RSD of the % (w/w) release of API of the total initial API weight per day is less than about 80% as measured in rotating bottle apparatus at 37° C. at 2.5 RPM having 400 mL, pH2 and Xanthan gum 0.125 gr/L. In another embodiment, % RSD is less than about 60% as measured in rotating bottle apparatus at 37° C. at 2.5 RPM having 400 mL, pH2 and Xanthan gum 0.125 gr/L. In another embodiment, % RSD is less than about 40% as measured in rotating bottle apparatus at 37° C. at 2.5 RPM having 400 mL, pH2 and Xanthan gum 0.125 gr/L.

In the examples described herein, the expanded state GRDF is capable of being retained internal to a subject for extended periods of time beyond standard oral extended release dosage forms. In some embodiments, GRDF is capable of gastric retention under light meal conditions for at least 5 hours in 50% of subjects. In the examples described herein, the expanded state GRDF is capable of gastric retention under light meal conditions for 5 hours in more than 50% of subjects. Assuming one can neutralize the effect of retention caused by the light meal, the GRDF is capable of retention through at least one or preferably two cycles of gastric housekeeping forces.

In the examples described herein, the expanded state GRDF is capable of retention in a beagle dog stomach of at least 4 hours in about 50% of dogs under fasted conditions. In the examples described herein, the expanded GRDF is capable of retention in a beagle dog stomach of about 4 hours in about 50% of dogs under fasted conditions.

In the examples described herein, the expanded state GRDF is capable of gastric retention in a pig for about 4-36 hours under fasted conditions. In the examples described herein, the expanded state GRDF is capable of gastric retention in a pig for at least 36 hours under fasted conditions. In the examples described herein, the expanded GRDF is capable of retention in a pig stomach for at least 48 hours in about 83% of pigs under fasted conditions.

Optionally, in an additional example, any of GRDFs described or envisioned herein may include an emergency release feature that allows the GRDF to pass through the pyloric valve for immediate removal from the stomach and gastrointestinal tract, if needed. An antidote or other triggering mechanism may be employed to initiate the emergency release of the GRDF or gastric residence system. In one envisioned example, a GRDF of the present disclosure includes hinge assemblies (or any other portion thereof) that are pH sensitive (for example sensitive to a pH 5-5.5) such that under normal gastric conditions the system (or any portion thereof) remains intact. However, if needed, the environmental pH can be slightly increased (to within the above pH sensitive range or any other specified range) causing the mechanical integrity of the hinge assembly (or any portion thereof) to erode causing the hinge assembly to disassemble from one or both arms and pass through the pyloric valve for subsequent evacuation.

EXPERIMENTAL EXAMPLES

Example 1: Manufacture of a Gastric Retentive System

Manufacture of a system as disclosed herein is described below, according to an aspect of this disclosure.

Example 1A—Manufacture of Extruded Beads

The extruded beads were prepared using hot melt extrusion technology.

"Formulation N": cellulose acetate (400 g) and triacetin (100 grams).

"Formulation B": HPMC AS HG (1600 grams), HPMC AS MG (400 grams), PEG 3350 (44 grams) and dibutyl sebacate (176 grams).

Each of Formulation N and Formulation B was blended in a high shear mixer (DIOSNA P-25). The granules are then fed in twin-screw extruder (screw diameter 16 mm) at the rate of 1 kg/hr, screw speed of 150 RPM, melt temperature of 190° C. for Formulation N and 140° C. for Formulation B. The extrudate was cooled using air cooled conveyors and chopped into beads using a Varicut Pelletiser.

Example 1B Mold Manufacture

Molds of each of the GRDF parts were designed for use in injection molding technology. Extruded beads were fed into a Wittman EcoPower 55 Ton Injection Molding Machine using injection parameters listed in Table 1. The parts obtained are illustrated in FIGS. 10 through 15 and FIGS. 19A-19C.

TABLE 1

| Injection molding parameters | | | | | |
|---|---|---|---|---|---|
| Part Injected [shown in FIGS. 10-15 and FIG. 19A-19 C] | Barrel Temperature [° C.] | Mold Temperature [° C.] | Injection pressure [Bar] | Hold pressure [Bar] | Cycle time [sec] |
| Hinge assembly 2021 (Formulation N) | 170-215 | 65 | 1600 | 550 | 16-13 |
| Hinge assembly 2020 (including an integral biasing member*) (Formulation N) | 170-220 | 65 | 1600 | 550 | 16-13 |
| Ramp 2006r ** (Formulation N) | 170-220 | 65 | 1600 | 700 | 16-13 |
| Arms 2001, 2002 (Formulation B) | 150-190 | 55-40 | 1400 | 750-700 | 23-18 |

TABLE 1-continued

Injection molding parameters

| Part Injected [shown in FIGS. 10-15 and FIG. 19A-19 C] | Barrel Temperature [° C.] | Mold Temperature [° C.] | Injection pressure [Bar] | Hold pressure [Bar] | Cycle time [sec] |
| --- | --- | --- | --- | --- | --- |
| Arm sleeve, tube 2003 (Formulation B) | 150-190 | 60-40 | 2000 | 780-700 | 23-18 |

*In an alternate example, the biasing member could be designed as a separate part from the hinge assembly, made e.g. by injection molding. as an integral part of the biasing member

** In an alternate example, ramp 2006r could be designed as an integral part of the biasing member 2006 and/or a hinge assembly, made e.g. by injection molding.

Example 1C: Mold Coating

The arms 2001, 2002 and 2003 were coated using an O'Hara LabCoat 15" machine. The dispersion formulation is presented in Table 2. The parts were coated using the following parameters: inlet temperature of 30° C., exhaust temperature of 25° C., atomizing air pressure of 1.5 bars, spray rate of 7-10 g/min and pan speed of 14-18 RPM. A coating weight gain of 5.0% was applied to the parts. Curing step was done for half an hour at inlet temperature of 40° C.

TABLE 2

Enteric coating formulation

| Component | Quantity [g] |
| --- | --- |
| Dibutyl Sebacate | 27 |
| Ferric oxid red | 8 |
| Talc extra fine | 52 |
| Eudragit ® S-100 (Methacrylic Acid copolymer, Type B) | 312 |
| Isopropyl Alcohol | 3480 |
| Acetone | 870 |

Example 1D Erodible Insert Tablet Manufacturing

Erodible insert 2036 was made up of two types of tablets for a total of four units: two side tablets (2036S, FIG. 19D) for inclusion at either end of the sleeve or tube 2003 and two central tablets (2036L, FIG. 19D) placed in the center between the side tablets. Each punch was designed to fill the cavity of the GRDF. The tablets were produced using wet granulation.

The formulation of the central tablets and side tablets are presented in Table 3. The intra-granular excipients were mixed in high shear mixer (Diosna P-10). The granulation solution (purified water) was added to the high shear mixer during mixing. The obtained granulate was then dried using a fluid bed drier (FBD), milled using milling machine (Quadro 0.032") and blended together with the extra-granular excipients using blender (Y-cone 5L).

TABLE 3

Tablet formulation 1

| | Quantity [g] | |
| --- | --- | --- |
| Component | Side tablet (2036S) | Central tablet (2036L) |
| Intra-granular material | | |
| Povidone (PVP K-90) | 156.8 | 276.0 |
| Mannitol USP (PEARLITOL ® 200SD) | 9.5 | 412.8 |
| Barium Sulfate USP | 1237.5 | 1237.2 |
| Ethocel ™ Premium 7 CPS | 668.3 | 408.0 |
| Granulation solution (purified water)* | 210 | 210 |
| Extra-granular materials | | |
| Mannitol USP (PEARLITOL ® 200SD) | 255.1 | 277.2 |
| Magnesium Stearate | 25.8 | 28.8 |

*evaporated during drying

Tablet Formulation 1: The final blend was compressed into tablets using a tablet press (Fette 102) (each central tab weighed 220 mg and each side tablet weighed 160 mg).

Example 1E Mold Labelling

The 2001, 2003, 2020, 2021 were manually labelled with Barium sulphate for detection in X-ray. Barium sulphate were manually placed on the 2001, 2020, 2021 and 2003 (about 20-25 mg for each part) and then sealed using a cellulose acetate solution 6.5% W/V in acetone.

All labelled parts were then dried at room temperature.

Example 1F Assembly of GRDF, FIG. 10

The ramp 2006r was attached to the 2003 sleeve using 6% W/W cellulose acetate solution in acetone (100μ). Arms 2001 and 2002 were lubricated using Magnesium stearate powder. The insert erodible tablets 2036 were placed in the 2003 sleeve in the following order: one 2036S on each end and two 2036L in the centre. Hinges 2020 and 2021 were then manually connected to respective arms 2001 and 2002. The final GRDF was stored in HDPE bottles with silica until dosing. Before in vivo dosing or in vitro testing, assembled GRDF were folded and placed in a capsule000 in an elongated state, as presented in FIG. 16A.

Example 2—In Vitro Characteristics

For the purposes of this example, in order to disassociate the effects of the erodible insert, the hinges 2020 and 2021 were glued to opposing ends of the 2003 arm [FIG. 10].

For the purposes of this example, the opening force is the minimum force applied by the GRDF to open from the compressed configuration, as illustrated as F1 in FIGS. 20A and 20B. In order to measure the minimum opening force, F1, the minimum weight applied at W on the compressed structure (which was placed on a rigid surface), which resulted in slight opening was measured for both a comparative example and the test article described above, see FIG. 20A, Results are presented in Table 4.

For the purposes of this example, the rigidity of a device is a measure of a device's ability to resist change despite application of a force of compression, F2 in FIGS. 20C and 20D. F2 is calculated by measuring the minimum force which is applied for 30 seconds and which is required to cause a 10% decrease in the height of the expanded state gastric retentive at room temperature. Four systems were tested and results are presented in Table 4.

Comparative device B: GRDF in FIGS. 20A and 20C* (additional details of design are disclosed in PCT/US2015/033850, example 6—FIG. 18, 34B), using material from Formulation B Comparative device N: GRDF in FIGS. 20A and 20C* (additional details of device design are disclosed in PCT/US2015/033850, example 6—FIG. 18, 34B), using material from, using material from Formulation N GRDF B: GRS of Example 1—Formulation B
GRDF N: GRS of Example 1—Formulation N

TABLE 4

Results

| Force | Comparative device B | Comparative device N | GRDF B | GRDF N |
|---|---|---|---|---|
| Opening force F1 (grF) as measured by sensor | 180 | 285 | 30 | 50 |
| Rigidity as measured by minimum Force F2 required to cause > 10% in height against (grF) as measured by sensor | 700 | 850 | 2500 | 4000 |
| Ratio of F1/F2: | 0.257 | 0.335 | 0.012 | 0.013 |

Example 3—Beagle Dog Study

Protocol

Five Beagle dogs [12-15 kg] were enrolled in the study. All animals were evaluated over 3 days of repeat, sedated dosing after overnight fasting. The test article as described in Example 1 was endoscopically dosed directly to the stomach cavity. Immediately following dosing, ~80 ml of water (room temp) was administered via the endoscope directly to the stomach cavity. Approximately 5 minutes later, dosing fluoroscopy was performed to evaluate GRDF location and condition (open or closed). If the GRDF had not opened, an additional fluoroscopy evaluation was performed at ~15 minutes post-dosing. The following fluoroscopy follow up schedule was employed after the first and final dosing: 4h, 8h, 12h, 24h, 36h and 48h for a total of 5 days±2 days following the final dosing or until the test sample left the stomach cavity. Approximately 5 hours following a dose, the animals were fed a ~150 kcal meal. Prior to fasting, for a minimum of 12 hours, the animals were provided a meal of at least ~300 kcal or normal PM rations if exceeding 300 kcal.

On ~Day 7 the animals underwent final fluoroscopy imaging.

Safety Results:

All animals were generally healthy throughout the duration of the study without gastrointestinal irritation and/or injury observed in the GI. There was no premature emptying of encapsulated test product from the stomach. Fecal Occult Blood Test (FOBT) was negative prior to and at end of the study. Feces was collected at least once a day, and the collected feces was examined for remnants of the test article; which were assessed for the physical state and then photographed, collected, and returned to the Sponsor after the end of the study. No abnormal feces were noted. The biodegradable components of the test article were noted to be very soft or almost completely eroded.

Results:

TABLE 5

Results of Dog Study

| Parameter | Dogs |
|---|---|
| Meal condition | Fasted |
| % Gastric retentive system expanded and assembled in stomach | 50% (5/10) at 4 hr* 0% (0/10) at 8-36 hr |
| Premature emptying from stomach into the intestine of expanded form | None |

TABLE 5-continued

Results of Dog Study

| Parameter | Dogs |
|---|---|
| % Gastric retentive system disassembled in GI (prior to exiting animal) | 50% (5/10) at 4 hr* 60% (6/10) at 8 hr 33% (5/15) at 12 hr 13% (2/15) at 24 hr 10% (1/10) at 36 hr |

*based on 2 or 3 doses

Example 4—Pig Study

Protocol

Twelve Yorkshire pigs were divided into two treatment groups, test and control, with a total of 6 animals (3 male, 3 female) evaluated over 5 days of repeat, sedated dosing after overnight fasting. The test article as described in Example 1 was dosed via gastric tube directly to the stomach cavity. Immediately following dosing, ~200-250 ml water (room temperature) was administered via the gastric tube directly to the stomach cavity. Approximately 5 minutes later, the dosing fluoroscopy was performed to evaluate device location and condition (open or closed). The fluoroscopy follow up schedule was employed after the first and final dosing: 4h, 8h, 12h, 24h (immediately following 2nd dose), 36h, and 48h (immediately following 3rd dose). Approximately hours after a dose, the animals were fed normal AM feed rations. Prior to fasting, for a minimum of 12 hours, the animals were provided with normal PM feed rations.

Feces monitoring and collection occurred at least twice daily during the in-life duration. Collected feces were examined for test article remnants, and continued until either all remnants were recovered or the animal was terminated.

On ~Day 7 the animals underwent final fluoroscopy imaging and euthanized for a complete necropsy. Tissues were collected for further histological analysis.

TABLE 6

Results of Pig Study

| Parameter | Pigs |
| --- | --- |
| Meal condition | Fasted |
| % Gastric retentive system expanded and assembled in stomach | 100% (6/6) at 4-36 hr*<br>83% (5/6) at 48 hr |
| Premature emptying from stomach into intestine of expanded form | None |
| % Gastric retentive system disassembled in GI (prior to exiting animal) | 0% (0/6) at 4-36 hr*<br>17% (1/6) at 48 hr |

*based on first dose

Example 5—Human Study

A single centre, single dose, two-cohort, open-label study was approved by the IRB and conducted according to GCP with informed healthy subjects (males and females, aged 50-years, total n=12). Cohort 1 (n=4) went through a single period under light meal condition, Cohort 2 (n=8) had a randomized 2-period, 2-way-cross-over design with 2 different meal conditions (i.e. light and moderate meal).

After an overnight fast of >10 hrs, subjects had to complete either a light caloric breakfast (130 kcal, 21% fat) within 20 min or a moderate caloric breakfast (552 kcal, 48% fat) within 45 min, depending on the respective Cohort/Period. Immediately after breakfast (at 20 or after start of light or moderate fat breakfast, respectively), a single dose of the test product described in Example 1 was administered orally to each subject with a glass of water.

In light meal test arm, a lunch (500 kcal) and a dinner were served at 5 hrs and 10 hrs post dose (herein "pd"), respectively. In periods under moderate meal conditions, a lunch (862 kcal) and a dinner were served at 4 hrs and 10 hrs pd, respectively.

Serial X-Ray Imaging and/or Fluoroscopy Scans were performed pd to confirm and document anatomical location and state of test product X-ray images were conducted with a fluoroscopy device at 0.167, 5, 8, and 10 hrs pd. Fluoroscopy only was performed at 4, 7 and additionally at 15 hrs pd if gastric retention (GR) was demonstrated at 10 hrs pd.

Results

Capabilities of expanded and assembled test product: The number of subjects with test product in expanded and assembled state in stomach and intestine are shown in Table 7.

Figure 18B:
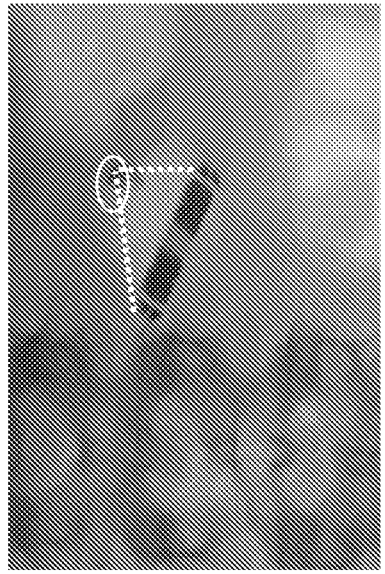
FIGS. 18A-18C are x-ray imaging photographs of an exemplary residence structure according to one example in the GI of a human subject.
Figure 18C:
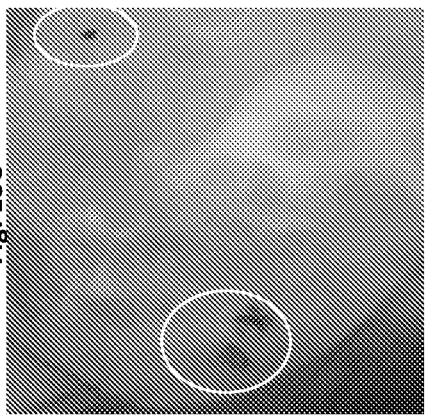
Figure 18A:
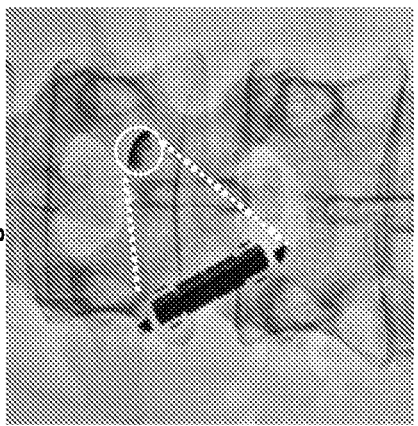

The test products, in expanded and assembled state, were capable of enduring the conditions of healthy subjects' stomach under different meal conditions after a single dose. FIGS. 18A-18C are a series of x-ray imaging photographs taken after 10 minutes (FIG. 18A), 4 hours (FIG. 18B), and 24 hours (FIG. 18C) post swallowing.

TABLE 7

Results of Human Study

Number of subjects with assembled or downsized test product over time

| Test product/<br>Time point | Light meal condition [n=12] | | Moderate meal condition [n=8] | |
| --- | --- | --- | --- | --- |
| | Expanded state in stomach | Expanded state in intestine | Expanded state in stomach | Expanded state in intestine |
| 10 min | 12 | 0 | 8 | 0 |
| 4 hrs | 6 | 1 | 3 | 1 |
| 5 hrs | 6 | 1 | 3 | 1 |
| 7 hrs | 4 | 1 | 1 | 1 |
| 8 hrs | 3 | 0 | 1 | 1 |
| 10 hrs | 2 | 0 | 1 | 1 |
| 15 hrs | 1 | 0 | 1 | 1 |

Safety and tolerability after a single dose to healthy subjects were acceptable and no serious adverse events occurred. All GRDFs eventually downsized for safe passage through the downstream intestinal tract.

Example 6—Manufacture of a GRDF for Extended Oral Release

Manufacture of a GRDF as disclosed herein is described below, according to an aspect of this disclosure.

Example 6A—Manufacture of Extruded Beads

The extruded beads were prepared using hot melt extrusion technology.

"Formulation N": cellulose acetate (4000 g) and triacetin (1000 grams): Formulation N was blended in a high shear mixer (DIOSNA P-25). The granules are then fed in twin-screw extruder (screw diameter 16 mm) at the rate of 1 kg/hr, screw speed of 150 RPM, melt temperature of 190° C. for Formulation N. The extrudate was cooled using air cooled conveyors and chopped into beads using a Varicut Pelletiser.

Example 6B Mold Manufacture

Molds of each of the GRDF parts were designed for use in injection molding technology. Extruded beads were fed into a Wittman EcoPower 55 Ton Injection Molding Machine using injection parameters listed in Table 1. The obtained parts are illustrated in FIGS. 10 through 15, FIGS. 19A-19C and FIG. 21.

TABLE 8

Injection molding parameters

| Part Injected [shown in FIGS. 10-15 and FIG. 19A-19C, FIG. 21] | Barrel Temperature [° C.] | Mold Temperature [° C.] | Injection pressure [Bar] | Hold pressure [Bar] | Cycle time [sec] |
|---|---|---|---|---|---|
| Hinge assembly 2021* (Formulation N) | 170-215 | 65 | 1600 | 550 | 16-13 |
| Hinge assembly 2020* (including an integral biasing member**) (Formulation N) | 170-220 | 65 | 1600 | 550 | 16-13 |
| Ramp 2006r *** (Formulation N) | 170-220 | 65 | 1600 | 700 | 16-13 |
| Arms 2001, 2002 (Formulation N) | 170-220 | 65-50 | 1000-1600 | 700-850 | 23-18 |
| Arm sleeve, tube 2003 (Formulation N) | 150-190 | 50-40 | 2000-2500 | 1100-1300 | 22-17 |

*width of shoulder of 2020a and 2021a was minimized to 180 μm
**In an alternate example, the biasing member could be designed as a separate part from the hinge assembly, made e.g. by injection molding.
*** In an alternate example, ramp 2006r could be designed as an integral part of the biasing member 2006 and or a hinge assembly, made e.g. by injection molding.

Example 6C(a): Tablet Manufacturing

In a particular example, erodible insert 2036 was made up of two types of tablets for a total of four units: two side tablets (2036S, FIG. 11, 19D, 22) for inclusion at either end of the sleeve or tube 2003 and two central tablets (2036L, FIG. 11, 19D, 22) placed between the side tablets. Each punch was designed to fill the cavity of the GRDF. The tablets were produced using wet granulation.

Two alternative formulations of the central tablets and two alternative formulations of side tablets are presented in Table 9. The intra-granular excipients were mixed in high shear mixer (Diosna P-10 The granulation solution (purified water) was added to the high shear mixer during mixing. The obtained granulate was then dried using a fluid bed drier (FBD), milled using milling machine (Quadro 0.032″) and blended together with the extra-granular excipients using blender (Y-cone 5L).

TABLE 9

Tablets' formulations

| | Quantity [mg/tab] | | | |
|---|---|---|---|---|
| Component | Side tablet (2036S) 2.2% Methocel ® R-15628S | Side tablet (2036S) 3% Methocel ® R-15641S | Central tablet (2036L) 2.2% Methocel ® R-15628L | Central tablet (2036L) 4% Methocel ® R-15642L |
| Intra-granular materials-units in mg (% per tablet) | | | | |
| Levodopa | 75 (56%) | 75.7 (56%) | 101 (56%) | 101 (56%) |
| Carbidopa (C) | 19.7 (14.7%) | 19.6 (14.5%) | 26.3 (14.6%) | 14.6% |
| Entacapone | 18.2 (13.6%) | 18.2 (13.5%) | 24.3 (13.5%) | 24.3 (13.5%) |
| Methocel ® (HPMC E4M) | 3 | 4.1 | 4 | 7.3 |
| Starch | 6 | 6 | 8 | 8 |
| Granulation solution (purified water)* | | | | |
| Extra-granular materials | | | | |
| Magnesium stearate NF | 1.2 | 1.2 | 1.6 | 1.6 |
| Microcrystalline cellulose (Avicel ®) | 8.6 | 7.4 | 11.5 | 7.8 |
| Sodium starch glycolate | 2.4 | 2.7 | 3.2 | 3.8 |
| Total weight | 134.1 | 134.9 | 179.9 | 180 |
| % API in formulation | 84.2 | 84.1 | 84.3 | 84.2 |

*evaporation during drying

The final blend was compressed into tablets using a tablet press (Fette 102) (each central tab weighed 180 mg and each side tablet weighed 135 mg).

Example 6C(b): Tablet Coating

In an attempt to control the direction and the rate of erosion of the erodible insert, the tablets were partially coated with enteric coating. The extent and placement of the coating allowed control of the location and area of exposure of the tablets to gastric fluid. In the current example, gastric fluid penetration was aimed to occur at the central openings of sleeve 2003, resulting in directional erosion from the centre towards the two ends of the sleeve: erosion of the central tablets (2036L) first, followed by erosion of the side tablets (2036S). It's likely that premature erosion of the side tablets would result in premature disengagement of the hinge assembly and disassembly of the GRDF before the central tablets are eroded. Coating of certain surfaces on the tablets and particularly the side tablets 2036S is aimed to prevent the premature exposure of the side tablets 2036S to gastric fluid.

The two side tablets 2036S, and two central tablets 2036L (FIG. 11, 19D, 22) were coated with the enteric coating formulation as described below and in Table 10, to reach about 5% weight gain, based on tablet weight.

Enteric Coating Formulation Preparation:

Part I: Eudragit S® was mixed in acetone and IPA solutions until dissolved. Part II: In parallel, dibutyl sebacate, talc and sieved col. ferric oxide (60 mesh) were added to the acetone and isopropyl solution mixture and mixed with a Silverson mixer homogenizer. After thorough mixing, the dispersion was sieved through a 100 mesh. The result was then combined with the Eudragit S® solution of Part I and mixing was continued until coating.

TABLE 10

| Enteric coating formulation | |
|---|---|
| Raw Materials | weight * (gr) |
| Part 1 | |
| Eudragit S-100 ® (METH.ACID&METH. | 312 |
| Acetone NF/PH.EUR | 630 |
| Isopropyl Alcohol USP | 2520 |
| Part II | |
| Ferric oxide red col. NF. | 8.15 |
| Talc USP Extra Fine | 52.5 |
| Dibutyl Sebacate NF | 27.3 |
| Acetone NF/PH.EUR | 240 |
| Isopropyl Alcohol USP | 960 |
| Weight (in excess) | 4749.95 |

* weight in excess to coat at least 550 tablets coating

Coating was performed in a vector coater coating machine with the following settings: inlet temperature: 32-30° C., outlet temperature: 25° C. (target), drum speed: 14-18 RPM, nozzle pressure: 1300 PSI, spray rate: 8-12 mL/min.

At 5% tablet weight gain, curing was performed with an inlet setting of 40° C. for about 30 min. The coating is illustrated by the bolded lines of 2036S and 2036L, FIG. 22.

Coating was then removed from the sides of the tablets which form an interface between the tablets (FIG. 22) via filing the coating layer. In addition, uncoated areas were formed to overlap with central openings in the arm sleeve, as illustrated in FIG. 22.

Example 6D—Assembly of GRDF

The ramp 2006r was added to the 2003 arm sleeve using the cellulose acetate solution described in Example 1A. Arms 2001 and 2002 were lubricated using Magnesium stearate powder. The tablets were placed in the 2003 sleeve in the following order: one 2036S on each end and two 2036L in the centre, wherein filed faces of each tablet were in contact with one another. Hinge assemblies 2020 and 2021 were then manually connected to respective arms 2001 and 2002 using the cellulose acetate solution (6% w/w solution of cellulose acetate in acetone). The final GRDF was stored in HDPE bottles with silica until testing or dosing. Before in vitro testing, assembled GRDFs were folded and placed in a capsule (size 000) in an elongated state, as presented in FIG. 16A.

Example 7: In Vitro Dissolution of Actives from GRDFs: Comparing Actives, Tablet Formulations and Sum Exposure Area The dissolution of API over time was evaluated using a rotating bottle apparatus at 37° C. at 2.5 RPM having 400 mL, pH2 and Xanthan gum 0.125 gr/L.

The rate of release of active was tested for the GRDFs in example 6, having varying erodible tablet formulations as presented in Tables 9 and 11, as well as varying sum exposure areas resulting from variation in opening sizes in the sleeve as shown in FIG. 21 and Table 11 (sum exposure area) as well as tablet coating as presented in Table 11 (R Holes exposure status). The following parameters calculated: average % release per day, standard deviation and relative standard deviation (standard deviation divided by average=% RSD).

Example 7a: In Vitro Dissolution of Entacapone from GRDF

Figure 23:
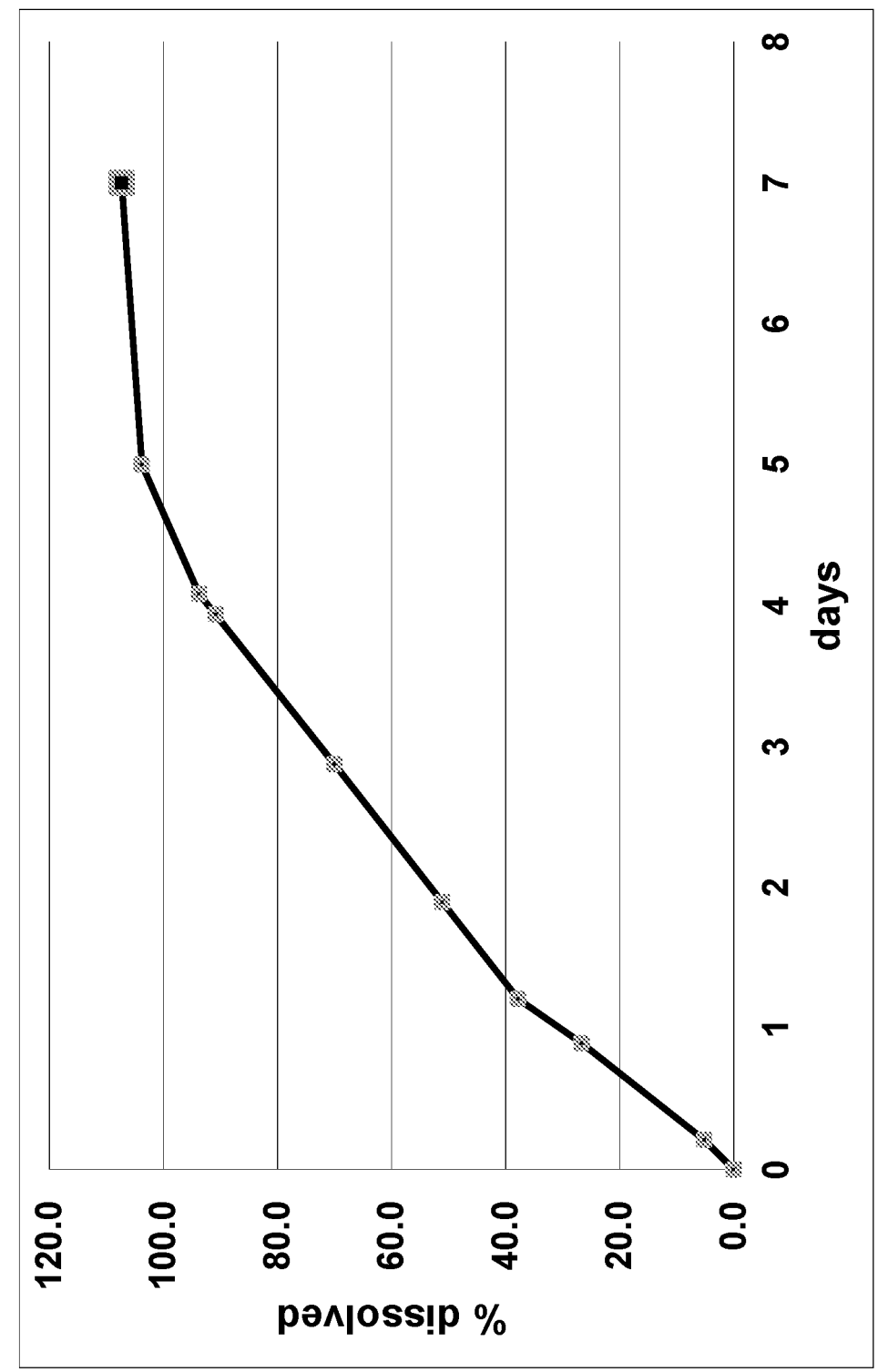
FIG. 23 is a graph displaying the results of Example 7a as a percent release of a therapeutic agent (Entacapone) over time in days as measured in rotating bottle apparatus at 37° C. at 2.5 RPM having 400 mL, pH2 and Xanthan gum 0.125 gr/L.

Percent dissolution of entacapone was calculated at the following time points: 0.0, 5.0, 21.5, 29.0, 45.5, 69.0, 94.5, 98.0, 120.0 and 168.0 hours. Test conditions, percent active release at disassembly and time of disassembly are presented in Table 11. The mean release of API per day, stdev (% release per day) and % RSD are presented in Table 12. Accumulated % release of Entacapone over time is shown in FIG. 23 and in Table 13.

Examples 7b, 7c and 7d: In Vitro Dissolution of Levodopa and Carbidopa from GRDF Percent dissolution was calculated at the following time points: 0.0, 16.0, 23.0, 41.0, 47.0, 64.0, 71.0, 87.0, 95.0, 113.0, 158.0 and 168.0 hours. In an attempt to simulate forces acting on a GRDF in vivo, five tests per day were conducted, wherein a weight of 600 gr was applied at each of the three apices of the triangular GRDF for 2 seconds×10 times per test.

Figure 24:
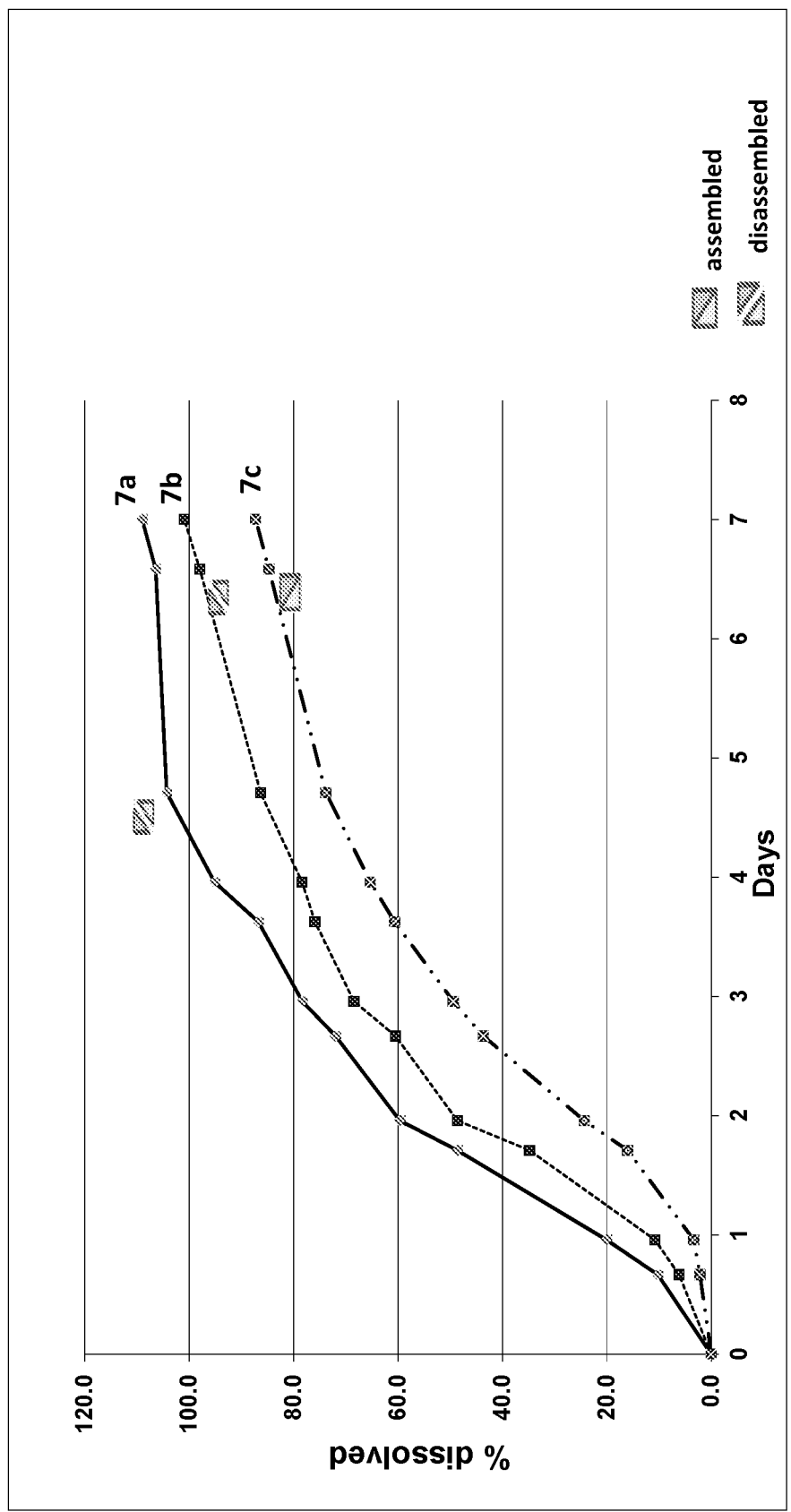
FIG. 24 is a graph displaying the results of Examples 7b, 7c and 7d as a percent release of therapeutic agents (Levodopa and Carbidopa) over time in days as measured in rotating bottle apparatus at 37° C. at 2.5 RPM having 400 mL, pH2 and Xanthan gum 0.125 gr/L.

Test conditions, percent active release at disassembly and time of disassembly are presented in Table 11. The mean release of API per day, stdev (% release per day) and % RSD are presented in Table 12. Accumulated % release of Levodopa and Carbidopa over time is presented is in FIG. 24 and in Table 14.

TABLE 11

GRDF assembly configuration, timing of disassembly and dissolution characteristics

| Example | Central tablet [203 6L] Formulation | Side tablet [2036S] | 2003 sleeve type based on R hole size in FIG. 21 | Sum exposure area (mm²) | R Holes exposure status (fully exposed, partially sealed)* | % API release at point of disassembly | Timing of disassembly |
|---|---|---|---|---|---|---|---|
| 7a | R-15628L | R-15628S | M | 20.4 | Partially sealed | not measured | not measured |
| 7b | R-15642L | R-15641S | L | 59.8 | Fully exposed | Approximately 100% (at least 95%) | 112 hr |
| 7c | R-15642L | R-15628S | M | 40.7 | Fully exposed | Approximately 98% (>95%) | 158 hr |
| 7d | R-15642L | R-15628S | S | 15.5 | Partially sealed | At least 80% | >200 hr |

*A partially sealed status is obtained when tablet/erodible insert surface areas facing at least some of the "R holes" (FIG. 21) are coated by an enteric coating. A fully exposed status is obtained when all the tablet/erodible insert surface areas facing "R holes" are uncoated.

TABLE 12

% API release/day, mean release/day, Stdev/day and % RSD for examples 7a-7d

| Day | Example 7a | Example 7b | Example 7c | Example 7d |
|---|---|---|---|---|
| 1 | 29.8 | 20.9 | 11.2 | 3.5 |
| 2 | 24.4 | 39.5 | 37.8 | 20.9 |
| 3 | 19.3 | 18.7 | 19.8 | 25.2 |
| 4 | 19.6 | 16.8 | 10.0 | 15.9 |
| 5 | 21.1 | 12.2 | 10.6 | 11.3 |
| 6 |  |  | 6.2 | 5.8 |
| 7 |  |  | 7.1 | 6.1 |
| Mean (% release/day) | 21.1 | 21.6 | 14.7 | 127 |
| Stdev (% release/day) | 6.56 | 10.50 | 11.10 | 827 |
| % RSD | 31.17 | 48.52 | 75.66 | 65.24 |

TABLE 13 accumulated release of active in example 7a

| Day | % |
|---|---|
| 0.0 | 0.0 |
| 0.9 | 26.7 |
| 1.9 | 51.1 |
| 2.9 | 70.0 |
| 3.9 | 90.9 |
| 5.0 | 103.8 |

TABLE 14 accumulated release of active in examples 7b-7d

| Day | Example 7b (timed disassembly about 4.7 days) % | Example 7c (timed disassembly about 6.6 days) % | Example 7d (timed disassembly > 8.3 days) % |
|---|---|---|---|
| 0.0 | 0.0 | 0.0 | 0.0 |
| 1.0 | 20.1 | 10.8 | 3.4 |
| 2.0 | 59.7 | 48.6 | 24.3 |
| 3.0 | 78.3 | 68.4 | 49.4 |
| 4.0 | 95.1 | 78.4 | 65.3 |
| 4.7 | 104.3 | 86.3 | 73.8 |
| 6.6 |  | 98.0 | 84.7 |
| 7.0 |  |  | 87.3 |

As presented in Tables 11-14, the GRDF of the present invention was able, in the simulated model, to retain its integrity (equivalent to retention in the stomach) for 112 hours (about 4.7 days) 158 hours (about 6.6 days) and more than 200 hours (more than about 8.3 days). Therefore, the ability of the GRDF of the present invention to retain in the stomach for about 4.7 days, about 6.6 days and more than 8.3 days was demonstrated.

Percent release of API (weight/weight=w/w) of the total initial API weight per day was about 10% to 25%, or about 12% to 22% (or less than about 30%, or less than about 25%, or less than about 20%, or less than about 15%, or about 12%).

Percent RSD of the % release of active pharmaceutical ingredient (API) of the total API per day was about 31% as measured in rotating bottle apparatus at 37° C. at 2.5 RPM having 400 mL, pH2 and Xanthan gum 0.125 gr/L in example 7a. In example 7b, % RSD was about 49% as measured in rotating bottle apparatus at 37° C. at 2.5 RPM having 400 mL, pH2 and Xanthan gum 0.125 gr/L. In example 7c, % RSD about 76% as measured in rotating bottle apparatus at 37° C. at 2.5 RPM having 400 mL, pH2 and Xanthan gum 0.125 gr/L. In example 7c, % RSD was about 65% as measured in rotating bottle apparatus at 37° C. at 2.5 RPM having 400 mL, pH2 and Xanthan gum 0.125 gr/L.

Percent RSD (w/w) was less than about 80%, or less than about 70% or less than about 50% or less than about 40% or less than about 35% as measured in rotating bottle apparatus at 37° C. at 2.5 RPM having 400 mL, pH2 and Xanthan gum 0.125 gr/L.

The time of disassembly in examples 7b-7d seemed to be connected to the sum exposure area. Using the indicated formulations, the smallest sum exposure area tested (15.5 mm2) allowed more than about 8.3 days of maintaining of the integrity of the GRDF, simulating retention in the stomach. Sum exposure area of 59.8 mm2 allowed about 4.7 days of GRDF integrity the described model, simulating retention in the stomach. Sum exposure area of 40.7 mm2 allowed about 6.6 days of GRDF integrity, simulating retention in the stomach. Mechanical disassembly of the GRDF occurred at a time point equivalent to at least 70% (w/w), at least 80% (w/w), at least 87% (w/w), at least 95% (w/w), at least 98% (w/w) or about 100% API release from the erodible insert. As the dispersion of API in the erodible insert in this example was generally homogenous, is should be assumed that API release was correlated, similar or very similar to the % erosion of the erodible insert.

Therefore, enteric coating of the tablets, as well as adjusting the location and size of the openings in the shell of the mediating arm, improved the control over the rate of erosion of the erodible insert, and the GRDF mechanical disassembly. Alignment of the uncoated areas on the erodible insert with the openings in the shell of the mediating arm, defined specific overlapping areas which were exclusively exposed to gastric fluid, and provided extended retention in the stomach for periods of time longer than had been demonstrated before.

To note, coating of the tablets has advantages for the manufacturing process as well, such as allowing the use of standard formulating methods (e,g. tableting methods) to produce the insert tablet/s or other dosage forms, as well as the free choice of APIs and excipients regardless of sensitivity to heat, pH, etc. In addition, physical separation between tablets is enabled using optionally separate coating of each tablet, allowing the inclusion of adjacent tablets containing APIs and/or excipients that are chemically or physically incompatible. To note, each tablet or other dosage form forming the erodible insert can include one or more than one APIs.

Example 8: Self-Priming GRDF

In some embodiments, priming of the biasing member as presented in FIG. 16 has the limitation that it should be conducted prior to administration to the subject. A mechanism is presented which allows preservation of the GRDF in a compressed and primed state, e.g. in the capsule, for an extended shelf-life.

Figure 25:
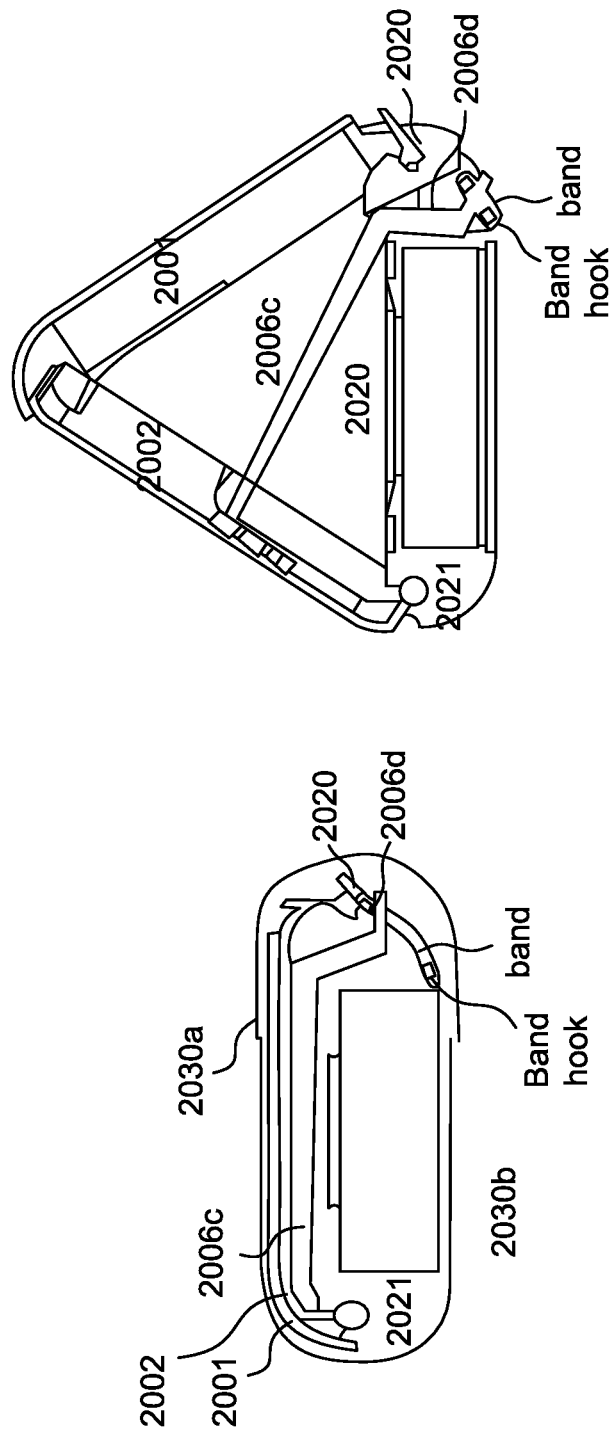
FIG. 25 is a cross-section view of the GRDF including an elastic element in the compressed and expanded configurations.

FIGS. 25A-B Illustrate an alternative configuration to the GRDF configuration as presented in FIG. 16. In the compressed configuration, portion 2006c of the biasing member extends over arm 2003 in a similar manner to the embodiment described with respect to FIGS. 1-15 above. A second portion 2006d of the biasing member is angled with respect to the first portion 2006c of the biasing member and extends into hinge assembly 2020. A hook is connected to portion 2006d of biasing member and another hook is connected to hinge assembly 2020. An elastic element exemplified here by a band as presented in FIG. 25, is stretched between these two hooks. The elastic element is made of materials having elastic properties such that when the band is stretched, the band maintains its elastic properties with minimal to no plastic deformation, also maintaining the moments needed to unfold the GRDF. Adequate materials to be used in the elastic element, e.g. a band are exemplified by silicon rubber, which mechanical properties are described in Table 15. Other materials with mechanical properties similar to properties described in Table 15, and/or having the quality of maintaining elastic properties upon stretch with minimal to no plastic deformation could also be used, as will be appreciated by the person skilled in the art.

While the GRDF is in a compressed configuration, the GRDF is maintained in a cocked/primed state (FIG. 25A). The stretching of the band in this configuration exerts a momentum on portion 2006d of the biasing member, creating a momentum of 2006c on arms 2001 and 2002 to unfold the GRDF into the expanded configuration, while the external capsule 2030 resists this momentum and keeps the GRDF in its compressed configuration. Once capsule 2030 dissolves, the momenta exerted on portions 2006d and 2006c of the biasing member leads to unfolding of the GRDF.

Figure 26:
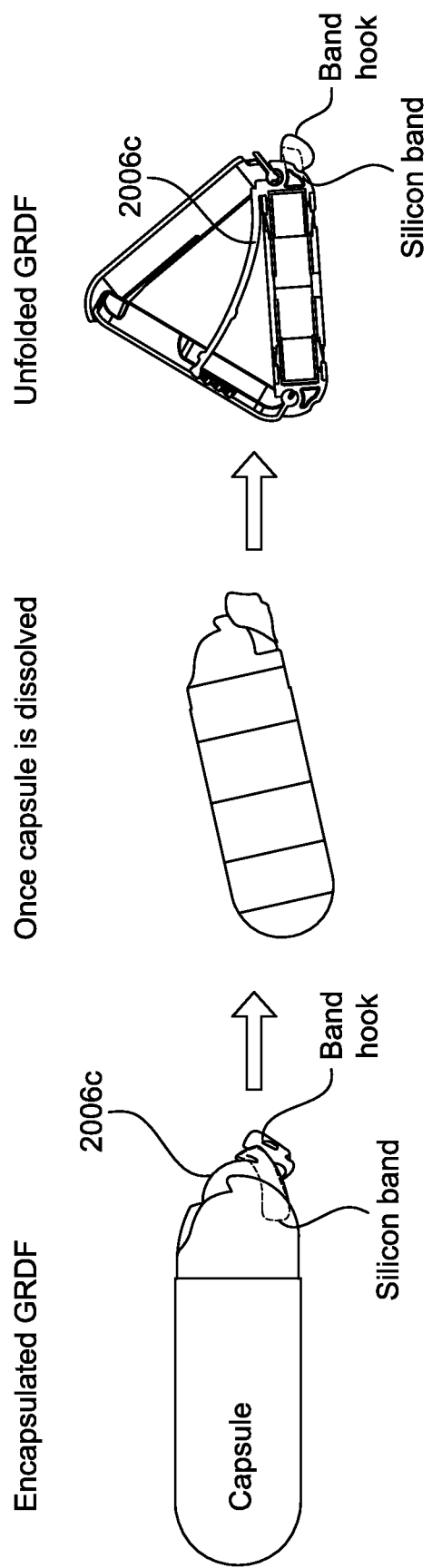
FIG. 26 illustrates arrangements of the elastic element in the compressed and expanded configurations of the GRDF and activity upon dissolution of the retainer.

A feasibility of the principle of the self-priming GRDF was tested as presented in FIG. 26. A 1.5 mm slice of silicon rubber tube having a 5 mm external diameter and a 2 mm internal diameter and mechanical properties as described in Table 15 was used as elastic band. The GRDF was placed in capsule 000 in a compressed configuration for two months. After two months the capsule was extracted, resulting in GRDF unfolded into the expanded state within less than 2 sec. The biasing member maintained its original structure with no observed deformation. The results of the experiment demonstrate the feasibility of the new non-priming mechanism of the present invention to maintain the priming status over elongated time periods, obviating the need to prime the GRDF just prior to administration.

TABLE 15

| Silicone rubber mechanical properties | | | |
|---|---|---|---|
| Test | unit | ASTM std. no. | result |
| 1 | color | — | clear |
| 2 | hardness | D2240 | 55-65 |
| 3 | tensile strength | D412 | 8.5 (minimum) |
| 4 | elongation | D412 | 500 (minimum) |
| 5 | Tear resistance | D624 | 25 (minimum) |

Thus a GRDF having improved gastric retention over previously known GRDFs has been described. In an embodiment, the GRDF comprises a body including at least two arms. In an embodiment, the body is configured to transform between a collapsed configuration for ingestion, an expanded configuration for retention within the stomach and a disassembled configuration, wherein after a predetermined time period has elapsed, the GRDF mechanically disassembles into at least two parts such that each of the disassembled parts of the GRDF is sized for exiting the stomach. In an embodiment, the GRDF further comprises an erodible insert comprising a therapeutic agent, a diagnostic agent, an electronical device, or any combination thereof. In an embodiment, the erodible insert is an elongate erodible insert having two opposing ends. In an embodiment, erosion of the erodible insert is configured to release the therapeutic agent, diagnostic agent, electronic device or combination thereof into the gastric fluid. In an embodiment the GRDF is maintained in a collapsed configuration by a retainer. In an embodiment, the retainer is a capsule, a wrapper, or band surrounding the GRDF. In an embodiment, transformation of the body of the GRDF from a compressed to an extended configuration is induced by erosion of the retainer. In an embodiment, the GRDF includes a biasing member configured to bias the GRDF into the expanded configuration, for example following erosion of the retainer. In an embodiment, the GRDF disassembly is induced by at least partial erosion of the erodible insert. In an embodiment, the GRDF disassembly is induced by erosion of at least 70%, at least 80%, at least 87%, at least 90%, at least 95%, at least 98% or about 100% of the erodible insert. In an embodiment, the GRDF disassembly is induced by the disengagement of at least one hinge assembly from at least one arm. In an embodiment, the body includes three arms and two hinge assemblies.

In an embodiment, the GRDF is adapted for stomach retention for at least 3 days, at least 4 days, at least 5 days, at least 6 days least 7 days or at least 8 days. In an embodiment, at least a portion of at least one arm of the at least two arms forms a sleeve, tube or shell. In an embodiment, the sleeve, tube or shell comprises a cavity. In an embodiment, the cavity is configured to house an erodible insert. In an embodiment, the erodible insert is contained in the cavity comprised in the sleeve, tube or shell of the at least one arm. In an embodiment, at least one opening is present or formed in the sleeve, tube or shell of the at least one arm housing the erodible insert. In an embodiment, the erodible insert is partially coated with a gastric-non-erodible coating. In an embodiment, at least one uncoated area of the erodible insert overlaps, or faces at least one opening in the sleeve of an arm housing the erodible insert, thus defining at least one "overlapping area" which is exposed to gastric fluid. In an embodiment, the erodible insert is exclusively exposed to gastric fluid at the at least on overlapping area. In an embodiment, the GRDF of the present invention includes one overlapping area. In an embodiment, the GRDF of the present invention includes more than one overlapping areas. In an embodiment, the sum area of the overlapping areas is less than 59.8 $mm^2$, or less than 40.7 $mm^2$, or less than 15.5 $mm^2$. In an embodiment, the sum area of the overlapping areas is less than 59.8 $mm^2$ and the gastric retention time is at least 4.6 days, or the sum area of the overlapping areas is less than 40.7 $mm^2$ and the gastric retention time is at least 6.6 days, or the sum area of the overlapping areas is less than 15.5 $mm^2$ and the gastric retention time is at least 8.3 days. It is to be noted that the sum exposure area may be adjusted by the person skilled in the art in order to control erosion of the erodible insert and GRDF retention time in the stomach. In an embodiment, the at least one overlapping area is present equidistant from both ends of the erodible insert. In an embodiment, the at least one overlapping area is located closer to one end of the erodible insert than to the opposing end. In an embodiment, the erosion is bidirectional towards both ends of the erodible insert and/or towards the hinge assemblies.

In an embodiment, release of the API as well as mechanical disassembly of the GRDF of the present invention are exclusively induced by erosion of the erodible insert, leading to disengagement of at least one hinge assembly from at least one arm. According to this embodiment, release of the API and mechanical disassembly of the GRDF to parts sized for exiting the stomach are not induced by erosion of the body of the GRDF, including e.g. any of the arms or the hinge assemblies. In addition, the API does not diffuse from the GRDF per se. In an embodiment, the API is not included in any part of the body of the GRDF. In this embodiment, the API is exclusively included in the erodible insert. In an embodiment, the body of the GRDF, e.g. all of the arms or the hinge assemblies, do not degrade in the stomach, and do not substantially change their size, shape and/or weight upon exposure to gastric fluid. In an embodiment, the body of the GRDF is not eroded at GRDF disassembly. In an embodiment, the body consists of gastric-non-erodible materials. In an embodiment, the at least two arms and/or the at least one hinge assembly consist of gastric-non-erodible materials. In an embodiment, the three arms and the two hinge assemblies consist of gastric-non-erodible materials. In an embodiment, the body of the GRDF and/or the at least two arms and the at least one hinge assembly consist of at least one gastric-non-erodible polymer. In a further embodiment, the at least one gastric-non-erodible polymer is a cellulose ester. In a further embodiment, the cellulose ester is selected from cellulose acetate, cellulose butyrate, or a combination thereof. In a further embodiment, the material composing the body of the GRDF does not comprise a therapeutic agent, i.e. the API is present within one or more erodible insert, which is housed in a cavity in at least one arm of the GRDF. In an embodiment, the at least two arms and/or the at least one hinge assembly are coated with a gastric-non-erodible coating.

In an embodiment, the erodible insert is housed in at least one arm of the body of the GRDF, wherein only certain surfaces of the erodible insert are exposed to the gastric environment. In an embodiment, the erodible insert is not fastened to the body of the GRDF by any physical measure selected from gluing or tethering. In an embodiment, the erodible insert is not fastened to the at least two arms by any physical measure selected from gluing or tethering. In an embodiment, the at least two arms and/or the at least one hinge assembly do not comprise an elastomer. In an embodiment, the at least two arms and/or the at least one hinge assembly comprise at least one polymer. In an embodiment, the at least one polymer comprised in the at least two arms and/or in the at least one hinge assembly is a gastric-non-erodible polymer. In an embodiment, the at least two arms and/or the at least one hinge assembly consist of gastric-non-erodible materials, e.g. low-pH-resistant polymer(s). In an embodiment, the body of the GRDF consists of gastric-non-erodible materials, e.g. low-pH-resistant polymer(s). In an embodiment, the at least two arms and the at least one hinge assembly are substantially not eroded during GRDF retention and GRDF disassembly.

The present invention also includes a manual mechanism for priming of the GRDF for administration to the patient, which obviates the need for a separate device for cocking/priming the biasing member before use. In some embodiments said priming is horizontal priming. In an embodiment, the mechanism includes
  a) a GRDF which includes a body including at least two arms, the body configured to transform between a collapsed configuration for ingestion, an expanded configuration for retention within the stomach and a disassembled configuration, wherein after a predetermined time period has elapsed, the GRDF disassembles into at least two parts such that each of the disassembled parts of the GRDF is sized for exiting the stomach;
  b) an erodible insert comprising a therapeutic agent, a diagnostic agent, an electronical device, or a combination thereof,
  c) a biasing member having a first portion and a second portion,
  d) a retainer configured to house the GRDF for ingestion, wherein the retainer has a main portion and a closing portion, wherein the retainer is configured to retain the GRDF in the collapsed configuration, and
  e) a priming member extending from an interior side of said closing portion.

In an embodiment, the GRDF disassembly into the at least two parts is a mechanical disassembly. In an embodiment, the mechanism is used by placing said GRDF in the main portion, wherein the GRDF is in a collapsed configuration, attaching the closing portion to the main portion of the retainer and pressing the closing portion in the direction of the main body so that the priming member pushes said first portion of the biasing member to a position perpendicular to said second portion of the priming biasing, thereby priming the GRDF for use. In an embodiment, the manual priming mechanism as described further comprises a retaining element. In a further embodiment, the retaining element retains the biasing member in a primed state until dissolution of the retainer. In an embodiment, the retainer is a capsule.

The present invention further includes a mechanism for self-cocking of the GRDF, obviating the need to manually cock/prime the GRDF just prior to administration. In an embodiment, self-cocking/priming mechanism includes a GRDF which includes a body including at least two arms, the body configured to transform between a collapsed configuration for ingestion, an expanded configuration for retention within the stomach and a disassembled configuration, wherein after a predetermined time period has elapsed, the GRDF disassembles into at least two parts such that each of the disassembled parts of the GRDF is sized for exiting the stomach, an erodible insert comprising a therapeutic agent, a diagnostic agent, an electronical device, or a combination thereof, a biasing member, and at least one hinge assembly, wherein the biasing member and the at least one hinge assembly are connected by an elastic element. In an embodiment, the elastic element is stretched when the GRDF is maintained in a collapsed configuration. In an embodiment, the elastic element maintains its elastic properties with minimal to no plastic deformation for at least 2 months, for at least 4 months, for at least one year, or for at least 2 years. In an embodiment, the elastic element is made of silicone rubber. In an embodiment, the elastic element has a minimal tensile strength of 8.5 GPa and minimal elongation of 500% as tested in ASTM D412. In an embodiment, the elastic element further has hardness of 40-80 shore A as tested in D2240 ASTM test. In an embodiment, the GRDF disassembly into the at least two parts is a mechanical disassembly. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A gastroretentive dosage form (GRDF) for extended retention in a human stomach, comprising:
   a. a body comprising at least two arms, the body configured to transform between a collapsed configuration for ingestion, an expanded configuration for retention within the stomach and a disassembled configuration wherein after a predetermined time period has elapsed, the GRDF disassembles into at least two parts such that each of the disassembled parts of the GRDF is sized for exiting the stomach; and
   b. an erodible insert comprising a therapeutic agent, a diagnostic agent, an electronical device, or a combination thereof;
   wherein at least a portion of at least one arm of said at least two arms forms a sleeve, tube or shell,
   wherein said sleeve, tube or shell of said at least one arm comprises a cavity and at least one opening,
   wherein said at least one opening is configured to expose said erodible insert housed in said cavity to gastric fluid;
   wherein said erodible insert is housed in said cavity; and
   wherein an uncoated surface area on said erodible insert overlaps with said at least one opening in said sleeve, tube or shell, thereby defining at least one overlapping area exposed to gastric fluid, and wherein a sum area of said at least one overlapping area is less than 59.8 mm$^2$, or less than 40.7 mm$^2$, or less than 15.5 mm$^2$.

2. The GRDF according to claim 1, wherein a sum area of the at least one overlapping area is about 15.5 to about 59.8 mm$^2$.

3. The GRDF according to claim 1, wherein the body comprises at least three arms.

4. The GRDF according to claim 1, wherein the GRDF mechanically disassembles into at least two parts such that each of the disassembled parts of the GRDF is sized for exiting the stomach.

5. The GRDF according to claim 1, wherein the body further comprises at least one hinge assembly configured to disengage from at least one arm upon at least partial erosion of the erodible insert.

6. The GRDF according to claim 1, wherein the disassembled configuration is induced by at least partial erosion of the erodible insert.

7. The GRDF according to claim 1, wherein the at least partial erosion of the erodible insert is at least 70% (w/w), at least 80% (w/w), at least 87% (w/w), at least 90% (w/w), at least 95% (w/w), at least 98% (w/w) or about 100% (w/w) erosion of the initial weight of the erodible insert.

8. The GRDF according to claim 1, wherein the GRDF includes two or more overlapping areas.

9. The GRDF according to claim 1, wherein the at least one overlapping area is equidistant from both ends of the erodible insert or ends of the arm.

10. The GRDF according to claim 1, wherein the at least one overlapping area is located closer to one end of the erodible insert than to the other end of the erodible insert.

11. The GRDF according to claim 1, wherein erosion of the erodible insert progresses bidirectionally from the overlapping area to both ends of the erodible insert.

12. The GRDF according to claim 1, wherein the erodible insert comprises more than one therapeutic agent.

* * * * *